United States Patent
Benkley, III

(10) Patent No.: US 9,659,208 B2
(45) Date of Patent: May 23, 2017

(54) BIOMETRIC IMAGE SENSING

(71) Applicant: IDEX ASA, Fornebu (NO)

(72) Inventor: Fred G. Benkley, III, Andover, MA (US)

(73) Assignee: IDEX ASA, Fornebu (NO)

( * ) Notice: Subject to any disclaimer, the term of this patent is extended or adjusted under 35 U.S.C. 154(b) by 0 days.

(21) Appl. No.: 14/946,040

(22) Filed: Nov. 19, 2015

(65) Prior Publication Data

US 2016/0154988 A1    Jun. 2, 2016

Related U.S. Application Data

(63) Continuation of application No. 13/620,271, filed on Sep. 14, 2012, now Pat. No. 9,268,988, which is a continuation of application No. 13/118,243, filed on May 27, 2011, now Pat. No. 8,866,347, which is a continuation-in-part of application No. 12/820,100, filed on Jun. 21, 2010, now Pat. No. 8,791,792, which is a continuation-in-part of application No. 12/688,790, filed on Jan. 15, 2010, now Pat. No. 8,421,890.

(51) Int. Cl.
  *G06K 9/00* (2006.01)
  *G01N 27/04* (2006.01)
  *H01H 35/00* (2006.01)

(52) U.S. Cl.
  CPC ........... *G06K 9/0002* (2013.01); *G01N 27/04* (2013.01); *G06K 9/00053* (2013.01); *Y10T 307/766* (2015.04)

(58) Field of Classification Search
  CPC ...................................................... H01H 35/00
  USPC ........................................................ 307/116
  See application file for complete search history.

(56) References Cited

U.S. PATENT DOCUMENTS

| 1,660,161 | A | 2/1928 | Hansen |
| 1,683,059 | A | 9/1928 | Van Deventer |
| 3,393,390 | A | 7/1968 | Louis |
| 3,593,319 | A | 7/1971 | Barber |
| 3,610,887 | A | 10/1971 | Betzer |
| 3,621,439 | A | 11/1971 | Newbery |
| 3,624,584 | A | 11/1971 | Ohno |
| 3,863,195 | A | 1/1975 | Bowen |

(Continued)

FOREIGN PATENT DOCUMENTS

| AU | 2011100746 A4 | 8/2011 |
| CN | 1247586 A | 3/2000 |

(Continued)

OTHER PUBLICATIONS

U.S. Appl. No. 12/820,100, Notice of Allowance dated Mar. 14, 2014, filed Jun. 21, 2010, Inventor: Fred G. Benkley, III, 32 pages.

(Continued)

*Primary Examiner* — Robert Deberadinis
(74) *Attorney, Agent, or Firm* — Rothwell, Figg, Ernst & Manbeck PC

(57) ABSTRACT

An novel sensor is provided having a plurality of substantially parallel drive lines configured to transmit a signal into a surface of a proximally located object, and also a plurality of substantially parallel pickup lines oriented proximate the drive lines and electrically separated from the pickup lines to form intrinsic electrode pairs that are impedance sensitive at each of the drive and pickup proximal locations.

33 Claims, 54 Drawing Sheets

(56) References Cited

U.S. PATENT DOCUMENTS

| | | |
|---|---|---|
| 3,960,044 A | 6/1976 | Nagai et al. |
| 3,997,863 A | 12/1976 | Luce |
| 4,151,512 A | 4/1979 | Rigannati et al. |
| 4,152,304 A | 5/1979 | Tadewald |
| 4,208,648 A | 6/1980 | Naumann |
| 4,225,850 A | 9/1980 | Chang et al. |
| 4,257,305 A | 3/1981 | Friend et al. |
| 4,273,682 A | 6/1981 | Kanamori |
| 4,310,827 A | 1/1982 | Asai |
| 4,333,068 A | 6/1982 | Kishel |
| 4,353,056 A | 10/1982 | Tsikos |
| 4,405,829 A | 9/1983 | Rivest et al. |
| 4,419,653 A | 12/1983 | Waigand |
| 4,438,158 A | 3/1984 | Eichelberger et al. |
| 4,479,392 A | 10/1984 | Froeb et al. |
| 4,492,949 A | 1/1985 | Peterson et al. |
| 4,525,859 A | 6/1985 | Bowles et al. |
| 4,550,221 A | 10/1985 | Mabusth |
| 4,570,149 A | 2/1986 | Thornburg et al. |
| 4,580,790 A | 4/1986 | Doose |
| 4,604,509 A | 8/1986 | Clancy et al. |
| 4,745,301 A | 5/1988 | Michalchik |
| 4,746,894 A | 5/1988 | Zeldman |
| 4,758,622 A | 7/1988 | Gosselin |
| 4,765,930 A | 8/1988 | Mashimo et al. |
| 4,775,765 A | 10/1988 | Kimura et al. |
| 4,817,183 A | 3/1989 | Sparrow |
| 4,827,527 A | 5/1989 | Morita et al. |
| 4,833,440 A | 5/1989 | Wojtanek |
| 4,878,040 A | 10/1989 | Tamura |
| 4,933,660 A | 6/1990 | Wynne, Jr. |
| 4,933,976 A | 6/1990 | Fishbine et al. |
| 4,952,761 A | 8/1990 | Viebrantz |
| 5,060,527 A | 10/1991 | Burgess |
| 5,068,638 A | 11/1991 | Bickely et al. |
| 5,076,566 A | 12/1991 | Kriegel |
| 5,079,949 A | 1/1992 | Tamori |
| 5,109,427 A | 4/1992 | Yang |
| 5,140,642 A | 8/1992 | Hsu et al. |
| 5,162,775 A | 11/1992 | Kuramochi et al. |
| 5,164,697 A | 11/1992 | Kramer |
| 5,270,711 A | 12/1993 | Knapp |
| 5,296,835 A | 3/1994 | Nakamura |
| 5,305,017 A | 4/1994 | Gerpheide |
| 5,319,323 A | 6/1994 | Fong |
| 5,325,442 A | 6/1994 | Knapp |
| 5,326,104 A | 7/1994 | Pease et al. |
| 5,376,913 A | 12/1994 | Pine et al. |
| 5,420,936 A | 5/1995 | Fitzpatrick et al. |
| 5,422,807 A | 6/1995 | Mitra et al. |
| 5,428,684 A | 6/1995 | Akiyama et al. |
| 5,429,006 A | 7/1995 | Tamori |
| 5,456,256 A | 10/1995 | Schneider et al. |
| 5,499,041 A | 3/1996 | Brandenburg et al. |
| 5,515,738 A | 5/1996 | Tamori |
| 5,517,738 A | 5/1996 | Wildi-Weber |
| 5,543,591 A | 8/1996 | Gillespie et al. |
| 5,569,901 A | 10/1996 | Bridgelall et al. |
| 5,610,993 A | 3/1997 | Yamamoto |
| 5,612,719 A | 3/1997 | Beermink et al. |
| 5,614,881 A | 3/1997 | Duggal et al. |
| 5,621,318 A | 4/1997 | Jacobsen et al. |
| 5,623,552 A | 4/1997 | Lane |
| 5,627,316 A | 5/1997 | De Winter et al. |
| 5,644,283 A | 7/1997 | Grosse-Wilde et al. |
| 5,650,842 A | 7/1997 | Maase et al. |
| 5,657,012 A | 8/1997 | Tait |
| 5,675,309 A | 10/1997 | DeVolpi |
| 5,689,285 A | 11/1997 | Asher |
| 5,717,777 A | 2/1998 | Wong et al. |
| 5,781,651 A | 7/1998 | Hsiao et al. |
| 5,801,681 A | 9/1998 | Sayag |
| 5,818,956 A | 10/1998 | Tuli |
| 5,821,930 A | 10/1998 | Hansen |
| 5,825,352 A | 10/1998 | Bisset et al. |
| 5,825,907 A | 10/1998 | Russo |
| 5,828,773 A | 10/1998 | Setlak et al. |
| 5,838,306 A | 11/1998 | O'Connor |
| 5,841,888 A | 11/1998 | Setlak et al. |
| 5,845,005 A | 12/1998 | Setlak et al. |
| 5,848,176 A | 12/1998 | Harra et al. |
| 5,850,450 A | 12/1998 | Schweitzer et al. |
| 5,852,670 A | 12/1998 | Setlak et al. |
| 5,861,875 A | 1/1999 | Gerpheide |
| 5,862,248 A | 1/1999 | Salatino et al. |
| 5,864,296 A | 1/1999 | Upton |
| 5,876,106 A | 3/1999 | Kordecki |
| 5,880,411 A | 3/1999 | Gillespie et al. |
| 5,884,289 A | 3/1999 | Anderson et al. |
| 5,887,343 A | 3/1999 | Salatino et al. |
| 5,889,507 A | 3/1999 | Engle et al. |
| 5,892,824 A | 4/1999 | Beatson et al. |
| 5,903,225 A | 5/1999 | Schmitt et al. |
| 5,907,327 A | 5/1999 | Ogura et al. |
| 5,909,211 A | 6/1999 | Combs et al. |
| 5,909,501 A | 6/1999 | Thebaud |
| 5,910,286 A | 6/1999 | Lipskier |
| 5,912,612 A | 6/1999 | DeVolpi |
| 5,915,757 A | 6/1999 | Tsuyama et al. |
| 5,920,384 A | 7/1999 | Borza |
| 5,920,640 A | 7/1999 | Salatino et al. |
| 5,940,526 A | 8/1999 | Setlak et al. |
| 5,943,052 A | 8/1999 | Allen et al. |
| 5,945,929 A | 8/1999 | Westra |
| 5,949,325 A | 9/1999 | Devolpi |
| 5,953,441 A | 9/1999 | Setlak |
| 5,956,415 A | 9/1999 | McCalley et al. |
| 5,963,679 A | 10/1999 | Setlak |
| 5,982,894 A | 11/1999 | McCalley et al. |
| 5,995,084 A | 11/1999 | Chan et al. |
| 5,999,084 A | 12/1999 | Armstrong |
| 5,999,637 A | 12/1999 | Toyoda et al. |
| 6,002,815 A | 12/1999 | Immega et al. |
| 6,011,589 A | 1/2000 | Matsuura et al. |
| 6,016,355 A | 1/2000 | Dickinson et al. |
| 6,021,211 A | 2/2000 | Setlak et al. |
| 6,028,773 A | 2/2000 | Hundt |
| 6,047,281 A | 4/2000 | Wilson et al. |
| 6,047,282 A | 4/2000 | Wilson et al. |
| 6,049,620 A | 4/2000 | Dickinson et al. |
| 6,052,475 A | 4/2000 | Upton |
| 6,057,540 A | 5/2000 | Gordon et al. |
| 6,057,830 A | 5/2000 | Chan et al. |
| 6,061,051 A | 5/2000 | Chan et al. |
| 6,061,464 A | 5/2000 | Leger |
| 6,067,368 A | 5/2000 | Setlak et al. |
| 6,069,970 A | 5/2000 | Salatino et al. |
| 6,070,159 A | 5/2000 | Wilson et al. |
| 6,073,343 A | 6/2000 | Petrick et al. |
| 6,076,566 A | 6/2000 | Lowe |
| 6,088,471 A | 7/2000 | Setlak et al. |
| 6,088,585 A | 7/2000 | Schmitt et al. |
| 6,098,175 A | 8/2000 | Lee |
| 6,098,330 A | 8/2000 | Schmitt et al. |
| 6,118,318 A | 9/2000 | Fifield et al. |
| 6,134,340 A | 10/2000 | Hsu et al. |
| 6,135,958 A | 10/2000 | Mikula-Curtis et al. |
| 6,157,722 A | 12/2000 | Lerner et al. |
| 6,161,213 A | 12/2000 | Lofstrom |
| 6,173,400 B1 | 1/2001 | Perlman et al. |
| 6,175,407 B1 | 1/2001 | Sartor |
| 6,181,807 B1 | 1/2001 | Setlak et al. |
| 6,182,076 B1 | 1/2001 | Yu et al. |
| 6,182,892 B1 | 2/2001 | Angelo et al. |
| 6,185,318 B1 | 2/2001 | Jain et al. |
| 6,208,329 B1 | 3/2001 | Ballare |
| 6,215,477 B1 | 4/2001 | Morrison |
| 6,234,031 B1 | 5/2001 | Suga |
| 6,239,790 B1 | 5/2001 | Martinelli et al. |
| 6,241,288 B1 | 6/2001 | Bergenek et al. |
| 6,248,655 B1 | 6/2001 | Machida et al. |
| 6,256,012 B1 | 7/2001 | Devolpi |
| 6,256,022 B1 | 7/2001 | Manaresi et al. |
| 6,259,108 B1 | 7/2001 | Antonelli et al. |

(56) References Cited

U.S. PATENT DOCUMENTS

| | | |
|---|---|---|
| 6,259,804 B1 | 7/2001 | Setlak et al. |
| 6,278,443 B1 | 8/2001 | Amro et al. |
| 6,289,114 B1 | 9/2001 | Mainguet |
| 6,317,508 B1 | 11/2001 | Kramer et al. |
| 6,320,394 B1 | 11/2001 | Tartagni |
| 6,323,846 B1 | 11/2001 | Westerman et al. |
| 6,330,345 B1 | 12/2001 | Russo et al. |
| 6,332,193 B1 | 12/2001 | Glass et al. |
| 6,333,989 B1 | 12/2001 | Borza |
| 6,337,918 B1 | 1/2002 | Holchan |
| 6,337,919 B1 | 1/2002 | Duton |
| 6,344,791 B1 | 2/2002 | Armstrong |
| 6,346,739 B1 | 2/2002 | Lepert et al. |
| 6,347,040 B1 | 2/2002 | Fries et al. |
| 6,357,302 B1 | 3/2002 | Knapp |
| 6,360,004 B1 | 3/2002 | Akizuki |
| 6,362,633 B1 | 3/2002 | Tartagni |
| 6,370,965 B1 | 4/2002 | Knapp |
| 6,376,393 B1 | 4/2002 | Newton et al. |
| 6,392,636 B1 | 5/2002 | Ferrari et al. |
| 6,399,994 B2 | 6/2002 | Shobu |
| 6,400,836 B2 | 6/2002 | Senior |
| 6,404,323 B1 | 6/2002 | Schrum et al. |
| 6,404,900 B1 | 6/2002 | Qian et al. |
| 6,408,087 B1 | 6/2002 | Kramer |
| 6,437,682 B1 | 8/2002 | Vance |
| 6,442,286 B1 | 8/2002 | Kramer |
| 6,459,424 B1 | 10/2002 | Resman |
| 6,459,804 B2 | 10/2002 | Mainguet |
| 6,473,072 B1 | 10/2002 | Comiskey et al. |
| 6,483,931 B2 | 11/2002 | Kalnitsky et al. |
| 6,501,284 B1 | 12/2002 | Gozzini |
| 6,509,501 B2 | 1/2003 | Eicken et al. |
| 6,512,381 B2 | 1/2003 | Kramer |
| 6,515,488 B1 | 2/2003 | Thomas |
| 6,518,560 B1 | 2/2003 | Yeh et al. |
| 6,522,773 B1 | 2/2003 | Houdeau |
| 6,525,547 B2 | 2/2003 | Hayes |
| 6,535,622 B1 | 3/2003 | Russo et al. |
| 6,539,101 B1 | 3/2003 | Black |
| 6,546,122 B1 | 4/2003 | Russo |
| 6,563,101 B1 | 5/2003 | Tullis |
| 6,580,816 B2 | 6/2003 | Kramer et al. |
| 6,597,289 B2 | 7/2003 | Sabatini |
| 6,603,462 B2 | 8/2003 | Matusis |
| 6,628,812 B1 | 9/2003 | Setlak et al. |
| 6,636,053 B1 | 10/2003 | Gozzini |
| 6,643,389 B1 | 11/2003 | Raynal et al. |
| 6,654,484 B2 | 11/2003 | Topping |
| 6,661,631 B1 | 12/2003 | Meador et al. |
| 6,664,951 B1 | 12/2003 | Fujii et al. |
| 6,667,439 B2 | 12/2003 | Salatino et al. |
| 6,668,072 B1 | 12/2003 | Hribernig et al. |
| 6,672,174 B2 | 1/2004 | Deconde et al. |
| 6,680,731 B2 | 1/2004 | Gerpheide |
| 6,681,034 B1 | 1/2004 | Russo |
| 6,683,971 B1 | 1/2004 | Salatino et al. |
| 6,738,050 B2 | 5/2004 | Comiskey et al. |
| 6,741,729 B2 | 5/2004 | Bjorn et al. |
| 6,744,910 B1 | 6/2004 | McClurg et al. |
| 6,754,365 B1 | 6/2004 | Wen et al. |
| 6,757,002 B1 | 6/2004 | Oross et al. |
| 6,766,040 B1 | 7/2004 | Catalano et al. |
| 6,785,407 B1 | 8/2004 | Tschudi et al. |
| 6,836,230 B2 | 12/2004 | Pailleur et al. |
| 6,838,905 B1 | 1/2005 | Doyle |
| 6,876,756 B1 | 4/2005 | Vieweg |
| 6,886,104 B1 | 4/2005 | McClurg et al. |
| 6,897,002 B2 | 5/2005 | Teraoka et al. |
| 6,898,299 B1 | 5/2005 | Brooks |
| 6,914,517 B2 | 7/2005 | Kinsella |
| 6,924,496 B2 | 8/2005 | Manansala |
| 6,937,748 B1 | 8/2005 | Schneider et al. |
| 6,941,001 B1 | 9/2005 | Bolle et al. |
| 6,941,810 B2 | 9/2005 | Okada |
| 6,950,540 B2 | 9/2005 | Higuchi |
| 6,959,874 B2 | 11/2005 | Bardwell |
| 6,961,452 B2 | 11/2005 | Fujii |
| 6,963,626 B1 | 11/2005 | Shaeffer et al. |
| 6,970,584 B2 | 11/2005 | O'Gorman et al. |
| 6,980,672 B2 | 12/2005 | Saito et al. |
| 6,983,882 B2 | 1/2006 | Cassone |
| 7,002,553 B2 | 2/2006 | Shkolnikov |
| 7,003,670 B2 | 2/2006 | Heaven et al. |
| 7,004,389 B1 | 2/2006 | Robinson et al. |
| 7,013,030 B2 | 3/2006 | Wong et al. |
| 7,014,107 B2 | 3/2006 | Singer et al. |
| 7,020,270 B1 | 3/2006 | Ghassabian |
| 7,020,591 B1 | 3/2006 | Wei et al. |
| 7,027,626 B2 | 4/2006 | Funada |
| 7,030,860 B1 | 4/2006 | Hsu et al. |
| 7,035,443 B2 | 4/2006 | Wong |
| 7,039,223 B2 | 5/2006 | Wong |
| 7,042,535 B2 | 5/2006 | Katoh et al. |
| 7,043,061 B2 | 5/2006 | Hamid et al. |
| 7,043,644 B2 | 5/2006 | DeBruine |
| 7,046,230 B2 | 5/2006 | Zadesky et al. |
| 7,054,470 B2 | 5/2006 | Bolle et al. |
| 7,064,743 B2 | 6/2006 | Nishikawa |
| 7,099,496 B2 | 8/2006 | Benkley, III |
| 7,099,497 B2 | 8/2006 | Chou et al. |
| 7,102,364 B2 | 9/2006 | Umeda et al. |
| 7,110,577 B1 | 9/2006 | Tschudi |
| 7,113,622 B2 | 9/2006 | Hamid |
| 7,126,389 B1 | 10/2006 | McRae et al. |
| 7,129,926 B2 | 10/2006 | Mathiassen et al. |
| 7,136,514 B1 | 11/2006 | Wong |
| 7,146,024 B2 | 12/2006 | Benkley |
| 7,146,026 B2 | 12/2006 | Russon et al. |
| 7,146,029 B2 | 12/2006 | Manansala |
| 7,184,581 B2 | 2/2007 | Johansen et al. |
| 7,190,816 B2 | 3/2007 | Mitsuyu et al. |
| 7,194,392 B2 | 3/2007 | Tuken et al. |
| 7,194,393 B2 | 3/2007 | Wei |
| 7,197,168 B2 | 3/2007 | Russo |
| 7,200,250 B2 | 4/2007 | Chou |
| 7,203,347 B2 | 4/2007 | Hamid |
| 7,239,153 B2 | 7/2007 | Nysaether |
| 7,239,728 B1 | 7/2007 | Choi et al. |
| 7,251,351 B2 | 7/2007 | Mathiassen et al. |
| 7,258,279 B2 | 8/2007 | Schneider et al. |
| 7,260,246 B2 | 8/2007 | Fujii |
| 7,263,212 B2 | 8/2007 | Kawabe |
| 7,263,213 B2 | 8/2007 | Rowe |
| 7,269,256 B2 | 9/2007 | Rosen |
| 7,280,679 B2 | 10/2007 | Russo |
| 7,283,534 B1 | 10/2007 | Kelly et al. |
| 7,289,649 B1 | 10/2007 | Walley et al. |
| 7,290,323 B2 | 11/2007 | Deconde et al. |
| 7,299,360 B2 | 11/2007 | Russo |
| 7,308,121 B2 | 12/2007 | Mathiassen et al. |
| 7,308,122 B2 | 12/2007 | McClurg et al. |
| 7,321,672 B2 | 1/2008 | Sasaki et al. |
| 7,356,169 B2 | 4/2008 | Hamid |
| 7,360,688 B1 | 4/2008 | Harris |
| 7,369,658 B2 | 5/2008 | Batruni |
| 7,369,688 B2 | 5/2008 | Ser et al. |
| 7,379,569 B2 | 5/2008 | Chikazawa et al. |
| 7,398,390 B2 | 7/2008 | Hyser |
| 7,403,644 B2 | 7/2008 | Bohn et al. |
| 7,409,876 B2 | 8/2008 | Ganapathi et al. |
| 7,412,083 B2 | 8/2008 | Takahashi |
| 7,417,536 B2 | 8/2008 | Lakshmanan |
| 7,424,618 B2 | 9/2008 | Roy et al. |
| 7,447,339 B2 | 11/2008 | Mimura et al. |
| 7,447,911 B2 | 11/2008 | Chou et al. |
| 7,460,697 B2 | 12/2008 | Erhart et al. |
| 7,463,756 B2 | 12/2008 | Benkley |
| 7,474,772 B2 | 1/2009 | Russo et al. |
| 7,505,611 B2 | 3/2009 | Fyke |
| 7,505,613 B2 | 3/2009 | Russo |
| 7,518,382 B2 | 4/2009 | Vermesan et al. |
| 7,543,737 B2 | 6/2009 | Bensimon et al. |
| 7,565,548 B2 | 7/2009 | Fiske et al. |

(56) References Cited

U.S. PATENT DOCUMENTS

| | | |
|---|---|---|
| 7,574,022 B2 | 8/2009 | Russo |
| 7,590,269 B2 | 9/2009 | Creasey et al. |
| 7,599,530 B2 | 10/2009 | Boshra |
| 7,606,400 B2 | 10/2009 | Ryhanen et al. |
| 7,623,659 B2 | 11/2009 | Huang et al. |
| 7,643,950 B1 | 1/2010 | Getzin et al. |
| 7,646,897 B2 | 1/2010 | Fyke |
| 7,681,232 B2 | 3/2010 | Nordentoft et al. |
| 7,685,629 B1 | 3/2010 | White et al. |
| 7,689,013 B2 | 3/2010 | Shinzaki |
| 7,706,581 B2 | 4/2010 | Drews et al. |
| 7,733,697 B2 | 6/2010 | Picca et al. |
| 7,751,595 B2 | 7/2010 | Russo |
| 7,751,601 B2 | 7/2010 | Benkley |
| 7,754,022 B2 | 7/2010 | Barnhill et al. |
| 7,768,273 B1 | 8/2010 | Kalnitsky et al. |
| 7,787,660 B2 | 8/2010 | Boyd et al. |
| 7,821,501 B2 | 10/2010 | Felder |
| 7,831,840 B1 | 11/2010 | Love et al. |
| 7,843,438 B2 | 11/2010 | Onoda |
| 7,844,579 B2 | 11/2010 | Peterson et al. |
| 7,864,992 B2 | 1/2011 | Riedijk et al. |
| 7,899,216 B2 | 3/2011 | Watanabe et al. |
| 7,953,258 B2 | 5/2011 | Dean et al. |
| 7,986,193 B2 | 7/2011 | Krah |
| 8,005,276 B2 | 8/2011 | Dean et al. |
| 8,023,700 B2 | 9/2011 | Riionheimo |
| 8,031,916 B2 | 10/2011 | Abiko et al. |
| 8,077,935 B2 | 12/2011 | Geoffroy et al. |
| 8,107,212 B2 | 1/2012 | Nelson et al. |
| 8,116,540 B2 | 2/2012 | Dean et al. |
| 8,421,890 B2 | 4/2013 | Benkley, III |
| 8,538,095 B2 | 9/2013 | Fedele et al. |
| 8,619,057 B2 | 12/2013 | Kobayashi et al. |
| 8,638,994 B2 | 1/2014 | Kraemer et al. |
| 8,711,105 B2 | 4/2014 | Gray et al. |
| 2001/0009112 A1 | 7/2001 | Delaye |
| 2001/0012036 A1 | 8/2001 | Giere et al. |
| 2001/0017934 A1 | 8/2001 | Paloniemi et al. |
| 2001/0026636 A1 | 10/2001 | Mainguet |
| 2001/0029527 A1 | 10/2001 | Goshen |
| 2001/0030644 A1 | 10/2001 | Allport |
| 2001/0032319 A1 | 10/2001 | Setlak |
| 2001/0036299 A1 | 11/2001 | Senior |
| 2001/0043728 A1 | 11/2001 | Kramer et al. |
| 2002/0025062 A1 | 2/2002 | Black |
| 2002/0054695 A1 | 5/2002 | Bjorn et al. |
| 2002/0061125 A1 | 5/2002 | Fujii |
| 2002/0064892 A1 | 5/2002 | Lepert et al. |
| 2002/0067845 A1 | 6/2002 | Griffis |
| 2002/0073046 A1 | 6/2002 | David |
| 2002/0089044 A1 | 7/2002 | Simmons et al. |
| 2002/0089410 A1 | 7/2002 | Janiak et al. |
| 2002/0096731 A1 | 7/2002 | Wu et al. |
| 2002/0109671 A1 | 8/2002 | Kawasome |
| 2002/0122026 A1 | 9/2002 | Bergstrom |
| 2002/0126516 A1 | 9/2002 | Jeon |
| 2002/0130673 A1 | 9/2002 | Pelrine et al. |
| 2002/0133725 A1 | 9/2002 | Roy et al. |
| 2002/0152048 A1 | 10/2002 | Hayes |
| 2002/0156726 A1 | 10/2002 | Kleckner et al. |
| 2002/0164057 A1 | 11/2002 | Kramer |
| 2002/0181749 A1 | 12/2002 | Matsumoto et al. |
| 2002/0186203 A1 | 12/2002 | Huang |
| 2002/0188854 A1 | 12/2002 | Heaven et al. |
| 2003/0002717 A1 | 1/2003 | Hamid |
| 2003/0002718 A1 | 1/2003 | Hamid |
| 2003/0002719 A1 | 1/2003 | Hamid et al. |
| 2003/0016849 A1 | 1/2003 | Andrade |
| 2003/0021495 A1 | 1/2003 | Cheng |
| 2003/0025606 A1 | 2/2003 | Sabatini |
| 2003/0028811 A1 | 2/2003 | Walker et al. |
| 2003/0035568 A1 | 2/2003 | Mitev et al. |
| 2003/0035570 A1 | 2/2003 | Benkley |
| 2003/0035572 A1 | 2/2003 | Kalnitsky et al. |
| 2003/0044051 A1 | 3/2003 | Fujieda |
| 2003/0063782 A1 | 4/2003 | Acharya et al. |
| 2003/0068072 A1 | 4/2003 | Hamid |
| 2003/0074559 A1 | 4/2003 | Riggs |
| 2003/0076301 A1 | 4/2003 | Tsuk et al. |
| 2003/0076303 A1 | 4/2003 | Huppi |
| 2003/0095096 A1 | 5/2003 | Robbin et al. |
| 2003/0095691 A1 | 5/2003 | Nobuhara et al. |
| 2003/0101348 A1 | 5/2003 | Russo et al. |
| 2003/0102874 A1 | 6/2003 | Lane et al. |
| 2003/0107608 A1 | 6/2003 | Hong et al. |
| 2003/0108226 A1 | 6/2003 | Goodman et al. |
| 2003/0108227 A1 | 6/2003 | Philomin et al. |
| 2003/0115475 A1 | 6/2003 | Russo et al. |
| 2003/0115490 A1 | 6/2003 | Russo et al. |
| 2003/0123714 A1 | 7/2003 | O'Gorman et al. |
| 2003/0123715 A1 | 7/2003 | Uchida |
| 2003/0126448 A1 | 7/2003 | Russo |
| 2003/0135764 A1 | 7/2003 | Lu |
| 2003/0141959 A1 | 7/2003 | Keogh et al. |
| 2003/0147015 A1 | 8/2003 | Katoh et al. |
| 2003/0161510 A1 | 8/2003 | Fujii |
| 2003/0161512 A1 | 8/2003 | Mathiassen et al. |
| 2003/0169228 A1 | 9/2003 | Mathiassen et al. |
| 2003/0174871 A1 | 9/2003 | Yoshioka et al. |
| 2003/0186157 A1 | 10/2003 | Teraoka et al. |
| 2003/0209293 A1 | 11/2003 | Sako et al. |
| 2003/0214481 A1 | 11/2003 | Xiong |
| 2003/0215116 A1 | 11/2003 | Brandt et al. |
| 2003/0224553 A1 | 12/2003 | Manansala |
| 2004/0012773 A1 | 1/2004 | Puttkammer |
| 2004/0014457 A1 | 1/2004 | Stevens |
| 2004/0022001 A1 | 2/2004 | Chu et al. |
| 2004/0042642 A1 | 3/2004 | Bolle et al. |
| 2004/0050930 A1 | 3/2004 | Rowe |
| 2004/0066613 A1 | 4/2004 | Leitao |
| 2004/0076313 A1 | 4/2004 | Bronstein et al. |
| 2004/0076314 A1 | 4/2004 | Cheng |
| 2004/0081339 A1 | 4/2004 | Benkley |
| 2004/0096086 A1 | 5/2004 | Miyasaka et al. |
| 2004/0113956 A1 | 6/2004 | Bellwood et al. |
| 2004/0120400 A1 | 6/2004 | Linzer |
| 2004/0125990 A1 | 7/2004 | Goodman et al. |
| 2004/0125993 A1 | 7/2004 | Zhao et al. |
| 2004/0128521 A1 | 7/2004 | Russo |
| 2004/0129787 A1 | 7/2004 | Saito |
| 2004/0136612 A1 | 7/2004 | Meister et al. |
| 2004/0148526 A1 | 7/2004 | Sands et al. |
| 2004/0156538 A1 | 8/2004 | Greschitz et al. |
| 2004/0172339 A1 | 9/2004 | Snelgrove et al. |
| 2004/0179718 A1 | 9/2004 | Chou |
| 2004/0184641 A1 | 9/2004 | Nagasaka et al. |
| 2004/0186682 A1 | 9/2004 | Ting |
| 2004/0190761 A1 | 9/2004 | Lee |
| 2004/0208346 A1 | 10/2004 | Baharav et al. |
| 2004/0208347 A1 | 10/2004 | Baharav et al. |
| 2004/0208348 A1 | 10/2004 | Baharav et al. |
| 2004/0213441 A1 | 10/2004 | Tschudi |
| 2004/0215689 A1 | 10/2004 | Dooley et al. |
| 2004/0228505 A1 | 11/2004 | Sugimoto |
| 2004/0228508 A1 | 11/2004 | Shigeta |
| 2004/0230536 A1 | 11/2004 | Fung et al. |
| 2004/0240712 A1 | 12/2004 | Rowe et al. |
| 2004/0252867 A1 | 12/2004 | Lan et al. |
| 2004/0257196 A1 | 12/2004 | Kotzin |
| 2004/0258282 A1 | 12/2004 | Bjorn et al. |
| 2004/0263479 A1 | 12/2004 | Shkolnikov |
| 2005/0012714 A1 | 1/2005 | Russo et al. |
| 2005/0031174 A1 | 2/2005 | Ryhanen et al. |
| 2005/0036665 A1 | 2/2005 | Higuchi |
| 2005/0041841 A1 | 2/2005 | Yoo et al. |
| 2005/0041885 A1 | 2/2005 | Russo |
| 2005/0047485 A1 | 3/2005 | Khayrallah et al. |
| 2005/0089200 A1 | 4/2005 | Nysaether |
| 2005/0100196 A1 | 5/2005 | Scott et al. |
| 2005/0100938 A1 | 5/2005 | Hofmann et al. |
| 2005/0109835 A1 | 5/2005 | Jacoby et al. |
| 2005/0110103 A1 | 5/2005 | Setlak |
| 2005/0111708 A1 | 5/2005 | Chou |

(56) References Cited

U.S. PATENT DOCUMENTS

| | | |
|---|---|---|
| 2005/0122785 A1 | 6/2005 | Umeda et al. |
| 2005/0123176 A1 | 6/2005 | Ishil et al. |
| 2005/0136200 A1 | 6/2005 | Durell et al. |
| 2005/0139656 A1 | 6/2005 | Arnouse |
| 2005/0151065 A1 | 7/2005 | Min |
| 2005/0162402 A1 | 7/2005 | Watanachote |
| 2005/0169503 A1 | 8/2005 | Howell et al. |
| 2005/0178827 A1 | 8/2005 | Shatford |
| 2005/0179657 A1 | 8/2005 | Russo et al. |
| 2005/0198377 A1 | 9/2005 | Ferguson et al. |
| 2005/0210271 A1 | 9/2005 | Chou et al. |
| 2005/0219200 A1 | 10/2005 | Weng |
| 2005/0220329 A1 | 10/2005 | Payne et al. |
| 2005/0221798 A1 | 10/2005 | Sengupta et al. |
| 2005/0231213 A1 | 10/2005 | Chou et al. |
| 2005/0238212 A1 | 10/2005 | Du et al. |
| 2005/0244038 A1 | 11/2005 | Benkley |
| 2005/0244039 A1 | 11/2005 | Geoffroy et al. |
| 2005/0247559 A1 | 11/2005 | Frey et al. |
| 2005/0249386 A1 | 11/2005 | Juh |
| 2005/0254694 A1 | 11/2005 | Goodman et al. |
| 2005/0258952 A1 | 11/2005 | Utter et al. |
| 2005/0259851 A1 | 11/2005 | Fyke |
| 2005/0259852 A1 | 11/2005 | Russo |
| 2005/0269402 A1 | 12/2005 | Spitzer et al. |
| 2005/0281441 A1 | 12/2005 | Martinsen et al. |
| 2006/0002597 A1 | 1/2006 | Rowe |
| 2006/0006224 A1 | 1/2006 | Modi |
| 2006/0034043 A1 | 2/2006 | Hisano et al. |
| 2006/0055500 A1 | 3/2006 | Burke et al. |
| 2006/0066572 A1 | 3/2006 | Yumoto et al. |
| 2006/0078174 A1 | 4/2006 | Russo |
| 2006/0078176 A1 | 4/2006 | Abiko et al. |
| 2006/0083411 A1 | 4/2006 | Benkley |
| 2006/0097991 A1 | 5/2006 | Hotelling et al. |
| 2006/0103633 A1 | 5/2006 | Gioeli |
| 2006/0110013 A1 | 5/2006 | Lee |
| 2006/0110537 A1 | 5/2006 | Huang et al. |
| 2006/0140461 A1 | 6/2006 | Kim et al. |
| 2006/0141960 A1 | 6/2006 | Fernandez et al. |
| 2006/0144953 A1 | 7/2006 | Takao |
| 2006/0170528 A1 | 8/2006 | Funushige et al. |
| 2006/0187200 A1 | 8/2006 | Martin |
| 2006/0190737 A1 | 8/2006 | Miyasaka |
| 2006/0210082 A1 | 9/2006 | Devadas et al. |
| 2006/0214512 A1 | 9/2006 | Iwata |
| 2006/0214921 A1 | 9/2006 | Takahashi et al. |
| 2006/0239514 A1 | 10/2006 | Watanabe et al. |
| 2006/0242268 A1 | 10/2006 | Omernick et al. |
| 2006/0244722 A1 | 11/2006 | Gust |
| 2006/0249008 A1 | 11/2006 | Luther |
| 2006/0259873 A1 | 11/2006 | Mister |
| 2006/0261174 A1 | 11/2006 | Zellner et al. |
| 2006/0267385 A1 | 11/2006 | Steenwyk et al. |
| 2006/0271793 A1 | 11/2006 | Devadas et al. |
| 2006/0280346 A1 | 12/2006 | Machida |
| 2006/0287963 A1 | 12/2006 | Steeves et al. |
| 2007/0014443 A1 | 1/2007 | Russo |
| 2007/0021198 A1 | 1/2007 | Muir et al. |
| 2007/0031011 A1 | 2/2007 | Erhart et al. |
| 2007/0034783 A1 | 2/2007 | Eliasson et al. |
| 2007/0036400 A1 | 2/2007 | Watanabe et al. |
| 2007/0057763 A1 | 3/2007 | Blattner et al. |
| 2007/0061126 A1 | 3/2007 | Russo et al. |
| 2007/0067828 A1 | 3/2007 | Bychkov |
| 2007/0072631 A1 | 3/2007 | Mock et al. |
| 2007/0076923 A1 | 4/2007 | Chiu |
| 2007/0076926 A1 | 4/2007 | Schneider et al. |
| 2007/0076951 A1 | 4/2007 | Tanaka et al. |
| 2007/0086634 A1 | 4/2007 | Setlak et al. |
| 2007/0090312 A1 | 4/2007 | Stallinga et al. |
| 2007/0125937 A1 | 6/2007 | Eliasson et al. |
| 2007/0138299 A1 | 6/2007 | Mitra |
| 2007/0180261 A1 | 8/2007 | Akkermans et al. |
| 2007/0196002 A1 | 8/2007 | Choi et al. |
| 2007/0198141 A1 | 8/2007 | Moore |
| 2007/0198435 A1 | 8/2007 | Siegal et al. |
| 2007/0210895 A1 | 9/2007 | Kuhlman |
| 2007/0211923 A1 | 9/2007 | Kuhlman |
| 2007/0228154 A1 | 10/2007 | Tran |
| 2007/0236330 A1 | 10/2007 | Cho et al. |
| 2007/0237366 A1 | 10/2007 | Maletsky |
| 2007/0248249 A1 | 10/2007 | Stoianov |
| 2007/0274575 A1 | 11/2007 | Russo |
| 2007/0292005 A1 | 12/2007 | Lo et al. |
| 2008/0002867 A1 | 1/2008 | Mathiassen et al. |
| 2008/0013803 A1 | 1/2008 | Lo et al. |
| 2008/0013805 A1 | 1/2008 | Sengupta et al. |
| 2008/0013808 A1 | 1/2008 | Russo et al. |
| 2008/0019578 A1 | 1/2008 | Saito et al. |
| 2008/0030207 A1 | 2/2008 | Vermesan et al. |
| 2008/0042813 A1 | 2/2008 | Wheatley |
| 2008/0042814 A1 | 2/2008 | Hurwitz |
| 2008/0049980 A1 | 2/2008 | Castaneda et al. |
| 2008/0049987 A1 | 2/2008 | Champagne et al. |
| 2008/0049989 A1 | 2/2008 | Iseri et al. |
| 2008/0062140 A1 | 3/2008 | Hotelling et al. |
| 2008/0063245 A1 | 3/2008 | Benkley et al. |
| 2008/0069412 A1 | 3/2008 | Champagne et al. |
| 2008/0101662 A1 | 5/2008 | Lo et al. |
| 2008/0101663 A1 | 5/2008 | Lo et al. |
| 2008/0101705 A1 | 5/2008 | Mohamed et al. |
| 2008/0103995 A1 | 5/2008 | Mohamed et al. |
| 2008/0105936 A1 | 5/2008 | Nakamura |
| 2008/0126260 A1 | 5/2008 | Cox et al. |
| 2008/0133373 A1 | 6/2008 | Perdomo et al. |
| 2008/0138078 A1 | 6/2008 | Alameh |
| 2008/0138079 A1 | 6/2008 | Mui et al. |
| 2008/0154816 A1 | 6/2008 | Xiao |
| 2008/0158178 A1 | 7/2008 | Hotelling et al. |
| 2008/0159688 A1 | 7/2008 | Schellinger et al. |
| 2008/0159698 A1 | 7/2008 | Alameh et al. |
| 2008/0159699 A1 | 7/2008 | Zeiger et al. |
| 2008/0165139 A1 | 7/2008 | Hotelling et al. |
| 2008/0165158 A1 | 7/2008 | Hotelling et al. |
| 2008/0166028 A1 | 7/2008 | Turek et al. |
| 2008/0169345 A1 | 7/2008 | Keane et al. |
| 2008/0170695 A1 | 7/2008 | Adler et al. |
| 2008/0174570 A1 | 7/2008 | Jobs et al. |
| 2008/0175450 A1 | 7/2008 | Scott et al. |
| 2008/0178008 A1 | 7/2008 | Takahashi et al. |
| 2008/0179112 A1 | 7/2008 | Qin et al. |
| 2008/0185193 A1 | 8/2008 | Lin |
| 2008/0185429 A1 | 8/2008 | Saville |
| 2008/0201265 A1 | 8/2008 | Hewton |
| 2008/0205714 A1 | 8/2008 | Benkley et al. |
| 2008/0219521 A1 | 9/2008 | Benkley et al. |
| 2008/0222049 A1 | 9/2008 | Loomis et al. |
| 2008/0223925 A1 | 9/2008 | Saito et al. |
| 2008/0226132 A1 | 9/2008 | Gardner |
| 2008/0238878 A1 | 10/2008 | Wang |
| 2008/0240523 A1 | 10/2008 | Benkley et al. |
| 2008/0244277 A1 | 10/2008 | Orsini et al. |
| 2008/0247652 A1 | 10/2008 | Mohamed |
| 2008/0267462 A1 | 10/2008 | Nelson et al. |
| 2008/0273767 A1 | 11/2008 | Lo et al. |
| 2008/0273769 A1 | 11/2008 | Lo et al. |
| 2008/0279373 A1 | 11/2008 | Erhart et al. |
| 2008/0279416 A1 | 11/2008 | Lo et al. |
| 2008/0285813 A1 | 11/2008 | Holm |
| 2008/0298648 A1 | 12/2008 | Lo et al. |
| 2008/0309633 A1 | 12/2008 | Hotelling et al. |
| 2008/0316183 A1 | 12/2008 | Westerman et al. |
| 2008/0317302 A1 | 12/2008 | Abdallah et al. |
| 2009/0009486 A1 | 1/2009 | Sato et al. |
| 2009/0016913 A1 | 1/2009 | Smits |
| 2009/0024499 A1 | 1/2009 | Ribble |
| 2009/0056124 A1 | 3/2009 | Krebs et al. |
| 2009/0060728 A1 | 3/2009 | Grimes et al. |
| 2009/0074255 A1 | 3/2009 | Holm |
| 2009/0083847 A1 | 3/2009 | Fadell et al. |
| 2009/0083850 A1 | 3/2009 | Fadell |
| 2009/0130369 A1 | 5/2009 | Huang et al. |
| 2009/0153297 A1 | 6/2009 | Gardner |

(56) References Cited

U.S. PATENT DOCUMENTS

| | | |
|---|---|---|
| 2009/0154779 A1 | 6/2009 | Satyan et al. |
| 2009/0155456 A1 | 6/2009 | Benkley et al. |
| 2009/0169071 A1 | 7/2009 | Bond et al. |
| 2009/0169072 A1 | 7/2009 | Lo et al. |
| 2009/0174974 A1 | 7/2009 | Huang et al. |
| 2009/0210722 A1 | 8/2009 | Russo |
| 2009/0228952 A1 | 9/2009 | Gillig et al. |
| 2009/0237135 A1 | 9/2009 | Ramaraju et al. |
| 2009/0244820 A1 | 10/2009 | Kusaka et al. |
| 2009/0252384 A1 | 10/2009 | Dean et al. |
| 2009/0252385 A1 | 10/2009 | Dean et al. |
| 2009/0252386 A1 | 10/2009 | Dean et al. |
| 2009/0273573 A1 | 11/2009 | Hotelling |
| 2009/0273577 A1 | 11/2009 | Chen et al. |
| 2009/0279742 A1 | 11/2009 | Abiko |
| 2009/0284398 A1 | 11/2009 | Shen et al. |
| 2009/0284495 A1 | 11/2009 | Geaghan et al. |
| 2009/0314621 A1 | 12/2009 | Hotelling |
| 2009/0319435 A1 | 12/2009 | Little et al. |
| 2009/0324028 A1 | 12/2009 | Russo |
| 2010/0019032 A1 | 1/2010 | Kim |
| 2010/0026451 A1 | 2/2010 | Erhart et al. |
| 2010/0026453 A1 | 2/2010 | Yamamoto et al. |
| 2010/0030921 A1 | 2/2010 | Kim |
| 2010/0045705 A1 | 2/2010 | Vertegaal et al. |
| 2010/0050175 A1 | 2/2010 | Jung et al. |
| 2010/0059295 A1 | 3/2010 | Hotelling et al. |
| 2010/0073301 A1 | 3/2010 | Yousefpor et al. |
| 2010/0083000 A1 | 4/2010 | Kesanupalli et al. |
| 2010/0085325 A1 | 4/2010 | King-Smith et al. |
| 2010/0119124 A1 | 5/2010 | Satyan |
| 2010/0123675 A1 | 5/2010 | Ippel |
| 2010/0127366 A1 | 5/2010 | Bond et al. |
| 2010/0146275 A1 | 6/2010 | Slick et al. |
| 2010/0162386 A1 | 6/2010 | Li et al. |
| 2010/0176823 A1 | 7/2010 | Thompson et al. |
| 2010/0176892 A1 | 7/2010 | Thompson et al. |
| 2010/0177940 A1 | 7/2010 | Thompson et al. |
| 2010/0180127 A1 | 7/2010 | Li et al. |
| 2010/0180136 A1 | 7/2010 | Thompson et al. |
| 2010/0189314 A1 | 7/2010 | Benkley et al. |
| 2010/0191634 A1 | 7/2010 | Macy et al. |
| 2010/0193257 A1 | 8/2010 | Hotelling et al. |
| 2010/0208953 A1 | 8/2010 | Gardner et al. |
| 2010/0244166 A1 | 9/2010 | Shibuta et al. |
| 2010/0245553 A1 | 9/2010 | Schuler et al. |
| 2010/0272329 A1 | 10/2010 | Benkley |
| 2010/0284565 A1 | 11/2010 | Benkley et al. |
| 2010/0318515 A1 | 12/2010 | Ramanathan et al. |
| 2011/0002461 A1 | 1/2011 | Erhart et al. |
| 2011/0018556 A1 | 1/2011 | Le et al. |
| 2011/0060913 A1 | 3/2011 | Hird et al. |
| 2011/0074734 A1 | 3/2011 | Wassvik et al. |
| 2011/0080370 A1 | 4/2011 | Wu |
| 2011/0082791 A1 | 4/2011 | Baghdasaryan et al. |
| 2011/0082800 A1 | 4/2011 | Baghdasaryan et al. |
| 2011/0082801 A1 | 4/2011 | Baghdasaryan et al. |
| 2011/0082802 A1 | 4/2011 | Baghdasaryan et al. |
| 2011/0083018 A1 | 4/2011 | Kesanupalli et al. |
| 2011/0083170 A1 | 4/2011 | Kesanupalli et al. |
| 2011/0083173 A1 | 4/2011 | Baghdasaryan et al. |
| 2011/0102567 A1 | 5/2011 | Erhart et al. |
| 2011/0102569 A1 | 5/2011 | Erhart et al. |
| 2011/0138450 A1 | 6/2011 | Kesanupalli et al. |
| 2011/0175703 A1 | 7/2011 | Benkley |
| 2011/0176037 A1 | 7/2011 | Benkley |
| 2011/0182486 A1 | 7/2011 | Valfridsson et al. |
| 2011/0193799 A1 | 8/2011 | Jung et al. |
| 2011/0214924 A1 | 9/2011 | Perezselsky et al. |
| 2011/0215150 A1 | 9/2011 | Schneider |
| 2011/0242021 A1 | 10/2011 | Jung et al. |
| 2011/0248941 A1 | 10/2011 | Abdo et al. |
| 2011/0261003 A1 | 10/2011 | Lee et al. |
| 2011/0267298 A1 | 11/2011 | Erhart et al. |
| 2011/0285640 A1 | 11/2011 | Park et al. |
| 2011/0298711 A1 | 12/2011 | Dean et al. |
| 2011/0304001 A1 | 12/2011 | Erhart et al. |
| 2012/0012652 A1 | 1/2012 | Couper et al. |
| 2012/0014206 A1 | 1/2012 | Yoshida et al. |
| 2012/0044639 A1 | 2/2012 | Garcia |
| 2012/0069042 A1 | 3/2012 | Ogila et al. |
| 2012/0189166 A1 | 7/2012 | Russo |
| 2012/0189172 A1 | 7/2012 | Russo |
| 2013/0106759 A1 | 5/2013 | Fredriksen et al. |
| 2013/0135247 A1 | 5/2013 | Na et al. |
| 2013/0181911 A1 | 7/2013 | Yilmaz et al. |
| 2013/0265137 A1 | 10/2013 | Nelson et al. |
| 2015/0030217 A1 | 1/2015 | Wickboldt et al. |

FOREIGN PATENT DOCUMENTS

| | | |
|---|---|---|
| CN | 1760891 A | 4/2006 |
| CN | 1841280 A | 10/2006 |
| CN | 1889103 A | 1/2007 |
| CN | 1942853 A | 4/2007 |
| CN | 1010464458 A | 10/2007 |
| CN | 101383704 A | 3/2009 |
| CN | 101515214 A | 8/2009 |
| CN | 101582002 A | 11/2009 |
| CN | 201936289 U | 8/2011 |
| DE | 2213813 | 10/1973 |
| DE | 3216389 A1 | 11/1983 |
| DE | 19606408 | 8/1997 |
| DE | 102005051530 A1 | 5/2007 |
| EP | 0929028 | 1/1998 |
| EP | 0905646 | 3/1999 |
| EP | 0973123 | 1/2000 |
| EP | 1018697 | 7/2000 |
| EP | 1 113 383 | 4/2001 |
| EP | 1 113 405 | 4/2001 |
| EP | 1139301 | 10/2001 |
| EP | 1148446 A2 | 10/2001 |
| EP | 1 289 239 | 5/2003 |
| EP | 1531419 | 5/2005 |
| EP | 1533759 | 5/2005 |
| EP | 1538548 | 6/2005 |
| EP | 1624399 | 2/2006 |
| EP | 1939788 | 7/2008 |
| EP | 2343677 | 7/2011 |
| EP | 2343679 | 7/2011 |
| EP | 2348472 | 7/2011 |
| FR | 2839173 | 3/2003 |
| GB | 2331613 | 5/1999 |
| GB | 2480919 | 12/2011 |
| JP | 62-226030 A | 10/1987 |
| JP | 04158434 | 6/1992 |
| JP | 10-020992 A | 1/1998 |
| JP | 11-164824 A | 6/1999 |
| JP | 2000-057328 A | 2/2000 |
| JP | 2001-077342 A | 3/2001 |
| JP | 2003-511799 A | 3/2003 |
| JP | 2006-271028 | 3/2005 |
| JP | 2005242856 | 9/2005 |
| JP | 2006-184104 A | 7/2006 |
| JP | 2006-517023 A | 7/2006 |
| JP | 2007-010338 A | 1/2007 |
| JP | 2007-018168 A | 1/2007 |
| JP | 2008-134836 A | 6/2008 |
| JP | 2009-516295 A1 | 4/2009 |
| JP | 09071135 | 4/2009 |
| JP | 2011022788 A | 2/2011 |
| JP | 2011059793 A | 3/2011 |
| TW | 201112068 A | 4/2011 |
| TW | 201120507 A | 6/2011 |
| WO | WO 90/03620 | 4/1990 |
| WO | WO 98/15225 | 4/1998 |
| WO | WO 98/52145 | 11/1998 |
| WO | WO 98/52146 | 11/1998 |
| WO | WO 98/52147 | 11/1998 |
| WO | WO 98/52157 | 11/1998 |
| WO | WO 98/58342 | 12/1998 |
| WO | WO 99/28701 | 6/1999 |
| WO | WO 99/28701 A1 | 6/1999 |
| WO | WO 99/43258 | 9/1999 |

(56) References Cited

FOREIGN PATENT DOCUMENTS

| | | |
|---|---|---|
| WO | WO 00/68873 | 11/2000 |
| WO | WO 00/68874 | 11/2000 |
| WO | WO 00/72507 | 11/2000 |
| WO | WO 01/09819 | 2/2001 |
| WO | WO 01/09936 | 2/2001 |
| WO | WO 01/22349 | 3/2001 |
| WO | WO 01/27868 A1 | 4/2001 |
| WO | WO 01/29731 | 4/2001 |
| WO | WO 01/39134 | 5/2001 |
| WO | WO 01/94966 | 6/2001 |
| WO | WO 01/65470 | 9/2001 |
| WO | WO 01/73678 | 10/2001 |
| WO | WO 01/77994 | 10/2001 |
| WO | WO 01/80166 | 10/2001 |
| WO | WO 01/94892 | 12/2001 |
| WO | WO 01/94902 | 12/2001 |
| WO | WO 01/95304 | 12/2001 |
| WO | WO 01/95305 | 12/2001 |
| WO | WO 01/99036 | 12/2001 |
| WO | WO 01/99305 | 12/2001 |
| WO | WO 02/11066 | 2/2002 |
| WO | WO 02/15209 | 2/2002 |
| WO | WO 02/15267 | 2/2002 |
| WO | WO 02/44998 | 6/2002 |
| WO | WO 02/47018 | 6/2002 |
| WO | WO 02/61668 | 8/2002 |
| WO | WO 02/069386 | 9/2002 |
| WO | WO 02/071313 | 9/2002 |
| WO | WO 02/073375 | 9/2002 |
| WO | WO 02/077907 | 10/2002 |
| WO | WO 02/086800 | 10/2002 |
| WO | WO 02/093462 | 10/2002 |
| WO | WO 02/095349 | 11/2002 |
| WO | WO 03/007127 | 1/2003 |
| WO | WO 03/017211 | 2/2003 |
| WO | WO 03/049011 | 6/2003 |
| WO | WO 03/049012 | 6/2003 |
| WO | WO 03/049016 | 6/2003 |
| WO | WO 03/049104 | 6/2003 |
| WO | WO 03/063054 | 7/2003 |
| WO | WO 03/075210 | 9/2003 |
| WO | WO 03/075210 | 12/2003 |
| WO | WO 2004/066194 | 8/2004 |
| WO | WO 2004/066693 | 8/2004 |
| WO | WO 2005/104012 | 11/2005 |
| WO | WO 2005/106774 | 11/2005 |
| WO | WO 2006/040724 | 4/2006 |
| WO | WO 2006/041780 | 4/2006 |
| WO | WO 2007/011607 | 1/2007 |
| WO | 2007048395 A1 | 5/2007 |
| WO | WO 2007/058727 A1 | 5/2007 |
| WO | WO 2008/033264 | 3/2008 |
| WO | WO 2008/033265 | 6/2008 |
| WO | WO 2008/137287 | 11/2008 |
| WO | WO 2009/002599 | 12/2008 |
| WO | WO 2009/029257 | 6/2009 |
| WO | WO 2009/079219 | 6/2009 |
| WO | WO 2009/079221 | 6/2009 |
| WO | WO 2009/079262 | 6/2009 |
| WO | WO 2010/034036 | 3/2010 |
| WO | WO 2010/036445 | 4/2010 |
| WO | WO 2010/143597 | 12/2010 |
| WO | 2011035491 A1 | 3/2011 |
| WO | WO 2011/053797 | 5/2011 |
| WO | WO 2011088252 A1 | 7/2011 |
| WO | 2012014206 A2 | 2/2012 |

OTHER PUBLICATIONS

U.S. Appl. No. 12/820,100, Notice of Allowance dated Jun. 5, 2014, filed Jun. 21, 2010, Inventor: Fred G. Benkley, III, 41 pages.
Pandya, et al.; Coral: Miniature Acoustic Communication Subsystem Architecture for Underwater Wireless Sensor Networks; University of Illinois at Urbana-Champaign Micro and Nanotechnology Laboratory Urbana, IL; Sensors, 2005 IEEE, vol., No., pp. 4, Oct. 30, 2005-Nov. 3, 2005.
Saunvit Panda, et al. "Coral Miniature Acoustic Communication Subsystem Architecture for Underwater Wireless Sensor Networks," Sensors, 2005 IEEE, Conference in Irvine California, 5 pages (Oct. 30, 2005-Nov. 3, 2005), 2005.
Jacob O. Wobbrock, et al. "Text Entry from Power Wheelchairs: EdgeWrite for Joysticks and Touchpads," ASSETS'04, Atlanta, Georgia, 8 pages (Oct. 18-20, 2004), 2004.
Biometrics, "A Responsive Supply Chain", By Andrew Conry-Murray, 5 pages, posted Jul. 7, 2002, as printed Aug. 23, 2004, at http://www.networkmagazine.com/shared/article/ ID-17601104.
Ballard and Brown, "Computer Vision", Prentice Hall, 1982, pp. 66-69.
S. Shigematsu et al., "A Single-Chip Fingerprint Sensor and Identifier", IEEE Journal of Solid-State Circuits, vol. 34, No. 12, Dec. 1999, pp. 1852-1859.
"Fingernail Touch Sensors: Spatially Distributed Measurement and Hemodynamic Modeling", Stephen Mascaro and H. Harry Asada, 2000 IEEE, pp. 3422-3427.
Bartholomew J. Kane, "A High Resolution Traction Stress Sensor Array For Use in Robotice Tactile Determination", A Dissertation Submitted to the Department of Mechanical Engineering and the Committee on Graduate Studies of Stanford University in Partial Fulfillment of the Requirements for the Degree of Doctor of Philosophy, Sep. 1999.
Choonwoo Ryu et al. "Super-template Generation Using Successive Bayesian Estimation for Fingerprint Enrollment", Jan. 2005 Springer-Verlag Berlin Heidelberg, pp. 710-719.
Dongjae Lee et al. "Fingerprint Fusion Based on Minutiae and Ridge for Enrollment", Jan. 2003 Springer-Verlag Berlin Heidelberg, pp. 478-485.
Koichi Sasakawa et al. "Personal Verification System with High Tolerance of Poor Quality Fingerprints", May 1990 Machine Vision Systems Integration in Industry, p. 265272.
Michal Irani et al. "Improving Resolution by Image Registration", May 1991 by Academic Press, Inc., pp. 231-239.
Qinfen Zheng et al. "A Computational Vision Approach to Image Registration", Aug. 1992 IEEE, pp. 193-197.
Wei-Yun Yau et al. "Fingerprint Templates Combination", Jan. 2004 Springer-Verlag Berlin Heidelberg, pp. 449-460.
Xudong Jiand et al. "Detecting the Fingerprint Minutiae by Adaptive Tracing the Gray-Level Ridge", May 2001, pp. 999-1013, Published by Elsevier Science Ltd.
Xudong Jiang et al. "Fingerprint Minutiae Matching Based on the Local and Global Structures", Sep. 2000 Ieee, pp. 1038-1041.
I-Control, PDS 3000 TM Product Brief "Mobile Finger-Based Control Sensor", 2 pages, Jul. 2003.
Search Report Mailed Sep. 26, 2002 for International Application No. PCT/US2001/46525.
Search Report Mailed Sep. 8, 2005 for International Application No. PCT/US2005/012792.
Search Report Mailed Dec. 12, 2005 for International Application No. PCT/US2005/013943.
Search Report Mailed Dec. 22, 2005 for European Application No. EP 05021634.0-2218.
Davide Maltoni, "Handbook of Fingerprint Recognition", XP002355942 Springer, New York, USA, Jun. 2003, pp. 65-69.
Vermesan et al., "A 500-dpi AC Capacitive Hybrid Flip-Chip CMOS ASIC/Sensor Module for Fingerprint, Navigation, and Pointer Detection With On-Chip Data Processing", IEEE Journal of Solid State Circuits, vol. 38, No. 12, Dec. 2003, pp. 2288-2294.
International Search Report and Written Opinion mailed Jan. 30, 2006 for Application No. PCT/US2005/035504.
Journal of Solid State Circuits, vol. 38, No. 12, Dec. 2003, pp. 2288-2294.
Matsumoto et al., Impact of Artificial "Gummy" Fingers on Fingerprint Systems, SPIE 4677 (2002), reprinted from cryptome.org.
Maltoni, "Handbook of Fingerprint Recognition", XP002355942 Springer, New York, USA, Jun. 2003 pp. 65-69.
Ratha, et al. "Adaptive Flow Orientation Based Feature Extraction in Fingerprint Images," Pattern Recognition, vol. 28 No. 11, 1657-1672, Nov. 1995.

(56) References Cited

OTHER PUBLICATIONS

Ratha, et al., "A Real Time Matching System for Large Fingerprint Databases," IEEE, Aug. 1996.
Suh, et al., "Design and Implementation of the AEGIS Single-Chip Secure Processor Using Physical Random Functions", Computer Architecture, 2005, ISCA '05, Proceedings, 32nd International Symposium, Jun. 2005 (MIT Technical Report CSAIL CSG-TR-843, 2004.
Rivest, et al., "A Method for Obtaining Digital Signatures and Public-Key Cryptosystems", Communication of the ACM, vol. 21 (2), pp. 120-126 (1978).
Hiltgen, et al., "Secure Internet Banking Authentication", IEEE Security and Privacy, IEEE Computer Society, New York, NY, US, Mar. 1, 2006, pp. 24-31, XP007908655, ISSN: 1540-7993.
Hegt, "Analysis of Current and Future Phishing Attacks on Internet Banking Services", Mater Thesis. Techische Universiteit Eindhoven—Department of Mathematics and Computer Science May 31, 2008, pp. 1-149, XP002630374, Retrieved from the Internet: URL: http://alexandria.tue.nl/extra1/afstversl/wsk-i/hegt2008.pdf [retrieved on Mar. 29, 2011] *pp. 127-134, paragraph 6.2*.
Gassend., et al., "Controlled Physical Random Funetions", In Proceedings of the 18th Annual Computer Security Conference, Las Vegas, Nevada, Dec. 12, 2002.
bellagiodesigns.com (Internet Archive Wayback Machine, www.bellagiodesigns.com date: Oct. 29, 2005).
Universiteit Eindhoven—Department of Mathematics and Computer Science May 31, 2008, pp. 1-149, XP002630374 Retrieved from the Internet: URL:http://alexandria.tue.nl/extral/afstversl/wsk-i/hgt2008.pdf [retrieved on Mar. 3, 2011] pp. 127-134, paragraph 6.2.
Wikipedia (Mar. 2003), "Integrated Circuit," http://en.wikipedia.org/wiki/integrated_circuit. Revision as of Mar. 23, 2003.
Closed Loop Systems, The Free Dictionary, http://www.thefreedictionary.com/closed-loop+system (downloaded Dec. 1, 2011).
Feedback: Electronic Engineering, Wikipedia, p. 5 http://en.wikipedia.org/wiki/Feedback#Electronic_engineering (downloaded Dec. 1, 2011).
ITD "Anti-Money Laundering", ITD, Jan. 22, 2009.
Galy et al. (Jul. 2007) "A full fingerprint verification system for a single-line sweep sensor." IEEE Sensors J., vol. 7 No. 7, pp. 1054-01065.
Notice of Rejection Grounds with English translation issued in Japanese Patent Application No. 2012-549092, 8 pages (Sep. 2, 2014).
Office Action (and English Translation) issued in Japanese Patent Application No. 2012-549090, 15 pages (Dec. 2, 2014).
Office Action issued in Chinese Patent Application No. 201180014263.2, 7 pages (Dec. 1, 2014).
Office Action issued in Chinese Patent Application No. 2011800114237.X, 9 pages (Dec. 3, 2014).
Extended European Search Report issued in European Patent Application No. 13775647.4, 7 pages (Oct. 1, 2015).
Communication, Partial European Search Report dated Nov. 9, 2015, EP Application No. 15179001.1-1972, IDEX ASA, 7 pages.
Communication, European Search Report dated Nov. 24, 2015, EP Application No. 15179015.1-1972, IDEX ASA, 7 pages.
Taiwanese Office Action (with English translation attached) dated Nov. 16, 2015, TW Application No. 100101376, 10 pages.
Final Office Action dated Nov. 18, 2015, U.S. Appl. No. 13/801,991, 12 pages.
Chinese Office Action dated Nov. 11, 2015, CN Application No. 201180014237.X, 6 pages.
Office Action issued by the State Intellectual Property Office of China in corresponding Chinese Patent application No. 201180014237.X, dated Jul. 8, 2015, 8 pages.
Office Action issued by the State Intellectual Property Office of China in corresponding Chinese Patent application No. 201180014263.2 dated Aug. 14, 2015, 9 pages.
Office Action issued by the Japanese Intellectual Property Office in corresponding application No. 2012549090, dated Jul. 21, 2015, 4 pages.
Notice of Allowance issued in U.S. Appl. No. 12/820,100, 32 pages. (Mar. 14, 2014).
Office Action issued in Chinese Patent Application No. 201180014263.2, 8 pages (Mar. 2, 2016).
Office Action issued in Chinese Patent Application No. 201180014237.X, 4 pages (Mar. 4, 2016).
Office Action issued in Chinese Patent Application No. 201180014263.2, 9 pages (Sep. 9, 2016).
Final Notice of Rejection (with English Translation) issued in Japanese Patent Application No. 2012-549090, 5 pages (Mar. 1, 2016).
Office Action issued in U.S. Appl. No. 13/801,991, 28 pages (Apr. 8, 2016).
Final Office Action issued in U.S. Appl. No. 13/801,991, 149 pages (Nov. 18, 2015).
Notice of Allowance issued in U.S. Appl. No. 13/801,991, 25 pages (Aug. 25, 2016).
Office Action (with English translation) issued in Korean Patent Application No. 10-2012-7021318, 27 pages (Oct. 21, 2016).
Office Action (with English translation) issued in Korean Patent Application No. 10-2012-7021324, 14 pages (Oct. 21, 2016).
Notice of Allowance issued in U.S. Appl. No. 13/801,991, 28 pages (Nov. 7, 2016).
Extended European Search Report issued in European Patent Application No. 11722400.3, 7 pages (Mary 28, 2017).

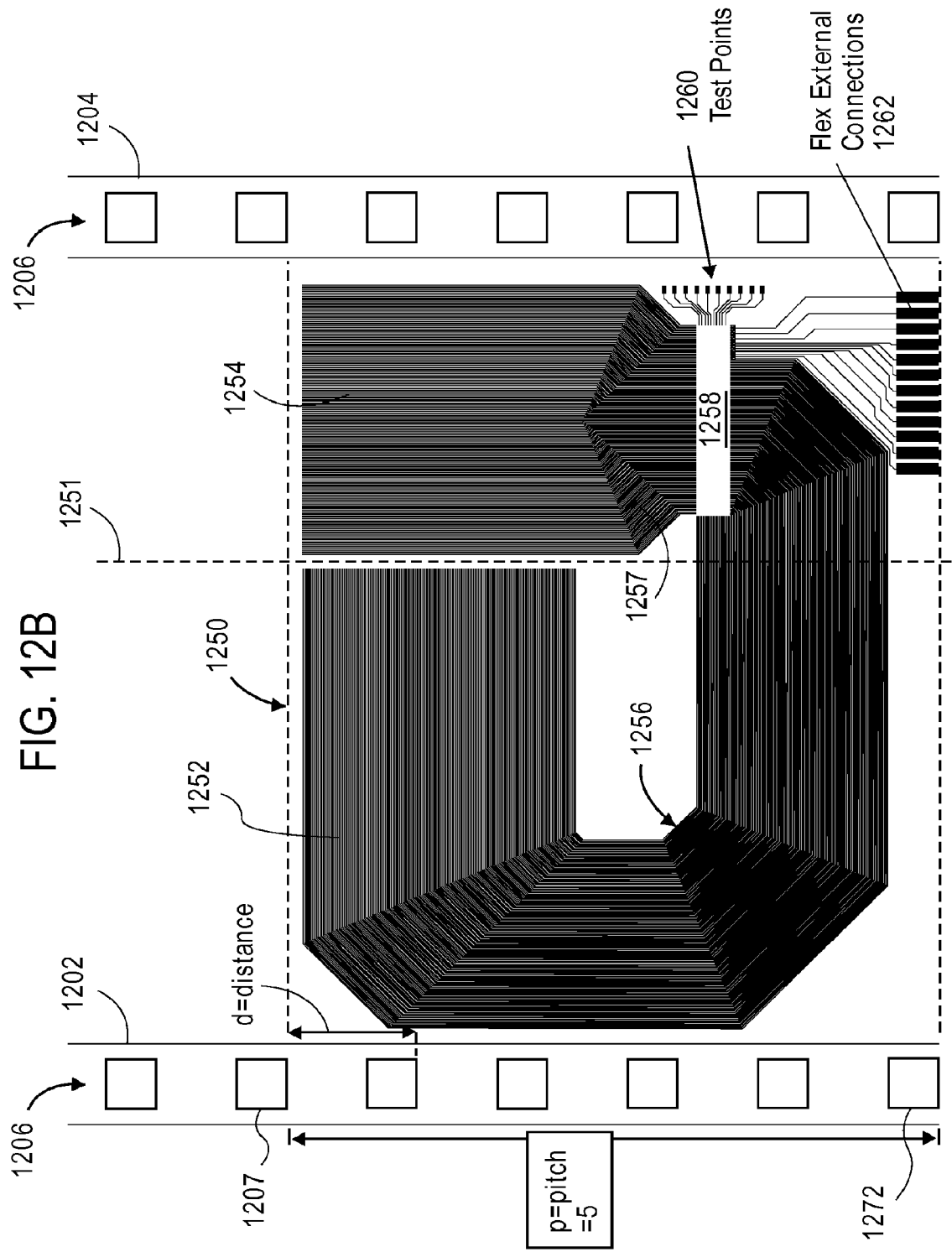

User Authentication Example

Template Extraction

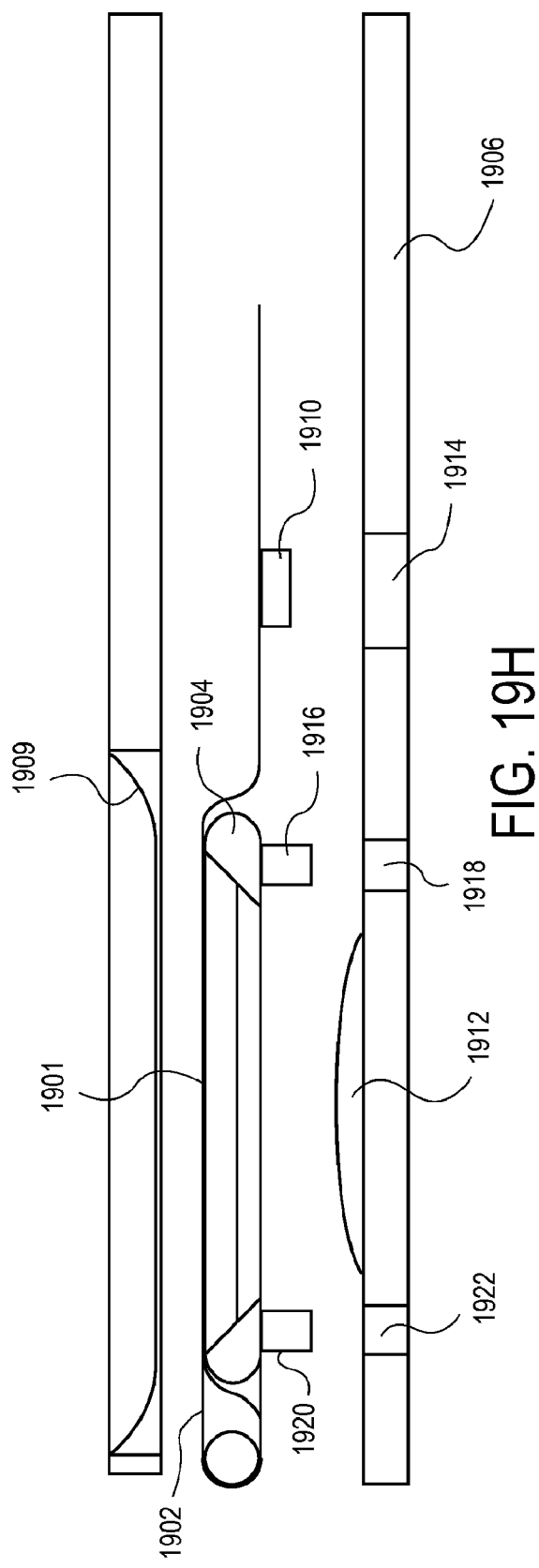
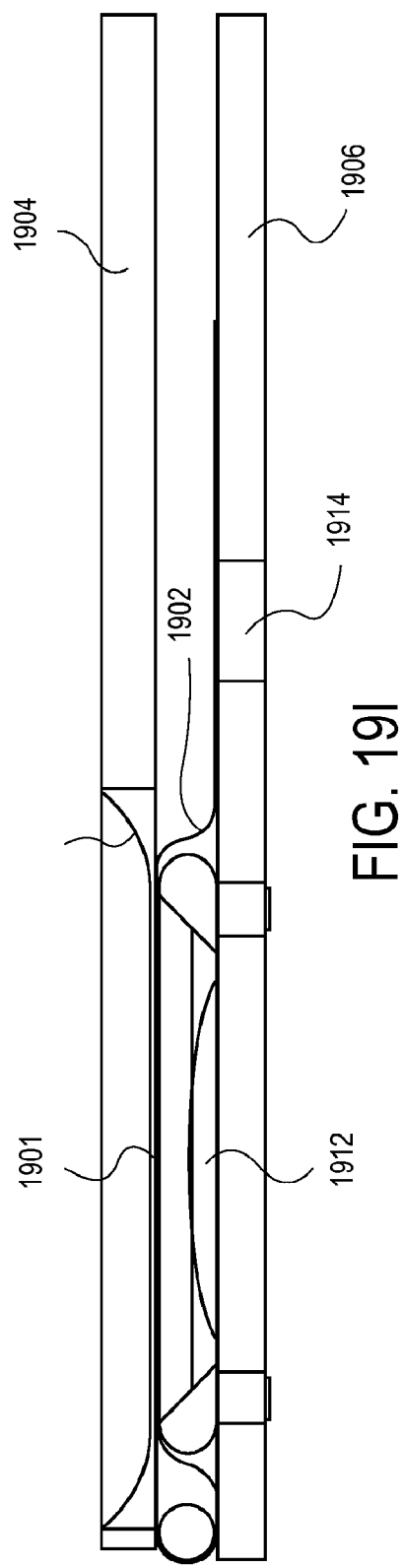
FIG. 19H
FIG. 19I

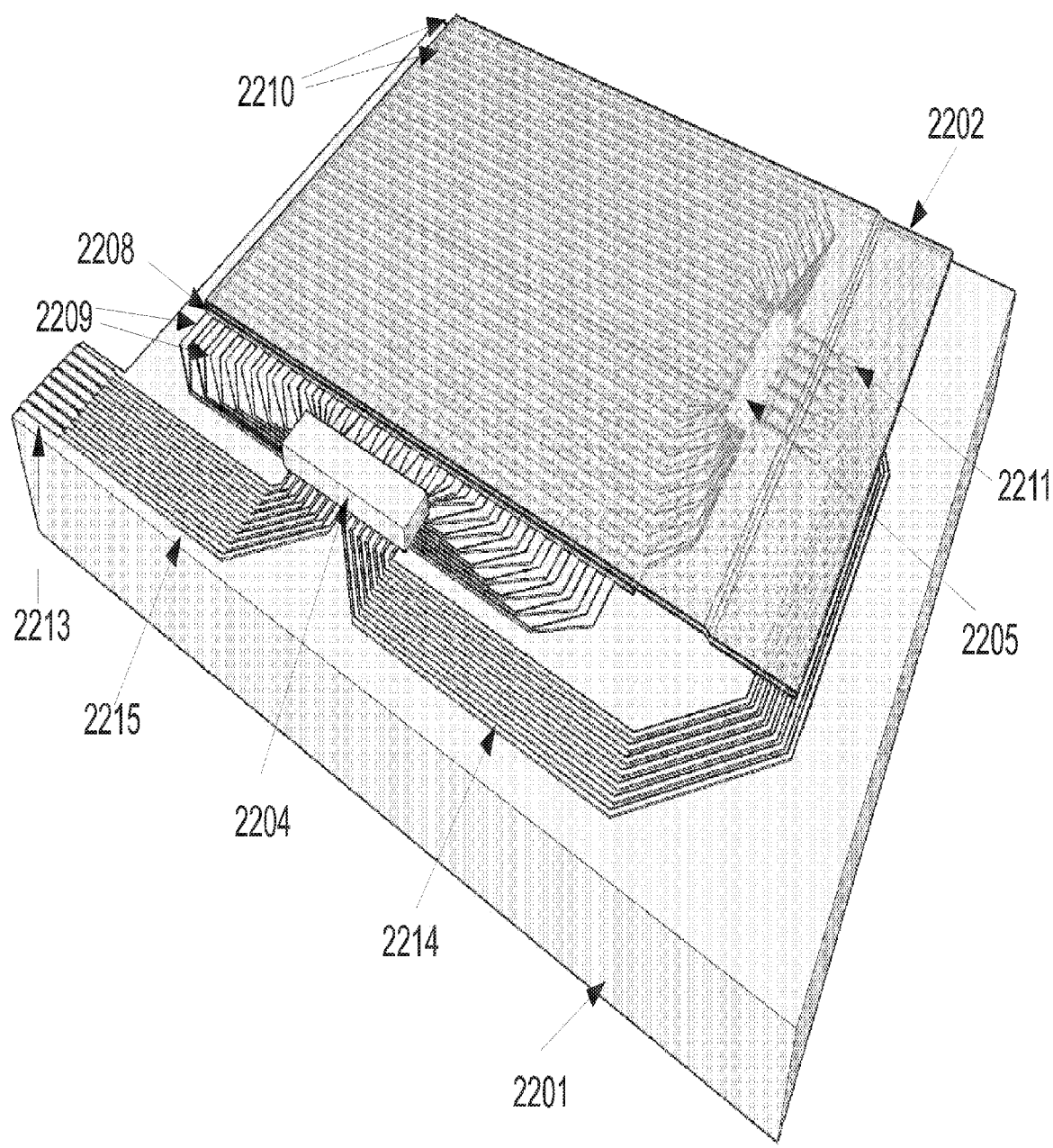
FIG. 22A - Perspective View

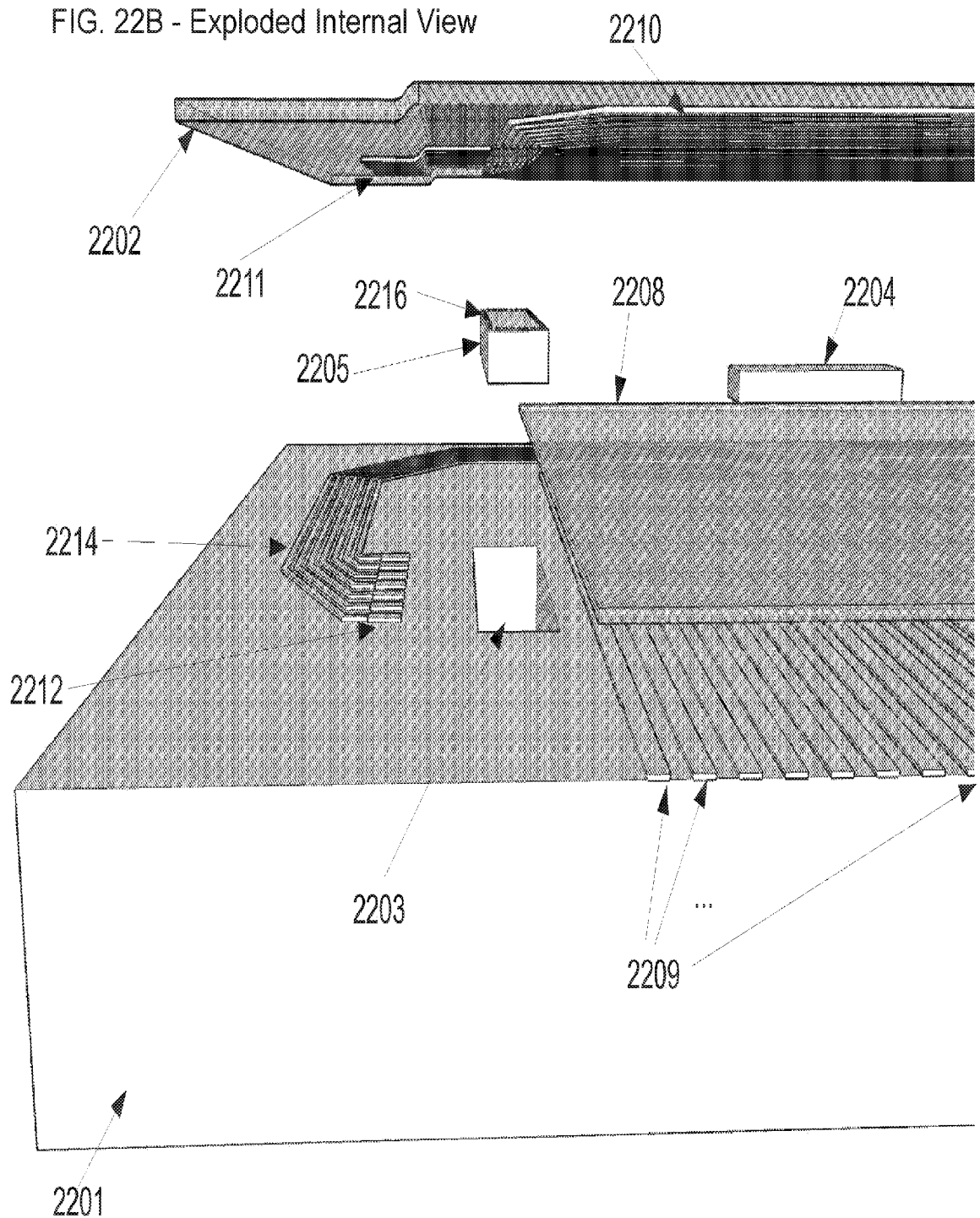
FIG. 22B - Exploded Internal View

FIG.23A- PCB Base and Drive Traces
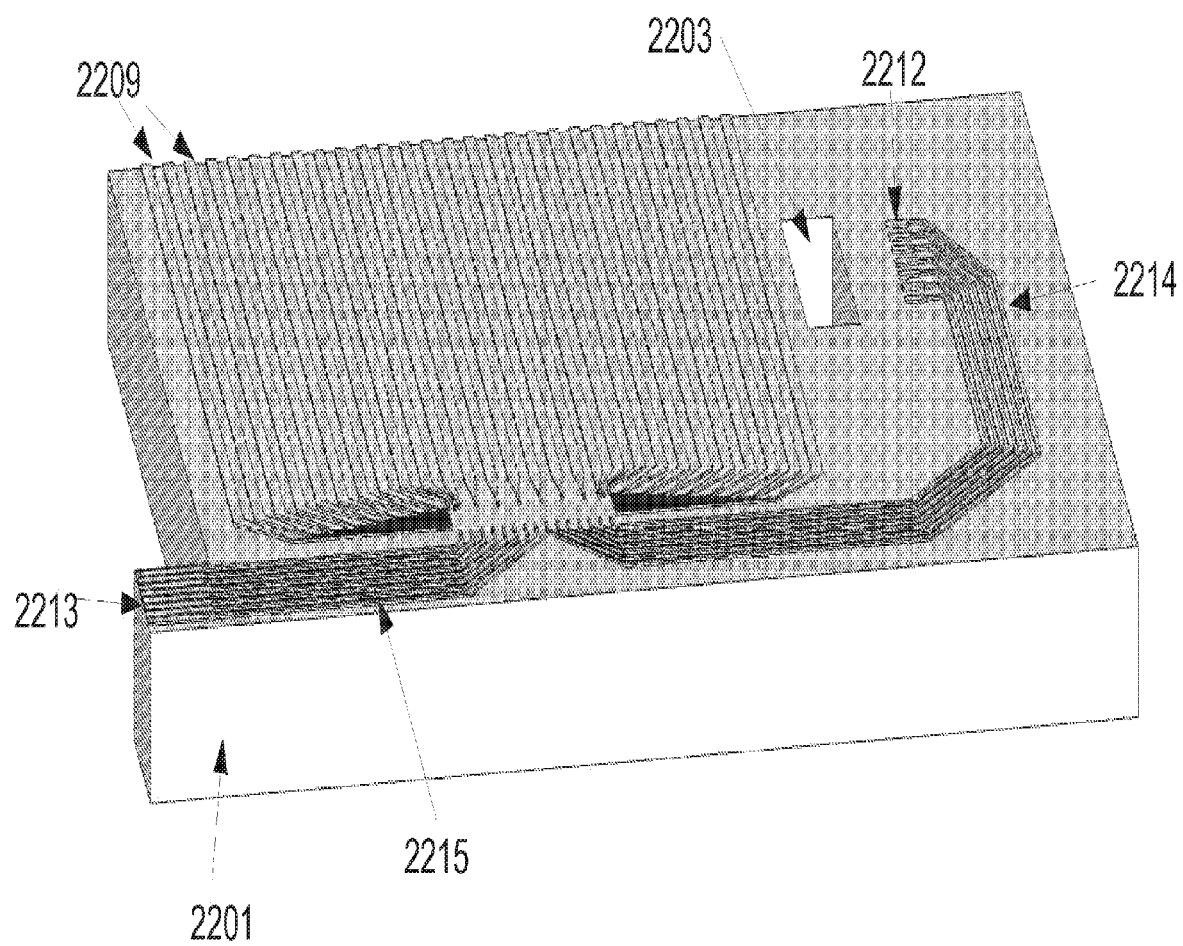

FIG. 23B- PCB with Die Mounted
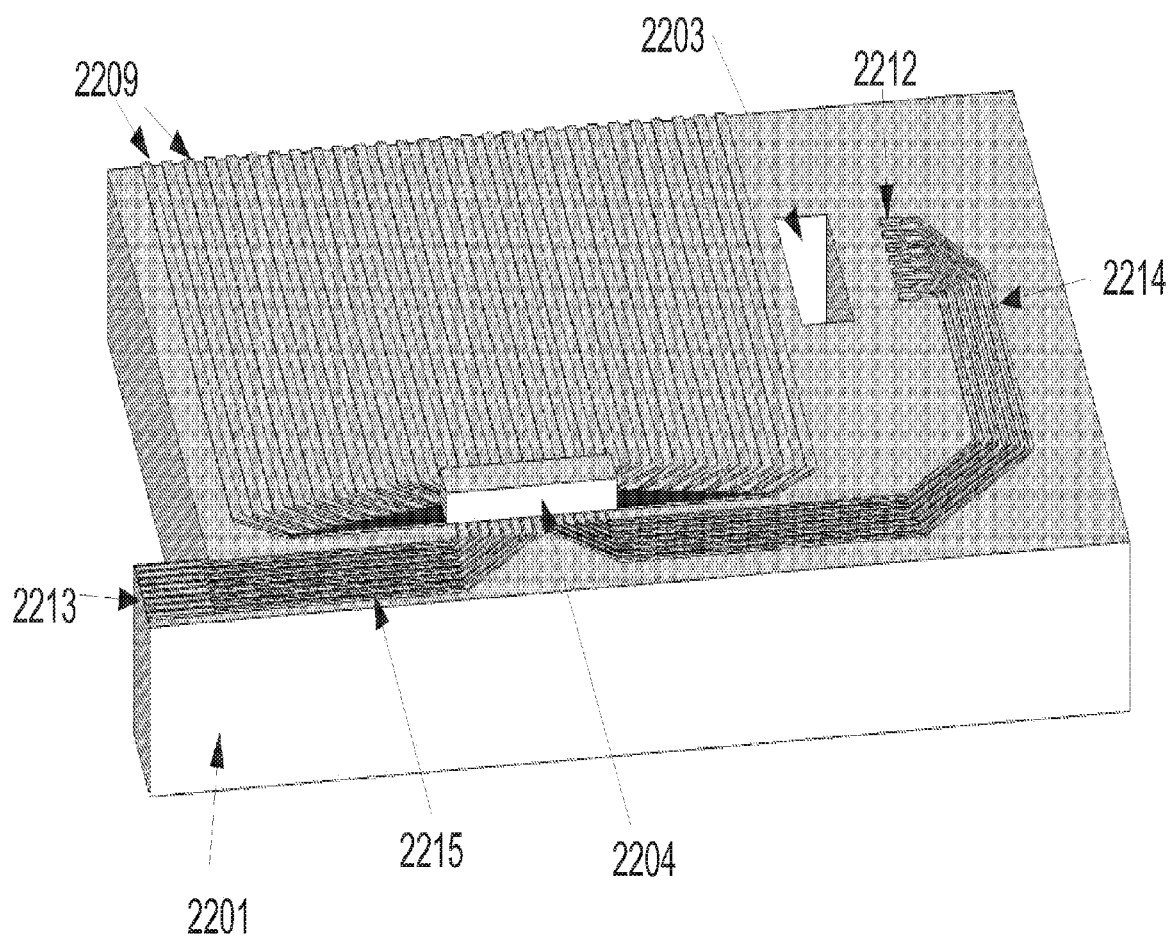

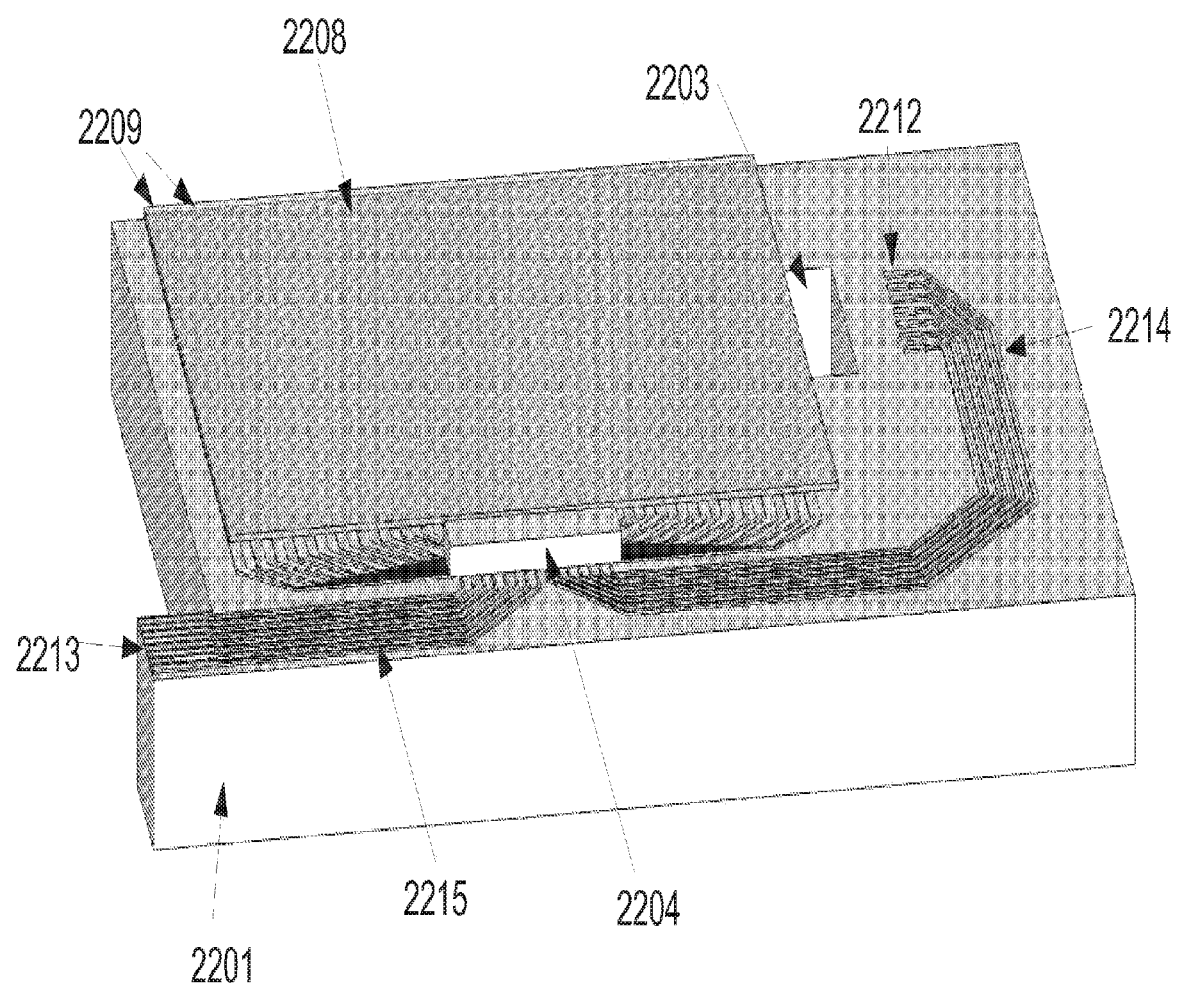
FIG. 23C- PCB Base with Die Mounted and Soldermask

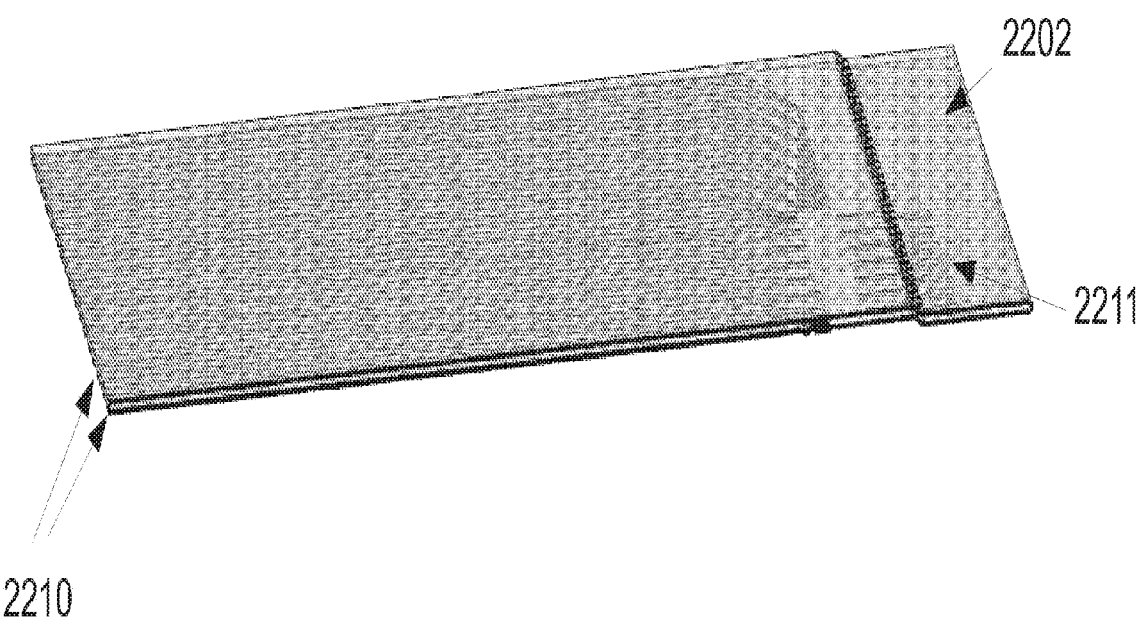
FIG. 23D- Top Flex with Pickup Traces - Cutaway View

FIG. 23E- IC COF Attach
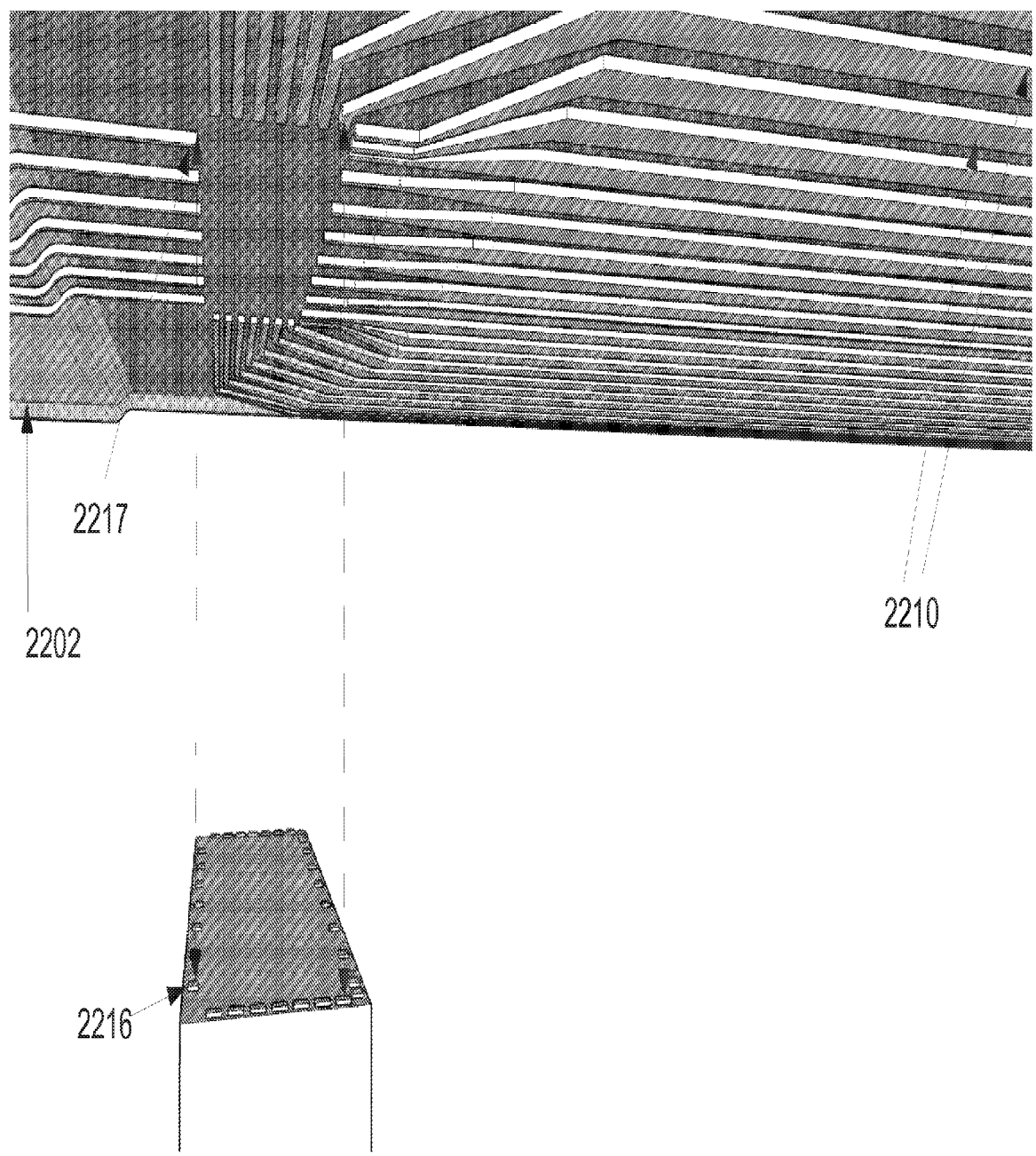

FIG. 23F- Top COF with Die Mounted - Cutaway View
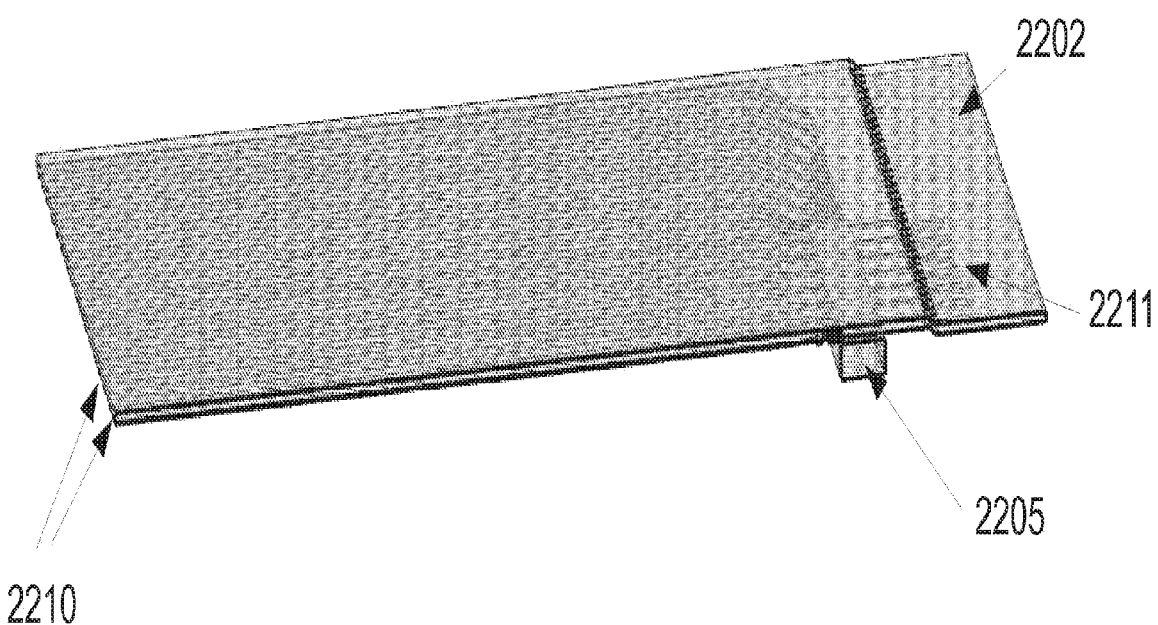

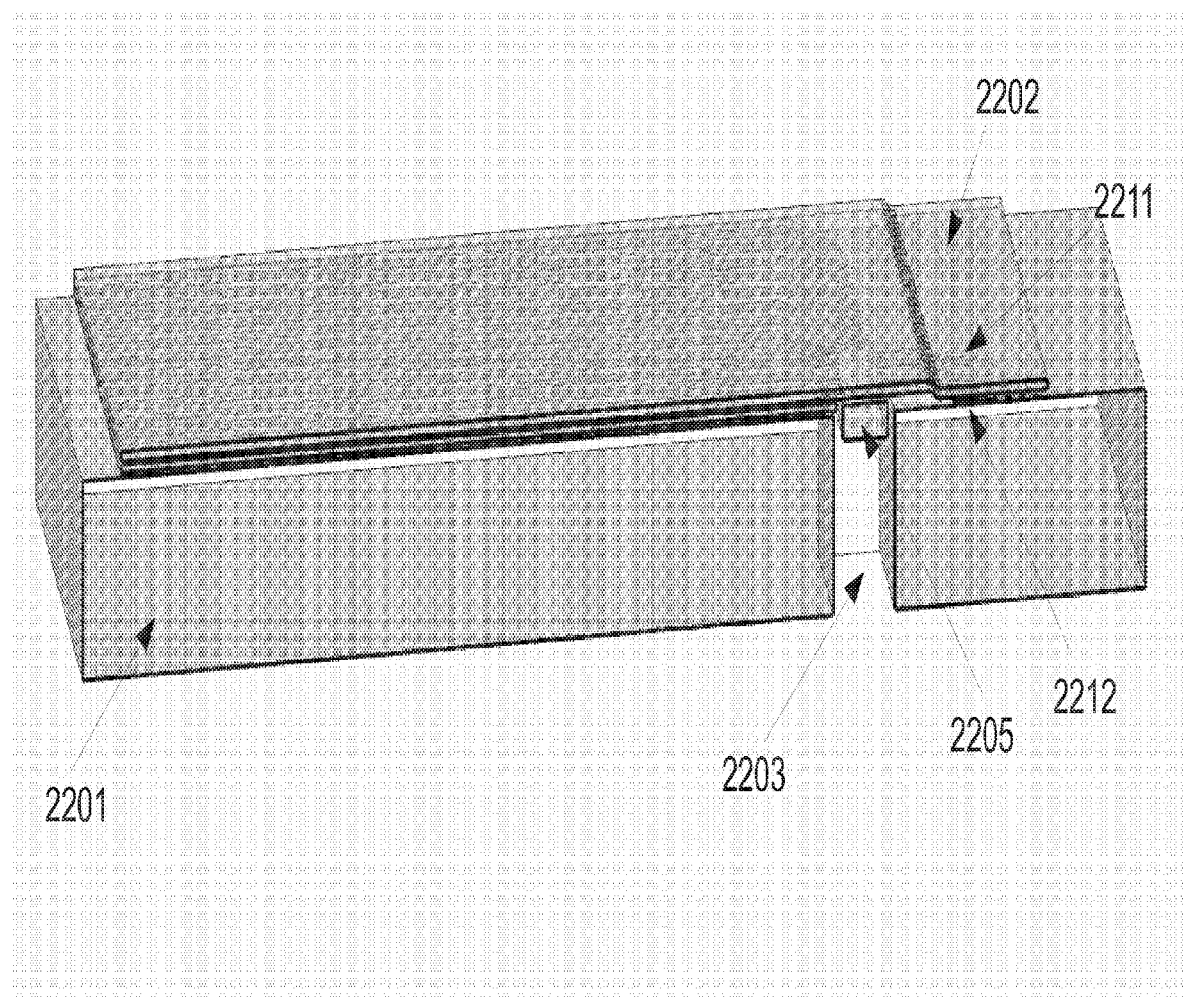
FIG. 23G- Cutaway View, Full Assembly

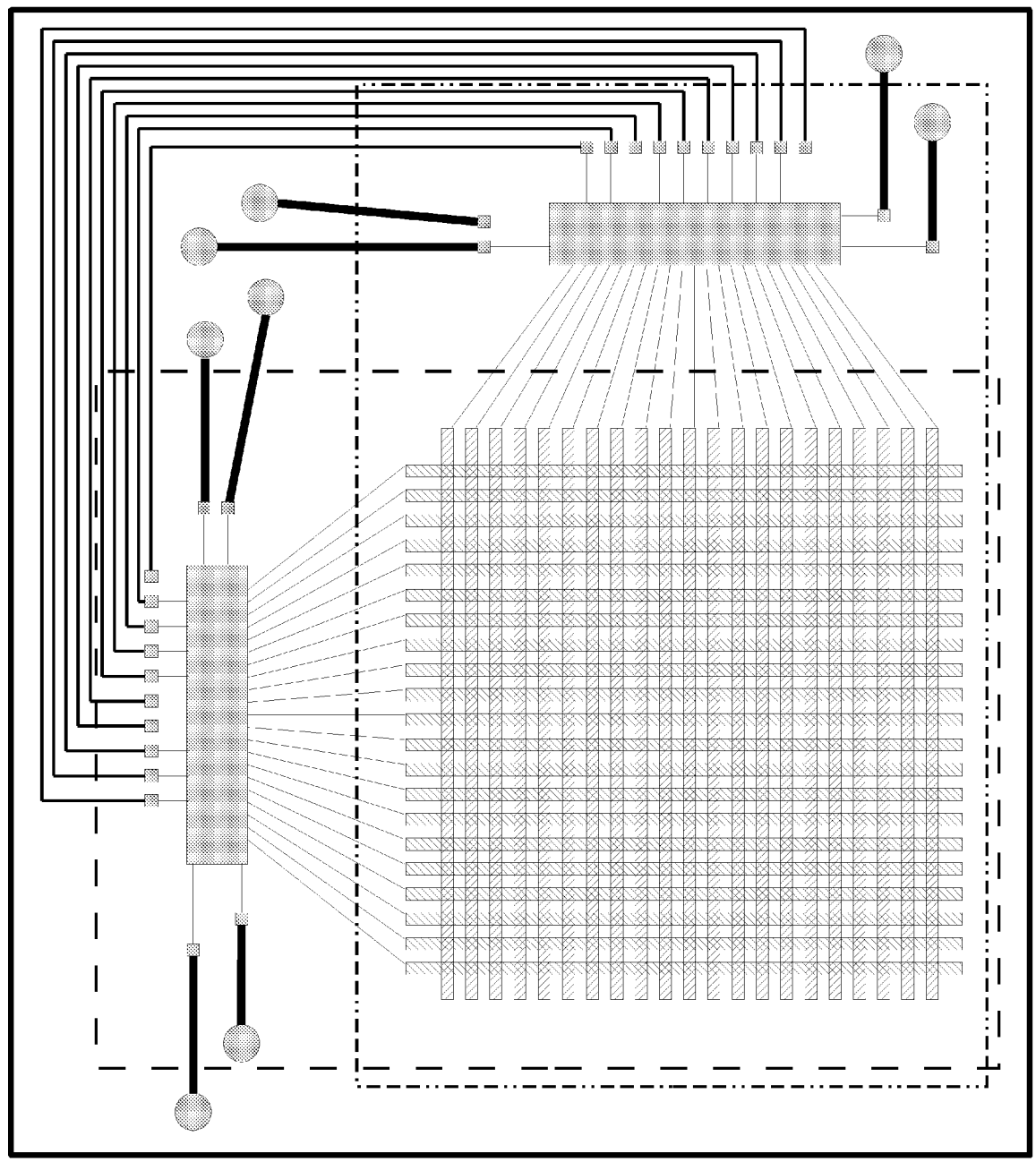
Fig 25A (Two Chip Sensor Stack-up)

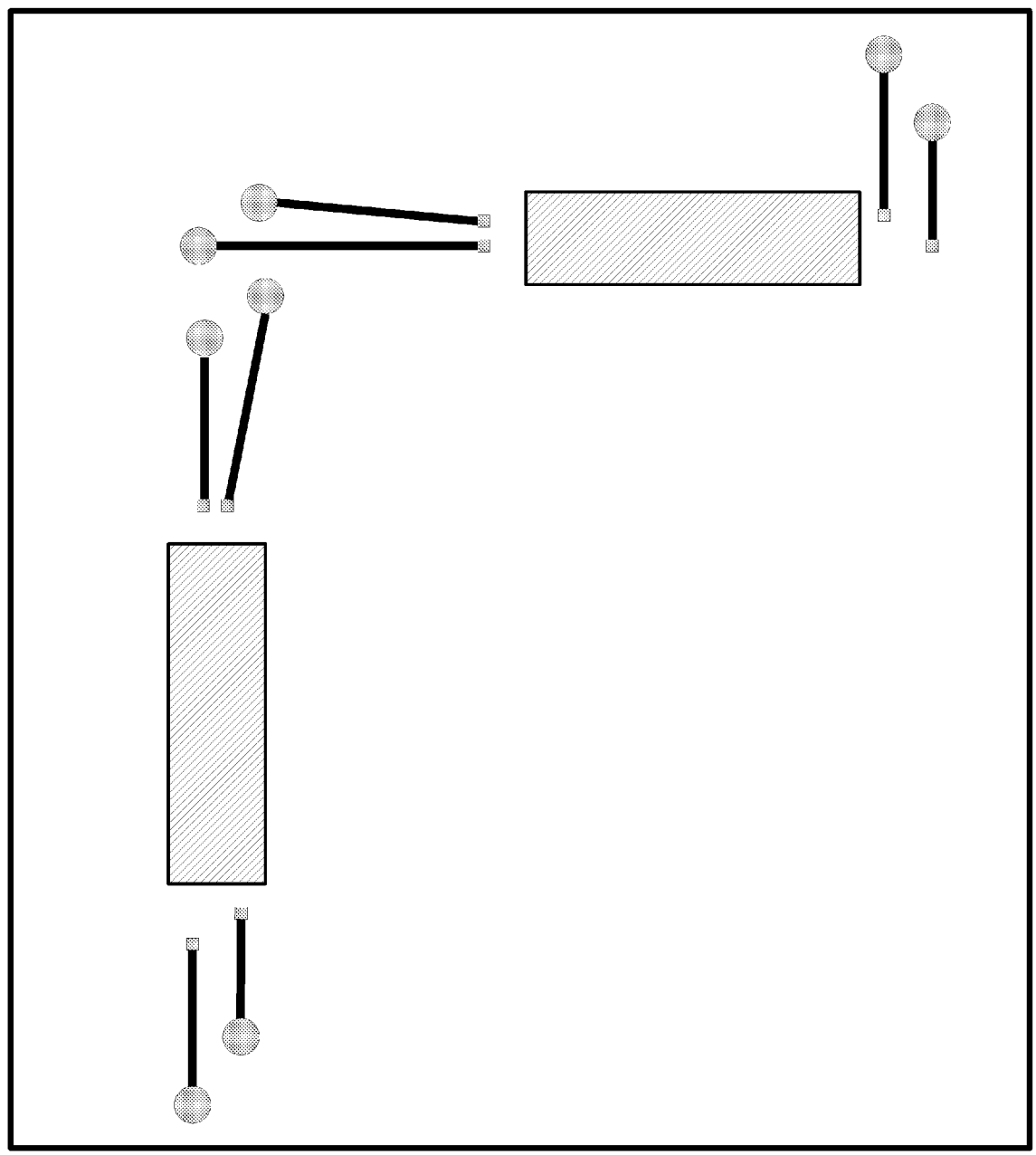
Fig 25B (Two Chip Sensor Substrate Bottom Layer)

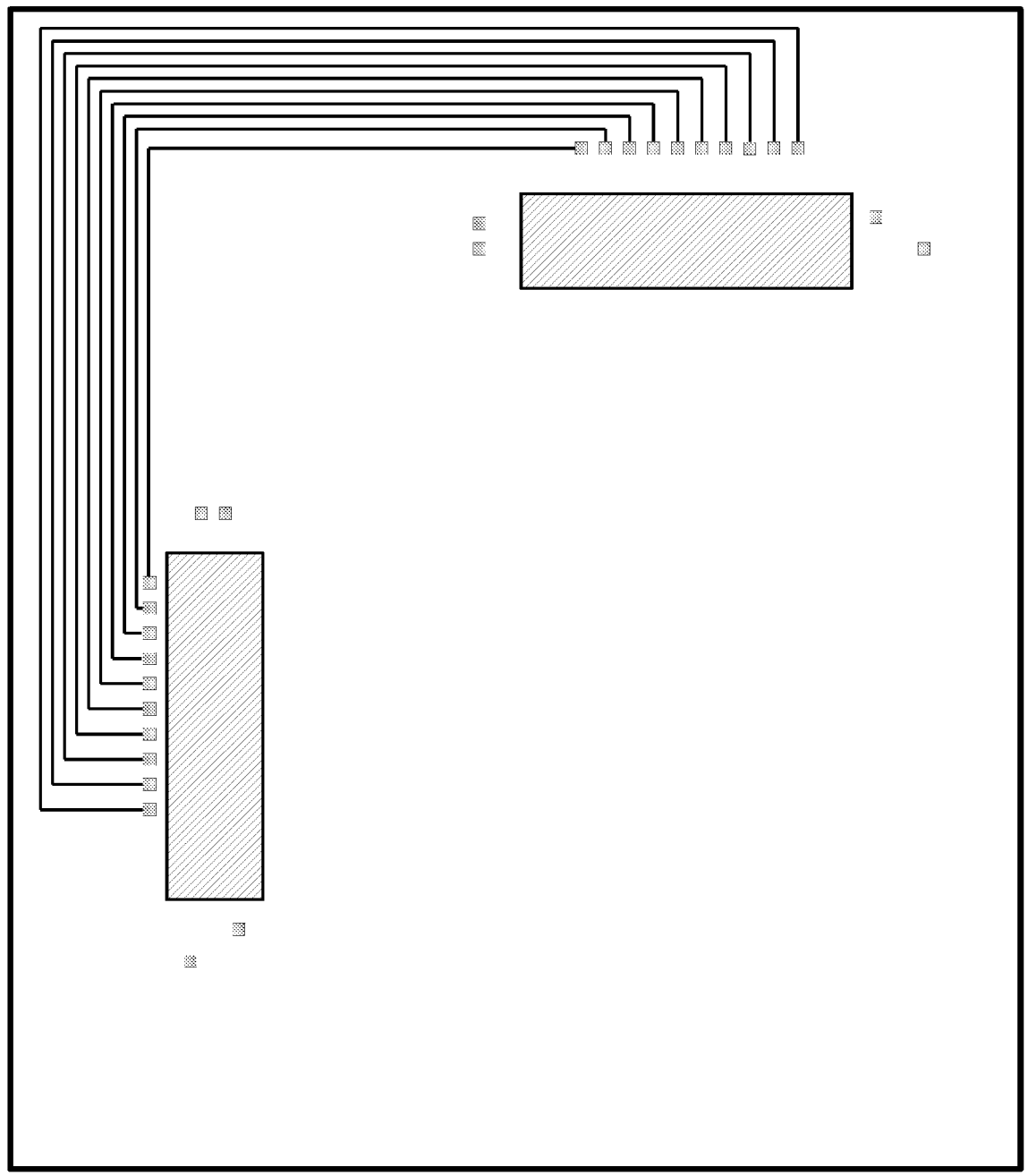
Fig 25C (Two Chip Sensor Substrate Top layer)

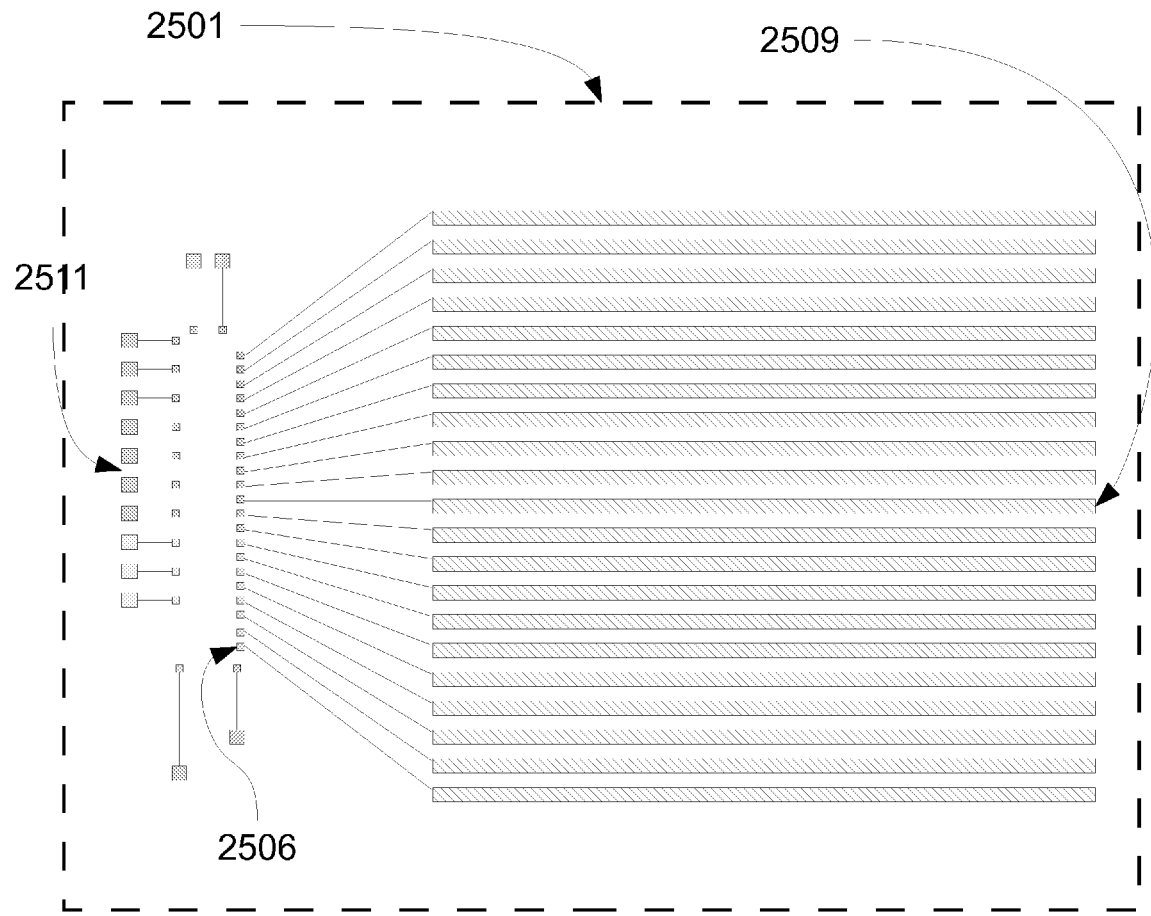
Fig 25D (Two Chip Sensor Drive Flex layer)

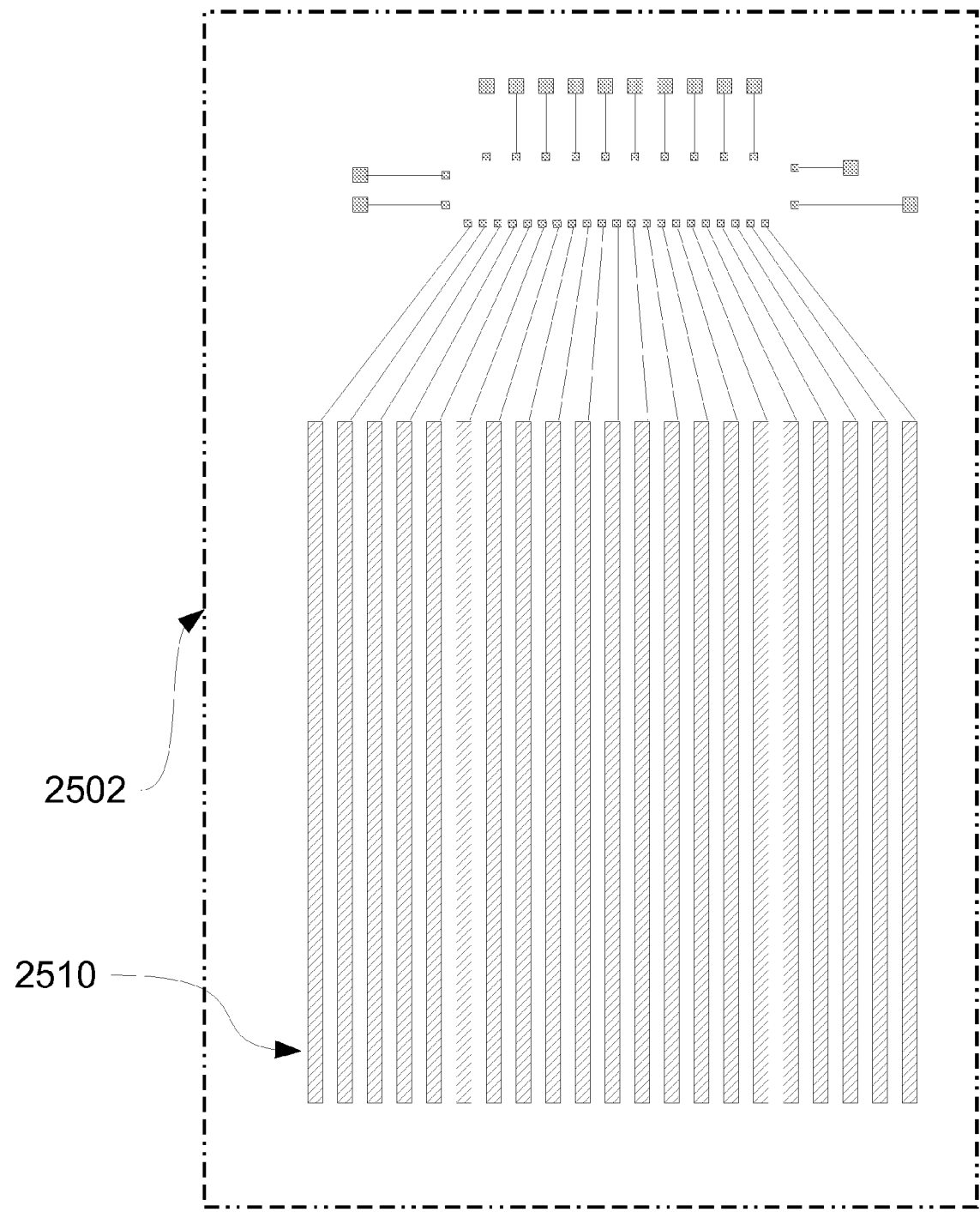
Fig 25E (Two Chip Sensor Pickup Flex Layer)

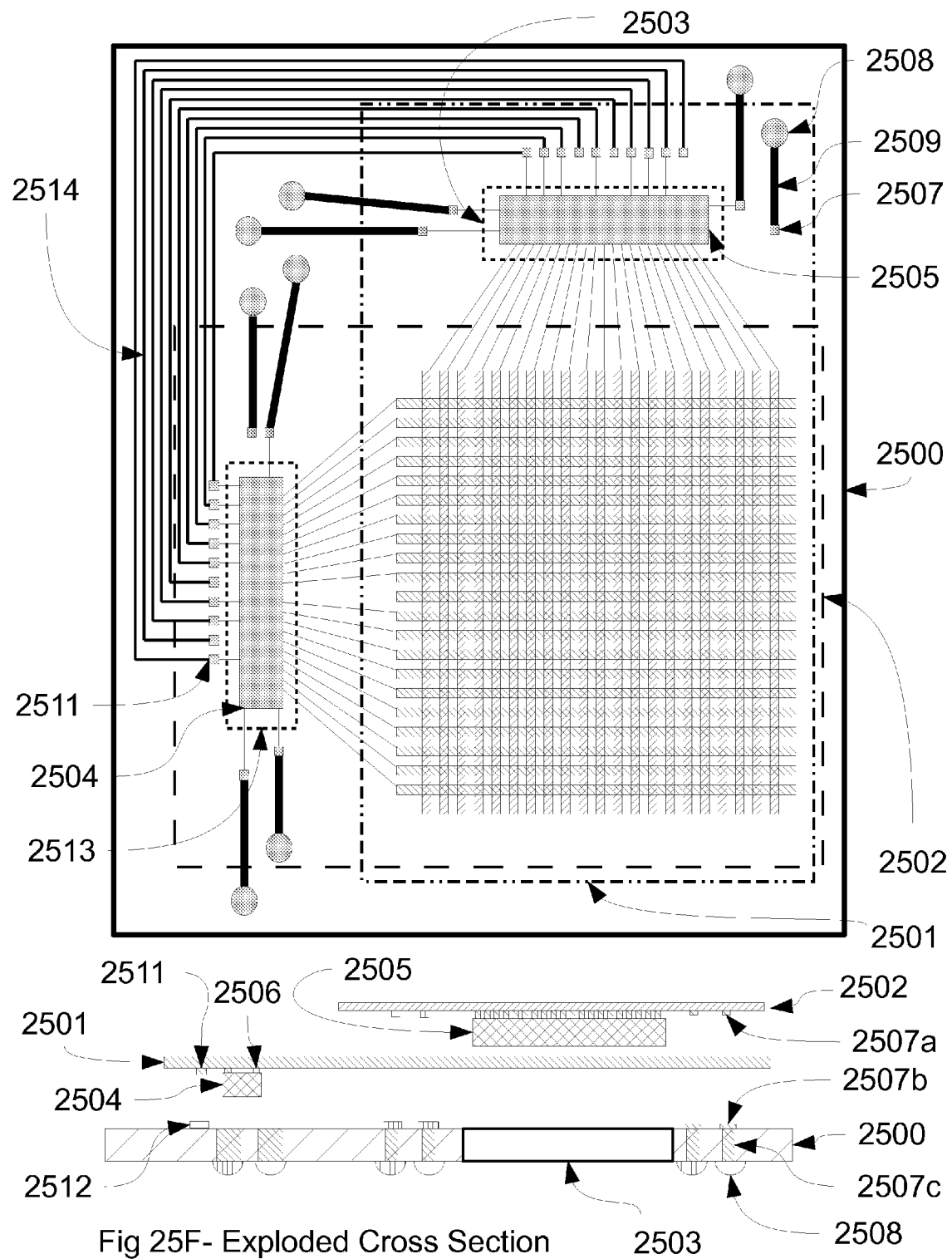
Fig 25F- Exploded Cross Section

FIG. 26A: Single Chip - Top View
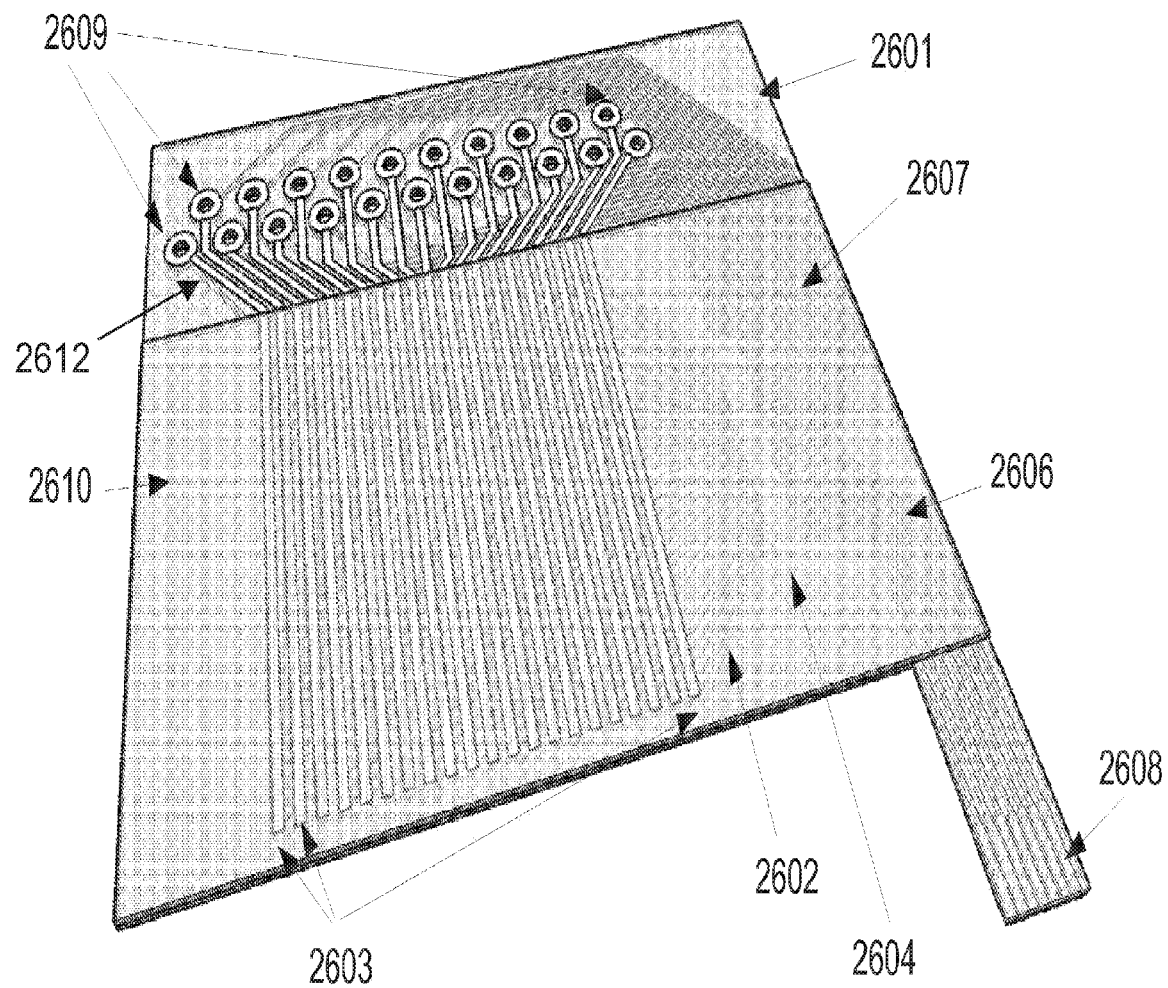

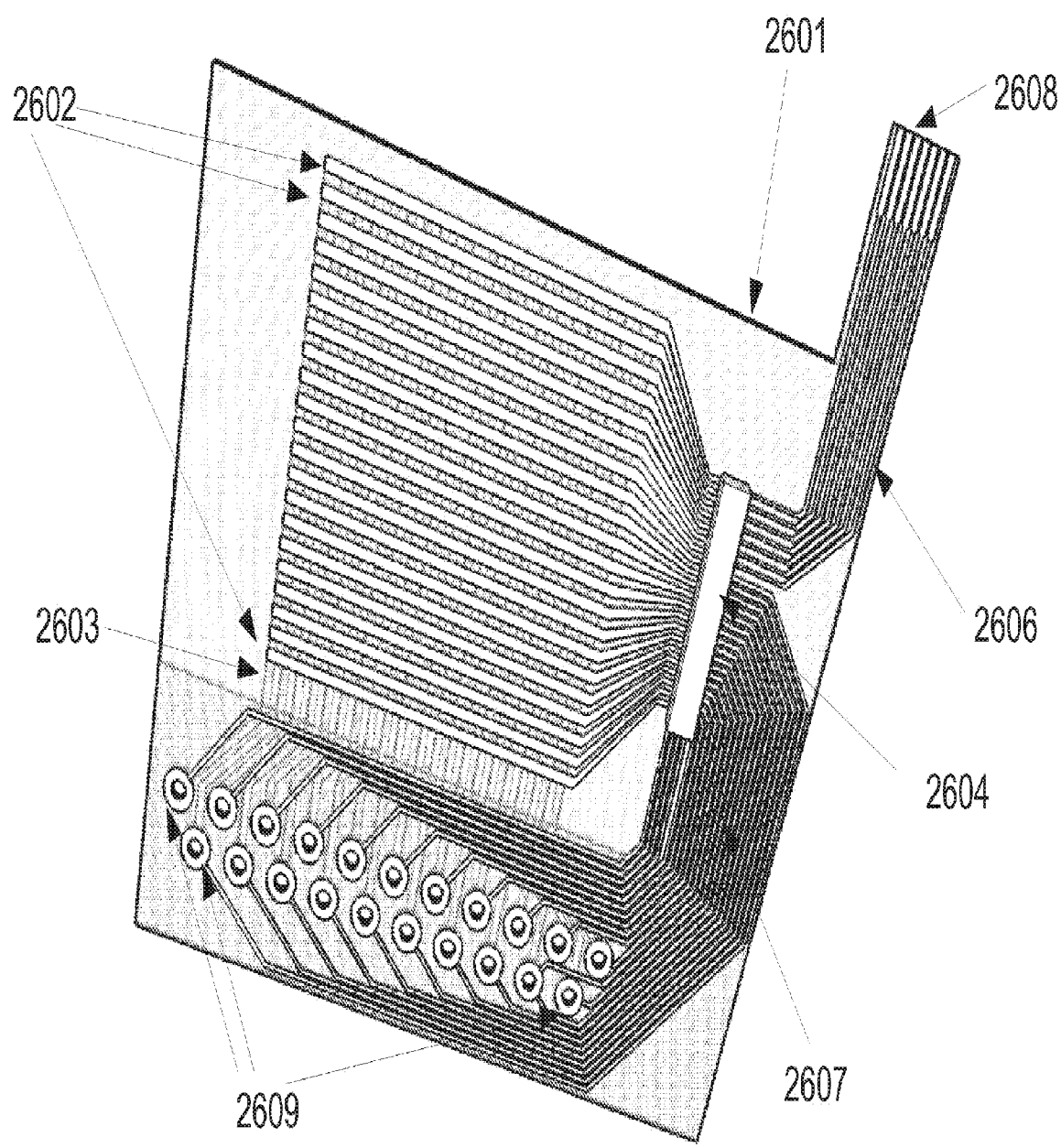
FIG. 26B: Single Chip - Bottom View

FIG. 26C - Exploded View
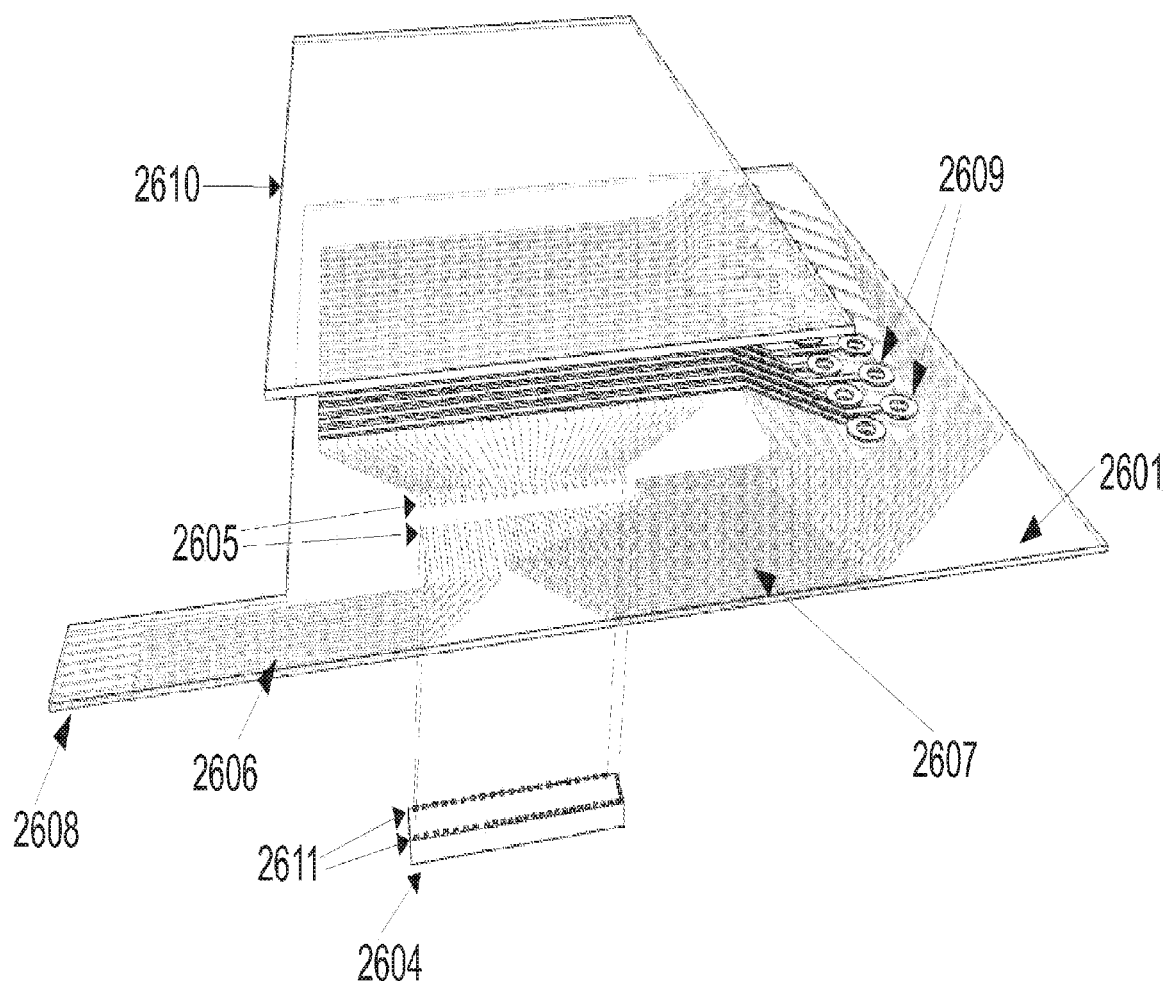

BIOMETRIC IMAGE SENSING

RELATED APPLICATIONS

This application is a Continuation of U.S. application Ser. No. 13/620,271, filed Sep. 14, 2012, now U.S. Pat.No. 9,268,988 which is a Continuation of U.S. application Ser. No. 13/118,243, filed May 27, 2011, now U.S. Pat. No. 8,866,347, which is a Continuation-in-Part of U.S. application Ser. No. 12/820,100, filed Jun. 21, 2010, now U.S. Pat. No. 8,791,792, which is a Continuation-in-Part of U.S. application Ser. No. 12/688,790, filed Jan. 15, 2010, now U.S. Pat. No. 8,421,890, the respective disclosures of which are hereby incorporated by reference.

BACKGROUND

The embodiment is generally related to electronic sensing devices, and, more particularly, to sensors for sensing objects located near or about the sensor.

In the electronic sensing market, there are a wide variety of sensors for sensing objects at a given location. Such sensors are configured to sense electronic characteristics of an object in order to sense presence of an object near or about the sensor, physical characteristics of the object, shapes, textures on surfaces of an object, material composition, biological information, and other features and characteristics of an object being sensed.

Sensors may be configured to passively detect characteristics of an object, by measuring such as temperature, weight, or various emissions such as photonic, magnetic or atomic, of an object in close proximity or contact with the sensor, or other characteristic. An example of this is a non-contact infrared thermometer that detects the black body radiation spectra emitted from an object, from which its temperature can be computed.

Other sensors work by directly exciting an object with a stimulus such as voltage or current, then using the resultant signal to determine the physical or electrical characteristics of an object. An example of this is a fluid detector consisting of two terminals, one that excites the medium with a voltage source, while the second measures the current flow to determine the presence of a conductive fluid such as water.

Since a single point measurement of an object often does not provide enough information about an object, it is often advantageous to collect a two-dimensional array of measurements. A two dimensional array of impedance may be created by moving a line sensing array over the surface of an object and then doing a line by line reconstruction of a two dimensional image like a fax machine does. An example of this is a swiped capacitive fingerprint sensor that measures differences in capacitance between fingerprint ridges and valleys as a finger is dragged across it. Such sensors reconstruct a two dimensional fingerprint image after the fact using individual line information.

A simpler way to obtain a two dimensional image is to create a two dimensional sensing array. Such sensors however can be prohibitive in cost due to the large number of sensing points needed in the array. An example of this is a two dimensional capacitive fingerprint sensor. A number of these are currently manufactured but use 150 mm.sup.2 or more of silicon area and are therefore cost prohibitive for many applications.

These different types of electronic sensors have been used in various applications, such as biometric sensors for measuring biological features and characteristics of people such as fingerprints, medical applications such as medical monitoring devices, fluid measuring monitors, and many other sensor applications. Typically, the sensing elements of the various devices are connected to a processor configured to process object information and to enable interpretations for object features and characteristics.

There are many applications for two dimensional image sensors as a particular example, and innovators have struggled with state of the art technology that has come short of desired features and functions. Fingerprint sensors, for example, have been in existence for many years and used in many environments to verify identification, to provide access to restricted areas and information, and many other uses. In this patent application, different types of fingerprint sensors will be highlighted as examples of sensor applications where the embodiment is applicable for simplicity of explanations, but other types of applications are also relevant to this background discussion and will also be addressed by the detailed description of the embodiment. These placement sensors may be configured to sense objects placed near or about the sensor, such as a fingerprint placement sensor that is configured to capture a full image of a fingerprint from a user's finger and compare the captured image with a stored image for authentication. Alternatively, sensors may be configured to sense the dynamic movement of an object about the sensor, such as a fingerprint swipe sensor that captures partial images of a fingerprint, reconstructs the fingerprint image, and compares the captured image to a stored image for authentication.

In such applications, cost, though always a factor in commercial products, has not been so critical—accuracy and reliability have been and still remain paramount factors. Typically, the placement sensor, a two-dimensional grid of sensors that senses a fingerprint image from a user's fingerprint surface all at once, was the obvious choice, and its many designs have become standard in most applications. Once the fingerprint image is sensed and reproduced in a digital form in a device, it is compared against a prerecorded and stored image, and authentication is complete when there is a match between the captured fingerprint image and the stored image. In recent years, fingerprint sensors have been finding their way into portable devices such as laptop computers, hand held devices, cellular telephones, and other devices. Though accuracy and reliability are still important, cost of the system components is very important. The conventional placement sensors were and still are very expensive for one primary reason: they all used silicon sensor surfaces. These surfaces are very expensive, as the silicon material is as expensive as the material to make a computer chip. Computer chips, of course, have become smaller over the years to reduce their cost and improve their performance. The reason the fingerprint silicon could not be made smaller: they need to remain the size of the average fingerprint, and the requirement for full scanning of the users' fingerprints simply cannot be compromised. The full print is required for adequate security in authentication.

Enter the fingerprint swipe sensor into the market. Swipe sensors are fundamentally designed with a line sensor configured to sense fingerprint features as a user swipes their finger in a perpendicular direction with respect to the sensor line. The cost saver: swipe sensors need much less silicon, only enough to configure a line sensor with an array of pixel sensors. The width is still fixed based on the average fingerprint width, but the depth is substantially smaller compared to the placement sensor. Some swipe sensors are capacitive sensors, where capacitance of the fingerprint surface is measured and recorded line by line. Others send a small signal pulse burst into the surface of the fingerprint surface and measure response in a pickup line, again recording fingerprint features line by line. In either case, unlike the placement sensors, the full fingerprint image needs to be reconstructed after the user completes the swipe, and the individual lines are reassembled and rendered to produce a full fingerprint image. This image is compared with a fingerprint image stored in the laptop or other device, and a user will then be authenticated if there is an adequate match.

For the capacitive swipe sensors, the first generation sensors were constructed with direct current (DC) switched capacitor technology (for example U.S. Pat. No. 6,011,859). This approach required using two plates per pixel forming a capacitor between them, allowing the local presence of a finger ridge to change the value of that capacitor relative to air. These DC capacitive configurations took images from the fingerprint surface, and did not penetrate below the finger surface. Thus, they were easy to spoof, or fake a fingerprint with different deceptive techniques, and they also had poor performance when a user had dry fingers. RF (Radio Frequency) sensors were later introduced, because some were able to read past the surface and into inner layers of a user's finger to sense a fingerprint. Different radio frequencies have been utilized by various devices along with different forms of detection including amplitude modulation (AM) and, phase modulation (PM). There are also differing configurations of transmitters and receivers, one type (for example U.S. Pat. No. 5,963,679) uses a single transmitter ring and an array of multiple low quality receivers that are optimized for on chip sensing. In contrast another type (for example U.S. Pat. No. 7,099,496) uses a large array of RF transmitters with only one very high quality receiver in a comb like plate structure optimized for off chip sensing.

One key impediment to the development of low cost placement sensors has been the issue of pixel density, and the resultant requirement for a large number of interconnections between layers of the sensor device. A typical sensor for a fingerprint application will be on the order of 10 mm.times.10 mm, with a resolution of 500 dpi. Such a sensor array would be approximately 200 rows by 200 columns, meaning there would need to be 200 via connections between layers in the device. While semiconductor vias can be quite small, the cost for implementing a sensor in silicon has proven to be prohibitive, as mentioned above.

In order to produce a placement sensor at a low enough cost for mass market adoption, lower cost processes such as circuit board etching must be employed. The current state of the art in circuit board via pitch is on the order of 200 µm, vs. the 50 µm pitch of the sensor array itself. Additionally, the added process steps required to form vias between layers of a circuit board significantly increase the tolerances for the minimum pitch of traces on each of the layers. Single-sided circuits may be readily fabricated with high yield with line pitch as low as 35 µm, whereas double sided circuits require a minimum line pitch on the order of 60 µm or more, which is too coarse to implement a full 500 dpi sensor array. One further consideration is that at similar line densities, double-sided circuits with vias are several times more expensive per unit area than single sided, making high-density double sided circuits too expensive for low cost sensor applications.

For laptop devices, adoption of the swipe sensor was driven by cost. The swipe sensor was substantially less expensive compared to the placement sensors, and most manufacturers of laptops adopted them based solely on price. The cost savings is a result of using less silicon area. More recently a substitute for the silicon sensor arose, using plastic Kapton® tape with etched sensing plates on it, connected to a separate processor chip (for example U.S. Pat. No. 7,099,496). This allowed the silicon portion of the sensor to be separated from the sensing elements and the silicon to follow Moore's law, shrinking to an optimal size, in length, width and depth in proportion to advances in process technology. Although this advance in the art enabled cheap durable Swipe Sensors, it did not overcome the basic image reconstruction and ergonomics issues resulting from changing from a simple two dimensional placement format. In addition to Swipe Sensors being cheaper, they take up less real estate in a host device, whether it is a laptop or a smaller device, such as a cellular phone or personal data device.

In most swipe class sensors, the fingerprint reconstruction process turned out to be a greater ergonomic challenge to users and more of a burden to quality control engineers than initially expected. Users needed to be trained to swipe their finger in a substantially straight and linear direction perpendicular to the sensor line as well as controlling contact pressure. Software training programs were written to help the user become more proficient, but different environmental factors and the inability of some to repeat the motion reliably gave Swipe Sensors a reputation for being difficult to use. Initial data from the field indicated that a large number of people were not regularly using the Swipe Sensors in the devices that they had purchased and opted back to using passwords. Quality control engineers who tried to achieve the optimum accuracy and performance in the matching process between the captured and reconstructed image found that the number of False Rejects (FRR), and False Acceptances (FAR), were much higher in Swipe Sensors than in placement sensors. Attempts to improve these reconstruction algorithms failed to produce equivalent statistical performance to placement sensors.

Other claims of the Swipe Sensor such as the use of less host real estate did not pan out. Various ramps, wells and finger guides had to be incorporated into the surfaces of the host devices to assist the user with finger placement and swiping. These structures ended up consuming significant space in addition to the actual sensor area. In the end, swipe sensors ended up taking up almost as much space as the placement sensors. This was not a big problem for full size laptops, but is currently a substantial problem for smaller laptops and netbooks, mobile phones, PDAs, and other small devices like key fobs.

Real estate issues have become even more of an issue with mobile device manufacturers who now require that the fingerprint sensor act also as a navigation device, like a mouse or touch-pad does in a laptop. The swipe sensor has proved to be a poor substitute for a mouse or touch pad due to the fact that they are constructed with an asymmetric array of pixels. Swipe sensors do a good job of detecting motion in the normal axis of the finger swipe but have difficulty accurately tracking sideways motion. Off axis angular movements are even more difficult to sense, and require significant processor resources to interpolate that movement with respect to the sensor line, and often have trouble resolving large angles. The byproduct of all this is a motion that is not fluid and difficult to use.

It is clear that low cost two dimensional fingerprint sensor arrays would serve a market need, but present art has not been able to fill that need. Conventional capacitive fingerprint sensors typically use distinct electrode structures to form the sensing pixels array. These electrode structures are typically square or circular and can be configured in a parallel plate configuration (for example U.S. Pat. Nos. 5,325,442 and 5,963,679) or a coplanar configuration (for example U.S. Pat. Nos. 6,011,859 and 7,099,496).

These prior art approaches cannot be configured into a low cost two dimensional array of sensing elements. Many capacitive fingerprint sensors (for example U.S. Pat. Nos. 5,963,679 and 6,011,859) have plate structures that must be connected to the drive and sense electronics with an interconnect density that is not practical for implementation other than using the fine line multilayer routing capabilities of silicon chips and therefore require lots of expensive silicon die are as stated before. Other sensors (for example U.S. Pat. No. 7,099,496) use off chip sensing elements on a cheap polymer film, but the sensor cell architecture is inherently one dimensional and cannot be expanded into a two dimensional matrix.

Another application for capacitive sensing arrays has been in the area of touch pads and touch screens. Because touchpad and touch screen devices consist of arrays of drive and sense traces and distinct sense electrodes, they are incapable of resolutions below a few hundred microns, making this technology unsuitable for detailed imaging applications. These devices are capable of detecting finger contact or proximity, but they provide neither the spatial resolution nor the gray-scale resolution within the body of the object being sensed necessary to detect fine features such as ridges or valleys.

Conventional art in the touchpad field utilizes a series of electrodes, either conductively (for example U.S. Pat. No. 5,495,077) or capacitively (for example US publication 2006/0097991). This series of electrodes are typically coupled to the drive and sense traces. In operation these devices produce a pixel that is significantly larger in scale than the interconnect traces themselves. The purpose is to generally sense presence and motion of an object to enable a user to navigate a cursor, to select an object on a screen, or to move a page illustrated on a screen. Thus, these devices operate at a low resolution when sensing adjacent objects.

Thus, there exists a need in the art for improved devices that can provide high quality and accurate placement sensors for use in different applications, such as fingerprint sensing and authentication for example, and that may also operate as a navigation device such as a mouse or touch pad in various applications. As will be seen, the embodiment provides such a device that addresses these and other needs in an elegant manner.

Given the small size and functional demands of mobile devices, space savings are important. Thus, it would also be useful to be able to combine the functions of a sensor with that of other components, such as power switches, selector switches, and other components, so that multiple functions are available to a user without the need for more components that take up space.

Still further, it would be also useful for different embodiments of a touch sensor to provide various alternatives for providing biometric sensors that are easy to use and feasible in different applications.

BRIEF DESCRIPTION OF DRAWINGS

FIG. 12B shows one example of a layout of the drive and sense traces for an embodiment that incorporates the folded aspect of the embodiment laid out flat prior to folding.

FIGS. 19A-J show another example of a fingerprint sensor system having an integrated switch, a dome switch in this example, to allow a user to contact a fingerprint sensor and to actuate a switch simultaneously.

FIGS. 22A-26C illustrate other embodiments of the invention.

DETAILED DESCRIPTION

Figure 1:
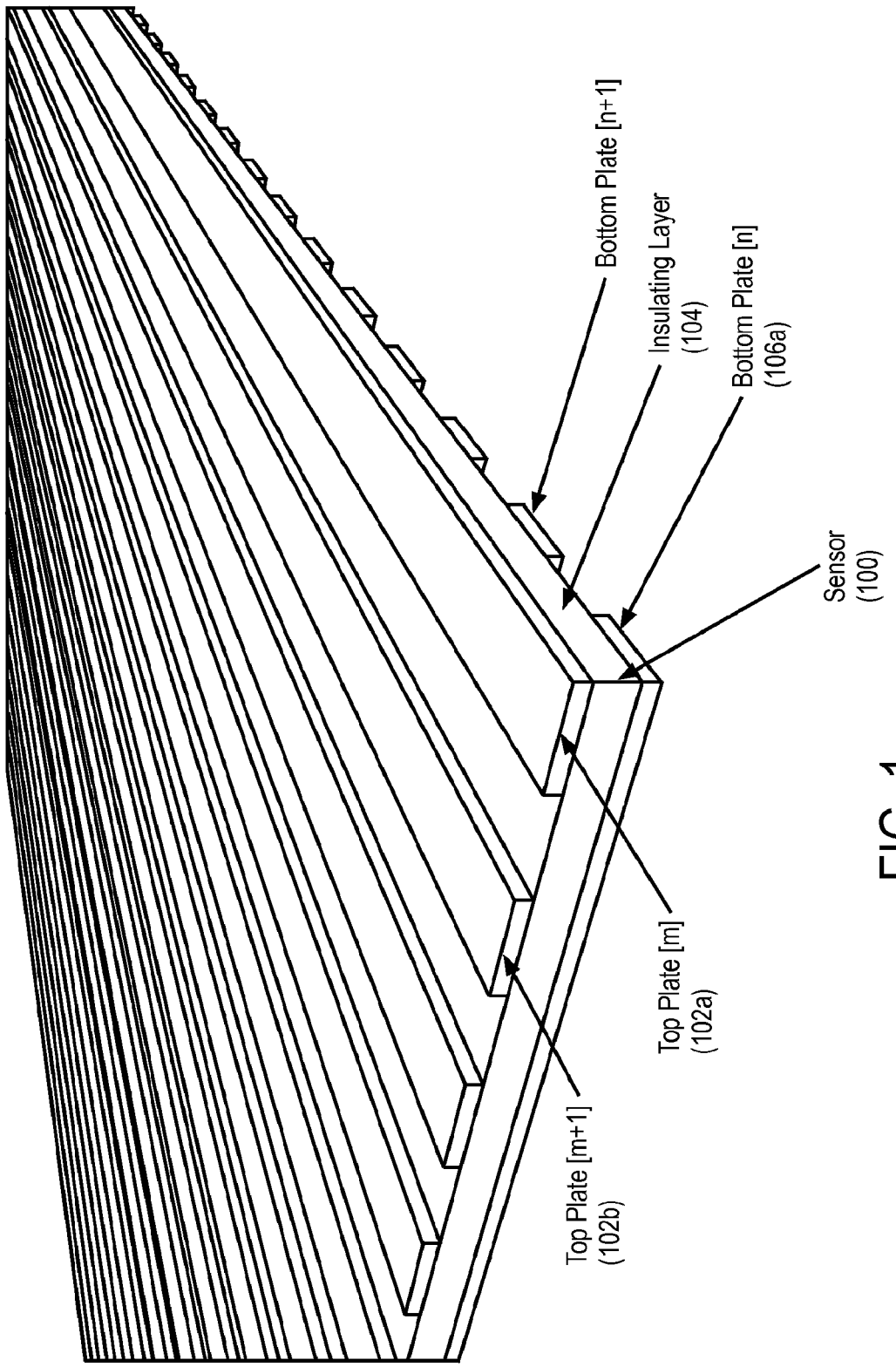
FIG. 1 shows a diagrammatic view of one embodiment showing the drive and pickup plate structures with an insulating dielectric layer separating the drive and pickup lines.

As discussed in the background, there are many applications for a two dimensional impedance sensor, and the embodiment provides a broad solution to shortcomings in the prior art for many applications. Generally, one embodiment is directed to a two-dimensional sensor, and may also be referred to as a placement sensor, area sensor, 2D sensor. The sensor may have sensor lines located on one or more substrates, such as for example a flexible substrate that can be folded over on itself to form a grid array with separate sensor lines orthogonal to each other. The sensor lines may alternatively be formed on separate substrates. In either or any configuration, the crossover locations of different sensor lines create sensing locations for gathering information of the features and/or characteristics of an object, such as a fingerprint for example.

In one embodiment, the drive lines and pickup lines are not electrically intersecting or connected in a manner in which they would conduct with each other, they form an impedance sensing electrode pair with a separation that allows the drive lines to project an electrical field and the pickup lines to receive an electrical field, eliminating the need for distinct electrode structures. The two lines crossing with interspersed dielectric intrinsically creates an impedance sensing electrode pair. Thus, the sensor is configured to activate two one-dimensional sensor lines to obtain one pixel of information that identifies features and/or characteristics of an object. Unlike conventional sensors, a sensor configured according to certain embodiments may provide a two dimensional grid that is capable of capturing multiple pixels of information from an object by activating individual pairs of drive and pickup lines and capturing the resultant signal. This signal can be processed with logic or processor circuitry to define features and/or characteristics of an object. For example, the information may be used to produce renderings of an object, such as a fingerprint, and compare the renderings to secured information for authentication.

According to one embodiment, and in contrast to conventional approaches, a device can utilize the intrinsic impedance sensing electrode pair formed at the crossings between the drive and pickup lines. In operation, the electric fields may be further focused by grounding drive and pickup lines near or about the area being sensed by the particular crossover location at one time. This prevents interference that may occur if other drive and pickup lines were sensing electric fields simultaneously. More than one electrode pair may be sensed simultaneously. However, where resolution is an important factor, it may be preferred to avoid sensing electrode pairs that are too close to each other to avoid interference and maintain accuracy in sensing object features at a particular resolution. For purposes of this description, "intrinsic electrode pair" refers to the use of the impedance sensing electrode pairs that are formed at each of the drive and pickup line crossover locations. Due to the fact that the embodiments use each intrinsic electrode pair at each crossover as a sensing element, no differentiating geometric features exist at individual sensing nodes to distinguish them from the interconnect lines. As a result, the alignment between the drive layers and sense layers is non-critical, which significantly simplifies the manufacturing process.

Grounding the adjacent inactive drive and pickup lines restricts the pixel formed at each intrinsic electrode pair without requiring complex measures such as the dedicated guard rings employed in prior art (for example U.S. Pat. No. 5,963,679). Instead, guard grounds around the pixel are formed dynamically by switching adjacent inactive drive and pickup lines into ground potential. This allows the formation of high density pixel fields with relatively low resolution manufacturing processes, as the minimum pixel pitch for a given process is identical to the minimum feature spacing. This, in turn, enables the use of low cost manufacturing process and materials, which is the key to creating a low cost placement sensor.

In one example, the sensor lines may consist of drive lines on one layer and pickup lines on another layer, where the layers are located over each other in a manner that allows the separate sensor lines, the drive and pickup lines, to cross over each other to form impedance sensing electrode pairs at each crossover location. These crossover locations provide individually focused electrical pickup locations or pixels, or electrode pairs where a number of individual data points of features and/or characteristics of an object can be captured. The high degree of field focus is due to the small size of the intrinsic electrode pairs, as well as the high density of the neighboring ground provided by the inactive plates. The flexible substrate may have a second substrate configured with logic or processor circuitry for sending and receiving signals with the sensor lines to electronically capture information related to the object. Alternatively, there may be two separate substrates carrying the separate sensor lines and layered on each other, and yet connected to a third substrate for connection to logic or processor circuitry.

The utilization of the crossover locations between perpendicular lines on adjacent layers for the pickup cell greatly reduces the alignment requirements between the layers. Since there are no unique features at a sensor pixel location to align, the only real alignment requirement between the layers is maintaining perpendicularity. If the sense cell locations had specific features, such as the parallel plate features typical of prior art fingerprint sensors, the alignment requirements would include X and Y position tolerance of less than one quarter a pixel size, which would translate to less than +/−12 μm in each axis for a 500 DPI resolution fingerprint application.

In operation, a drive line is activated, with a current source for example, and a pickup line is connected to a receiving circuit, such as an amplifier/buffer circuit, so that the resulting electric field can be captured. An electric field extends from the drive line to the pickup line through the intermediate dielectric insulating layer. If an object is present, some or all of the electric field may be absorbed by the object, changing the manner in which the electric field is received by the pickup line. This changes the resulting signal that is captured and processed by the pickup line and receiving circuit, and thus is indicative of the presence of an object, and the features and characteristics of the object may be sensed and identified by processing the signal. This processing may be done by some form of logic or processing circuitry.

In other embodiments, the signal driving the drive line may be a complex signal, may be a varying frequency and/or amplitude, or other signal. This would enable a sensor to analyze the features and/or characteristics of an object from different perspectives utilizing a varying or complex signal. The signal may include simultaneous signals of different frequencies and/or amplitudes that would produce resultant signals that vary in different manners after being partially or fully absorbed by the object, indicating different features and characteristics of the object. The signal may include different tones, signals configured as chirp ramps, and other signals. Processing or logic circuitry may then be used to disseminate various information and data points from the resultant signal.

In operation, the varying or complex signal may be applied to the drive line, and the pickup line would receive the resulting electric field to be processed. Logic or processing circuitry may be configured to process the resulting signal, such as separating out different frequencies if simultaneous signals are used, so that features and/or characteristics of the object may be obtained from different perspectives.

Given the grid of pixels that can be activated at individual pairs, each pixel may be captured in a number of ways. In one embodiment, a drive line may be activated, and pickup lines may be turned on and off in a sequence to capture a line of pixels. This sequencing may operate as a scanning sequence. Here a first drive line is activated by connecting it to a signal source, and then one pickup line is connected to amplifier/buffer circuitry at a time, the information from the pixel formed at the crossing of the two lines is captured, and then disconnected. Then, a next pixel is processed in sequence, then another, then another, until the entire array of pickup lines is processed. The drive line is then deactivated, and another drive line is activated, and the pickup lines are again scanned with this active drive line. These may be done one at a time in sequence, several non-adjacent pixels may be processed simultaneously, or other variations are possible for a given application. After the grid of pixels is processed, then a rendering of object information will be possible.

Referring to FIG. 1, a diagrammatic view of one embodiment of a sensor 100 configured according to one embodiment is illustrated. In this configuration, pickup lines or top plates 102a[m], 102b[m+1] are located on an insulating dielectric substrate layer 104. Drive lines or bottom plates 106a[n], 106b[n+1] are juxtaposed and substantially perpendicular to the pickup lines or plates and configured to transmit a signal into a surface of an object located in close proximity to the sensor lines and are located on an opposite side of the a insulating dielectric substrate to form a type of a grid. The pickup lines are configured to receive the transmitted electromagnetic fields modified by the impedance characteristics on an object placed within the range of those electric fields.

Figure 2:
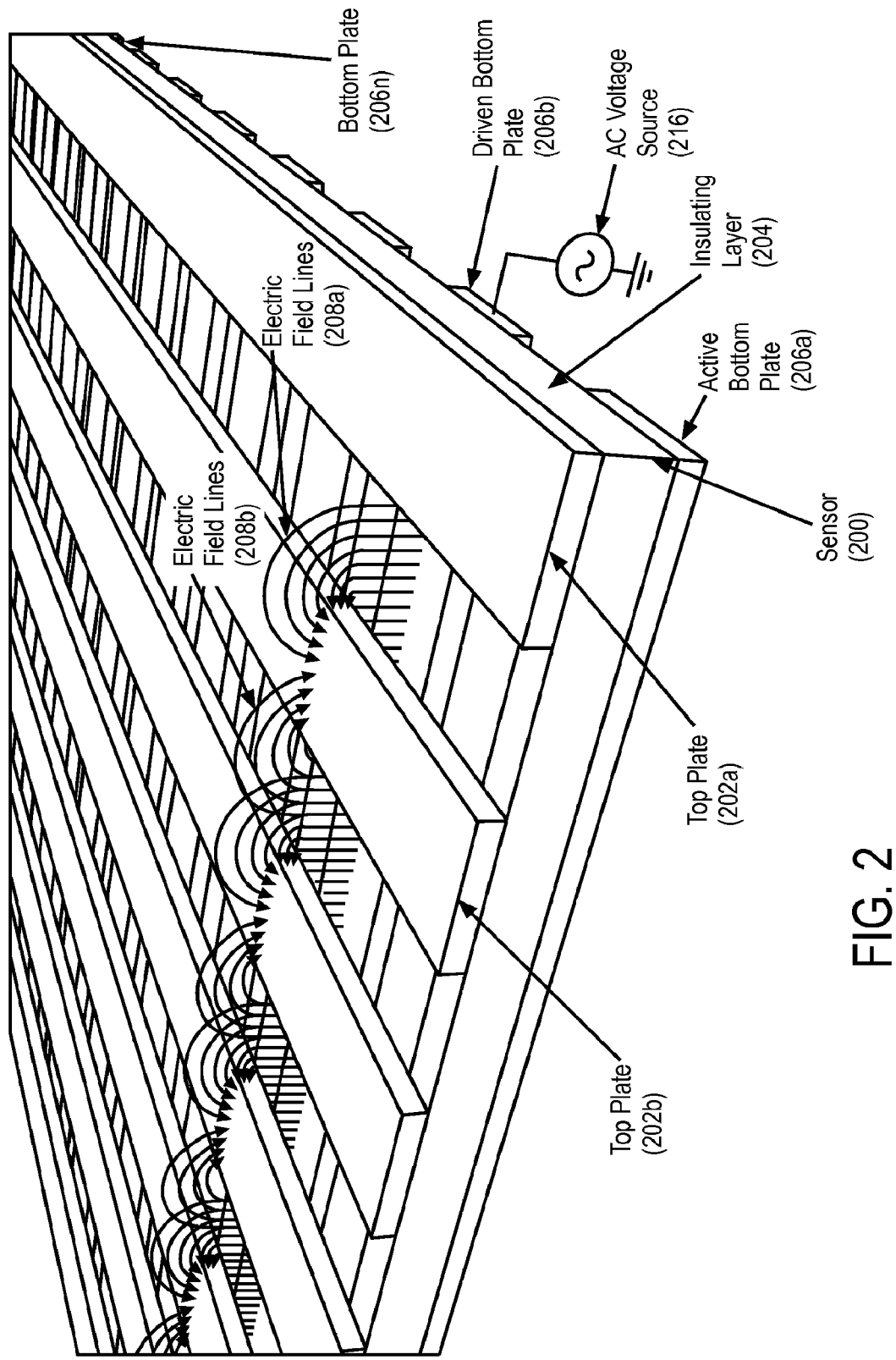
FIG. 2 shows a basic diagrammatic view of one embodiment showing the basic electrical field operation without an object in close proximity to the drive and pickup plate structures with one drive plate excited by a voltage source.

Referring to FIG. 2, a diagrammatic view of a sensor 200 is shown having pickup lines or top plates 202a, 202b and insulating layer 204, and drive lines or bottom plates 206a, 206b. The Figure further illustrates how electromagnetic fields 208a, 208b extend between the drive lines and pickup plates through the substrate. Without an object within proximity, the electric field lines are uniform within the sensor structure and between the different lines. When an object is present, a portion of the electric field lines are absorbed by the object and do not return to the pickup plates through the insulating layer.

Figure 3:
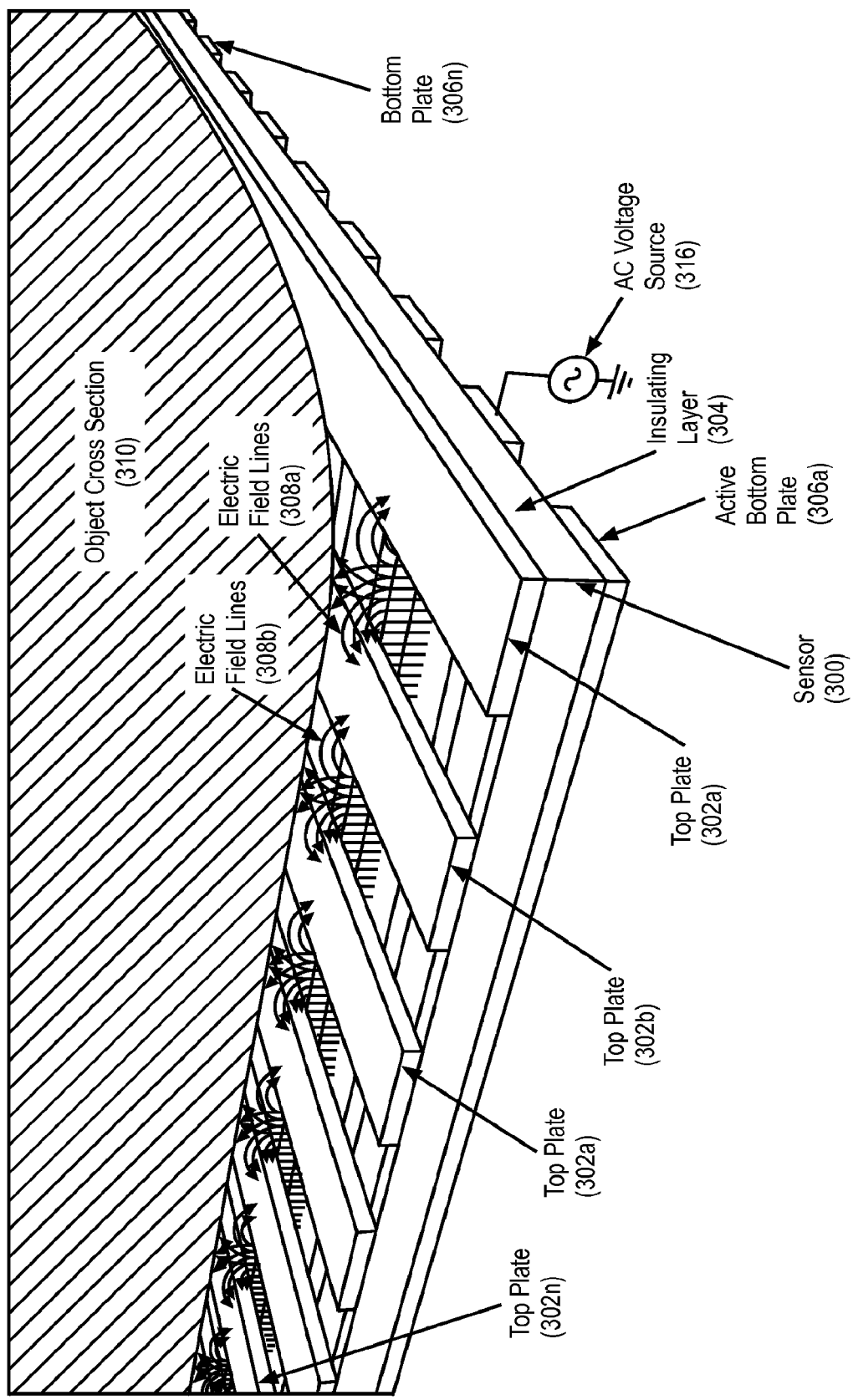
FIG. 3 shows a basic diagrammatic view of one embodiment showing the basic electrical field operation with an object in close proximity to the drive and pickup plate structures with one drive plate excited by a voltage source.

Referring to FIG. 3, an object 310 is illustrated proximate the sensor 300. The sensor 300 has pickup lines or top plates 302a, 302b, an insulating dielectric layer 304, and drive lines or bottom plates 306a, 306b. In operation, the drive lines and pickup lines of this device example may be individually activated, where a drive line/pickup line pair is activated to produce an active circuit. The result is a circuit that transmits electric field from active drive plate 316 into the combined dielectric of the insulating layer 304 and object 310 via electric field lines, 306a, 306b, and received by the active pickup plate. As the illustration shows, some of the field lines are captured by the object when it is placed about the active electrode pair. The variations in an object, such as peaks and valleys and other features of an object surface, can be detected and captured electronically by capturing and recording the resulting electric field variations occurring at different crossover locations of the drive and pickup lines. Similar to common capacitance based placement sensors, the sensor can capture a type of image of the object surface electronically, and generate a representation of the features and characteristics of an object, such as the features and characteristics of a fingerprint in the fingerprint sensor example described below.

In this configuration of FIG. 3, only one active electrode pair is illustrated. However, the embodiment is not limited to this particular configuration, where one single electrode pair, several electrode pairs, or even all electrode pairs may be active at one time for different operations. In practice, it may be desirable for less than all of the electrode pairs to be active at a given time, so that any interference that may occur between close-by pixels would be minimized. In one embodiment, a drive line may be activated, and the pickup lines may be scanned one or more at a time so that a line of pixels can be captured along the drive line and pickup lines as they are paired along a line at the crossover locations. This is discussed in more detail below in connection with FIG. 5.

In general, in operation, each area over which a particular drive line overlaps a pickup line with a separation of the a insulating dielectric substrate is an area that can capture and establish a sensing location that defines characteristics or features of a nearby object about that area. Since there exist multiple sensing locations over the area of the sensor grid, multiple data points defining features or characteristics of a nearby object can be captured by the sensor configuration. Thus, the sensor can operate as a planar two-dimensional sensor, where objects located on or about the sensor can be detected and their features and characteristics determined.

As described in the embodiments and examples below, the embodiment is not limited to any particular configuration or orientation described, but is only limited to the appended claims, their equivalents, and also future claims submitted in this and related applications and their equivalents. Also, many configurations, dimensions, geometries, and other features and physical and operational characteristics of any particular embodiment or example may vary in different applications without departing from the spirit and scope of the embodiment, which, again, are defined by the appended claims, their equivalents, and also future claims submitted in this and related applications and their equivalents.

In the following description, numerous specific details are set forth in order to provide a thorough understanding of the embodiment. However, it will be apparent to one skilled in the art that the embodiment can be practiced without these specific details. In other instances, well known circuits, components, algorithms, and processes have not been shown in detail or have been illustrated in schematic or block diagram form in order not to obscure the embodiment in unnecessary detail. Additionally, for the most part, details concerning materials, tooling, process timing, circuit layout, and die design have been omitted inasmuch as such details are not considered necessary to obtain a complete understanding of the embodiment and are considered to be within the understanding of persons of ordinary skill in the relevant art. Certain terms are used throughout the following description and claims to refer to particular system components. As one skilled in the art will appreciate, components may be referred to by different names. This document does not intend to distinguish between components that differ in name, but not function. In the following discussion and in the claims, the terms "including" and "comprising" are used in an open-ended fashion, and thus should be interpreted to mean "including, but not limited to . . . ."

Embodiments of the embodiment are described herein. Those of ordinary skill in the art will realize that the following detailed description of the embodiment is illustrative only and is not intended to be in any way limiting. Other embodiments of the embodiment will readily suggest themselves to such skilled persons having the benefit of this disclosure. Reference will be made in detail to implementations of the embodiment as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals. Moreover, it will be appreciated that such a development effort might be complex and time-consuming, but would nevertheless be a routine undertaking of engineering for those of ordinary skill in the art having the benefit of this disclosure.

In one embodiment, a sensor device includes drive lines located on or about an insulating dielectric substrate and configured to transmit a signal onto a surface of an object being sensed. Pickup lines are located near or about the drive lines and configured to receive the transmitted signal from the surface of an object. In order to keep a separation between the drive lines and pickup lines, the substrate may act as an insulating dielectric or spacing layer. The substrate may be for example a flexible polymer based substrate. One example is Kapton® tape, which is widely used in flexible circuits such as those used in printer cartridges and other devices. The package may include such a flexible substrate, where the drive lines may be located on one side of the substrate, and the pickup lines may be located on an opposite side of the substrate.

The drive lines may be orthogonal in direction with respect to the pickup lines, and may be substantially perpendicular to the pickup lines. According to one embodiment, a device may be configured with drive lines and pickup lines located on or about opposite sides of an insulating dielectric substrate, where the combination of these three components provides capacitive properties. The drive lines may be activated to drive an electric field onto, into or about an object. The pickup lines can receive electronic fields that originated from the drive lines, and these electronic fields can be interpreted by processing or logic circuitry to interpret features or characteristics of the object being sensed.

Thus, in one embodiment the layer separating the drive lines from the pickup lines can provide a capacitive property to the assembly. If some or all of the drive lines are substantially perpendicular to the pickup lines, either entirely or in portions, then a grid may be formed. In such a configuration, from a three dimensional view, the drive lines are located and oriented substantially in parallel with respect to each other about a first plane. One surface of the substrate is located about the drive lines in a second plane that is substantially parallel relative to the drive lines. The pickup lines are located and oriented substantially in parallel with respect to each other about a third plane that is substantially parallel to the first and second planes and also located about another substrate surface that is opposite that of the drive lines, such that the substrate is located substantially between the drive lines and the pickup lines.

In this description, including descriptions of embodiments and examples, there will be references to the terms parallel, perpendicular, orthogonal and related terms and description. It is not intended, nor would it be understood by those skilled in the art that these descriptions are at all limiting. To the contrary, the embodiment extends to orientations and configurations of the drive lines, the pickup lines, the substrate or related structure, and also various combinations and permutations of components, their placement, distance from each other, and order in different assemblies of a sensor. Though the embodiment is directed to a sensor configured with plurality of drive and pickup lines that generally cross over each other at a pixel location and are configured to detect presence and other features and characteristics of a nearby object, the embodiment is not limited to any particular configuration or orientation, but is only limited to the appended claims, their equivalents, and also future claims submitted in this and related applications and their equivalents.

Also, reference will be made to different orientations of the geometric planes on which various components will lie, such as the drive and pickup lines and the substrate that may be placed in between the sets of drive and pickup lines. If flexible substrates are used for example, the use of such a structure will allow for planes to change as a flexible structure is flexed or otherwise formed or configured. In such embodiment will be understood that certain aspects of the embodiment are directed to the drive lines and pickup lines being configured on opposite sides of a substrate and in a manner that enables the sensing of particular features and/or characteristics of a nearby object at each crossover location of a drive line and a pickup line. Thus, the orientation of the planes (which may be deformable, and thus may be sheets separated by a substantially uniform distance) of groups of components (such as drive lines or pickup lines for example) or substrates may vary in different applications without departing from the spirit and scope of the embodiment.

Also, reference will be made to pickup lines, pickup plates, drive lines, drive plate, and the like, but it will be understood that the various references to lines or plates may be used interchangeably and do not limit the embodiment to any particular form, geometry, cross-sectional shape, varying diameter or cross-sectional dimensions, length, width, height, depth, or other physical dimension of such components. Also, more sophisticated components may be implemented to improve the performance of a device configured according to the embodiment, such as for example small 65, 45, 32 or 22 nanometer conduction lines or carbon nanotubes that may make an assembly more easily adapted to applications where small size and shape as well as low power are desired characteristics and features. Those skilled in the art will understand that such dimensions can vary in different applications, and even possibly improve the performance or lower power consumption in some applications, without departing from the spirit and scope of the embodiment.

Reference will also be made to various components that are juxtaposed, layered, or otherwise placed on each other. In one example of an embodiment, a plurality of drive lines are juxtaposed on one surface of a generally planar substrate, and a plurality of pickup lines are juxtaposed on an opposite surface of the planar substrate. The drive lines are substantially orthogonal to the pickup lines, and may be described as substantially perpendicular to the pickup lines. The distance between the drive lines and pickup lines may be filled with a substrate or insulating material that will provide for a capacitive configuration. Here the drive lines on one side of the substrate forms one capacitive plate, and the pickup lines on an opposite side for the corresponding capacitive plate. In operation, when the drive plate is activated, an electrical field is generated between the drive lines and pickup lines and through the substrate to form a plurality of capacitive elements. These capacitive elements are located at an area at each cross-section of a drive line and a pickup line with a portion of the substrate located between the areas. This is a location where the respective drive lines and pickup lines overlap each other. In any particular application, these areas in which the three components interact during operation define a data location at which a sensor reading can be made.

Reference will also be made to sensor lines, such as sensor drive lines and sensor pickup lines, and their orientation amongst themselves and each other. For example, there will be described substantially parallel drive lines. These drive lines are intended to be described as parallel conductive lines made up of a conductive material formed, etched, deposited or printed onto the surface such as copper, tin, silver and gold. Those skilled in the art will understand that, with the inherent imperfections in most any manufacturing process, such conductive lines are seldom "perfect" in nature, and are thus not exactly parallel in practice. Therefore, they are described as "substantially parallel". Different applications may configure some of the drive lines even non-parallel, such that the lines may occur parallel for a portion of the line, and the line may necessarily deviate from parallel in order to connect with other components for the device to operate, or in order to be routed on or about the substrate on which it is formed or traced. Similarly, the separate array of lines may be described as orthogonal or perpendicular, where the drive lines are substantially orthogonal or perpendicular to the pickup lines. Those skilled in the art will understand that the various lines may not be perfectly perpendicular to each other, and they may be configured to be off-perpendicular or otherwise crossed-over in different angles in particular applications. They also may be partially perpendicular, where portions of drive lines may be substantially perpendicular to corresponding portions of pickup lines, and other portions of the different lines may deviate from perpendicular in order to be routed on or about the substrate or to be connected to other components for the device to operate.

These and other benefits provided by the embodiment will be described in connection with particular examples of embodiments of the embodiment and also descriptions of intended operational features and characteristics of devices and systems configured according to the embodiment.

In operation, generally, the drive lines can transmit an electromagnetic field toward an object that is proximal to the device. The pickup lines may receive a signal originating from the drive lines and then transmitted through the object and through the substrate and onto the pickup lines. The pickup lines may alternatively receive a signal originating from the drive lines that were then transmitted through the substrate and onto the pickup lines without passing through the object. This electric field can vary at different locations on the grid, giving a resultant signal that can be interpreted by some type of logic or processor circuitry to define features and/or characteristics of an object that is proximate the assembly.

The drive lines and pickup lines may be controlled by one or more processors to enable the transmission of the signal to an object via the drive lines, to receive a resultant signal from an object via the pickup lines, and to process the resultant signal to define an object image. One or more processors may be connected in one monolithic component, where the drive lines and pickup lines are incorporated in a package that includes the processor. In another embodiment, the drive lines, pickup lines and substrate may be assembled in a package by itself, where the package can be connected to a system processor that controls general system functions. This way, the package can be made part of the system by connecting with a system's input/output connections in order to communicate with the system. This would be similar in nature for example to a microphone connected to a laptop, where the audio signals are received by the system processor for use by the laptop in receiving sounds from a user. According to this embodiment, the sensor can be connected as a stand-alone component that communicates with the system processor to perform sensor operations in concert with the system processor.

In another embodiment, a sensor may be configured to drive signals at different frequencies since the impedance of most objects, especially human tissue and organs, will greatly vary with frequency. In order to measure complex impedance at one or more frequencies of a sensed object, the receiver must be able also to measure phase as well as amplitude. In one embodiment, the resulting signal generated from a given impedance sensing electrode pair may result from varying frequencies, known in the art as frequency hopping, where the receiver is designed to track a random, pseudo-random or non-random sequence of frequencies. A variation of this embodiment could be a linear or non-linear frequency sweep known as a chirp. In such an embodiment one could measure the impedance of a continuous range frequencies very efficiently.

In yet another embodiment, a grid sensor as described above may be configured to also operate as a pointing device. Such a device could perform such functions as well known touch pads, track balls or mice used in desktops and laptop computers.

In one example of this embodiment, a two dimensional impedance sensor that can measure the ridges and valleys of a fingertip may be configured to track the motion of the fingerprint patterns. Prior art swiped fingerprint sensors can perform this function, but due to the physical asymmetry of the array and the need to speed correct, or "reconstruct" the image in real time make these implementations awkward at best. The sensor could also double as both a fingerprint sensor and a high quality pointing device.

One device configured according to the embodiment includes a first array of sensor lines on a flexible substrate, and a second array of sensor lines on a flexible substrate, and also a processor configured to process fingerprint data from the first and second arrays of sensor lines. When folded upon itself in the case of a single flexible substrate or when juxtaposed in the case of separate substrates, the separate sensor lines cross each other without electrically shorting to form a grid with cross-over locations that act as pixels from which fingerprint features can be sensed. In one embodiment, an array of substantially parallel sensor drive lines is located on a surface of the flexible substrate. These drive lines are configured to sequentially transmit signal into a surface of a user's finger activating a line at a time. A second array of sensor lines is similar to the first, consisting of substantially parallel sensor pickup lines that are substantially perpendicular to the drive lines. These pickup lines are configured to pick up the signal transmitted from the first.

In the configuration where the first and second set of sensor lines, the drive and the pickup lines for example, are located on different sections of an extended surface of the flexible substrate, the flexible substrate is further configured to be folded onto itself to form a dual layer configuration. Here, the first array of sensor drive lines becomes substantially perpendicular to the second array of pickup sensor lines when the flexible substrate is folded onto itself. This folding process creates crossover locations between these separate arrays of sensor lines—though they must not make direct electrical contact so that they operate independently. These crossover locations represent impedance sensing electrode pairs configured to sense pixels of an object and its sub-features juxtaposed relative to a surface of the flexible substrate. The scanning of these pixels is accomplished by activating individual rows and columns sequentially. Once a drive column is activated with drive signal the perpendicular pickup rows are scanned one at a time over the entire length of the selected driver. Only one row is electrically active (high impedance) at a time, the non-active rows are either shorted to ground or multiplexed to a state where they do not cross couple signal. When a finger ridge is placed above an array crossover location that is active, it interrupts a portion of the electric field that otherwise would be radiated through the surface film from the active drive column to the selected row pickup. The placement of an object's subfeature, such as a ridge or valley in the case of a fingerprint sensor, over an impedance sensing electrode pair results in a net signal decrease since some of the electric field is conducted to ground through the human body. In a case of a fingerprint sensor the placement of a fingerprint ridge/valley over an impedance sensing electrode pair, the valley affects the radiation of electric field from the selected drive line to the selected pickup line much less than a ridge would. By comparing the relative intensity of signals between the pixels ridges and valleys, a two dimensional image of a finger surface can be created.

Referring again to FIG. 1, this general example of the grid sensor will be now used to illustrate how such a sensor configured according to the embodiment can be implemented as a fingerprint sensor, where the object would simply be the surface of the fingerprint on the user's finger. This example will be carried through the following Figures for illustration of the benefits and novel features of the impedance sensor configured according to the embodiment. However, it will be appreciated by those skilled in the art, however, that any object may be sensed by a device configured according to the embodiment. Again, the example and description are intended only for illustration purposes.

In operation, the sensor can be configured to detect the presence of a finger surface located proximate to the sensor surface, where the drive lines can drive an active electromagnetic field onto the finger surface, and the pickup lines can receive a resulting electromagnetic field signal from the pickup lines. In operation, the drive lines can generate an electric field that is passed onto the surface of the finger, and the different features of the fingerprint, such as ridges and valleys of the fingerprint surface and possibly human skin characteristics, would cause the resulting signal to change, providing a basis to interpret the signals to produce information related to the fingerprint features.

In one embodiment of a fingerprint sensor, referring again to FIG. 1 in the context of a fingerprint sensor, a flexible substrate is used as the insulating dielectric layer 104, to allow for beneficial properties of durability, low cost, and flexibility. The drive lines or plates 106a, 106b, are located on the flexible substrate and configured to transmit a signal into a surface of a user's fingerprint features and structures, such as ridges and valleys, placed on or about the sensor lines. The pickup lines 102a, 102b are configured to receive the transmitted signal from the user's finger surface. A processor (not shown) can be configured to collect and store a fingerprint image based on the received signal from the pickup lines.

Figure 4:
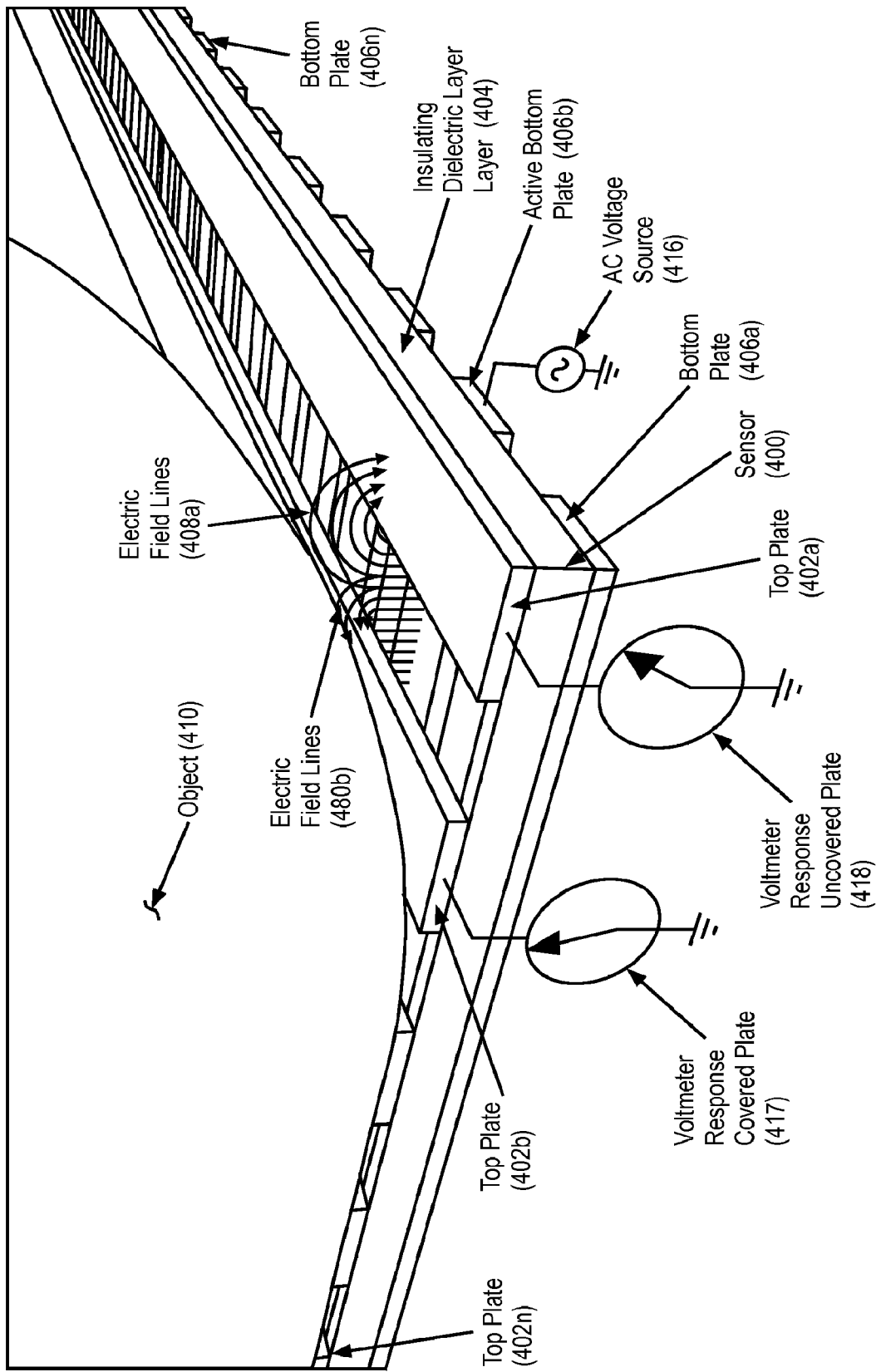
FIG. 4 shows a basic diagrammatic view of one embodiment of the sensor showing the differences in field intensity with and without an object in close proximity to the drive and pickup plate structures with one drive plate excited by a voltage source.

Referring to FIG. 4, an example sensor 400 configured as an object sensor, where the top plates or pickup lines 402a, 402b, . . . , 402n are located on one side of insulating dielectric layer or substrate 404. Bottom plates or drive lines 406a, 406b, . . . , 406n are located on an opposite side of the substrate 404. Electric fields 408a, 408b extend from bottom plates or drive lines 406a, 406b through the insulating layer or substrate 404 and onto active top plate 402a. According to the embodiment, these drive lines may be activated one at a time to reduce any interference effects, but the electric field results illustrated here are intended to illustrate a contrast between electric fields that are partially or fully absorbed by the object with electric fields that are not absorbed by the object at all. This information may be collected from drive and pickup plate electrode pairs at each crossover location to sense features and characteristics of the object that is proximate the sensor lines. Partially covered top plate or pickup line 402b is connected to voltmeter 417, and uncovered top plate 402a is connected to voltmeter 418. Active drive line or bottom plate 406b is connected to is connected to AC signal source 416, causing an electric field to radiate from active plate 406b. According to a particular application, the number of drive lines and pickup lines can vary depending on the application, and it may depend on the cost and resolution desired. As can be seen, the electric field lines 408a is partially captured by the pickup lines 402a and 402b, and part is captured by the object, in this case finger 410. Also, in order to illustrate that the pickup lines will exhibit different reading when an object or object feature is present or not present or proximate to a given crossover location, volt meter 417 illustrates the response to the top plate or drive line 402b, and voltmeter 418 illustrates the response of top plate or drive line 402a. The difference in the deflections of voltmeter 417 in comparison 418 show the delta in electric field intensity between the two electrode pair locations, one with a finger present the other without.

Figure 5:
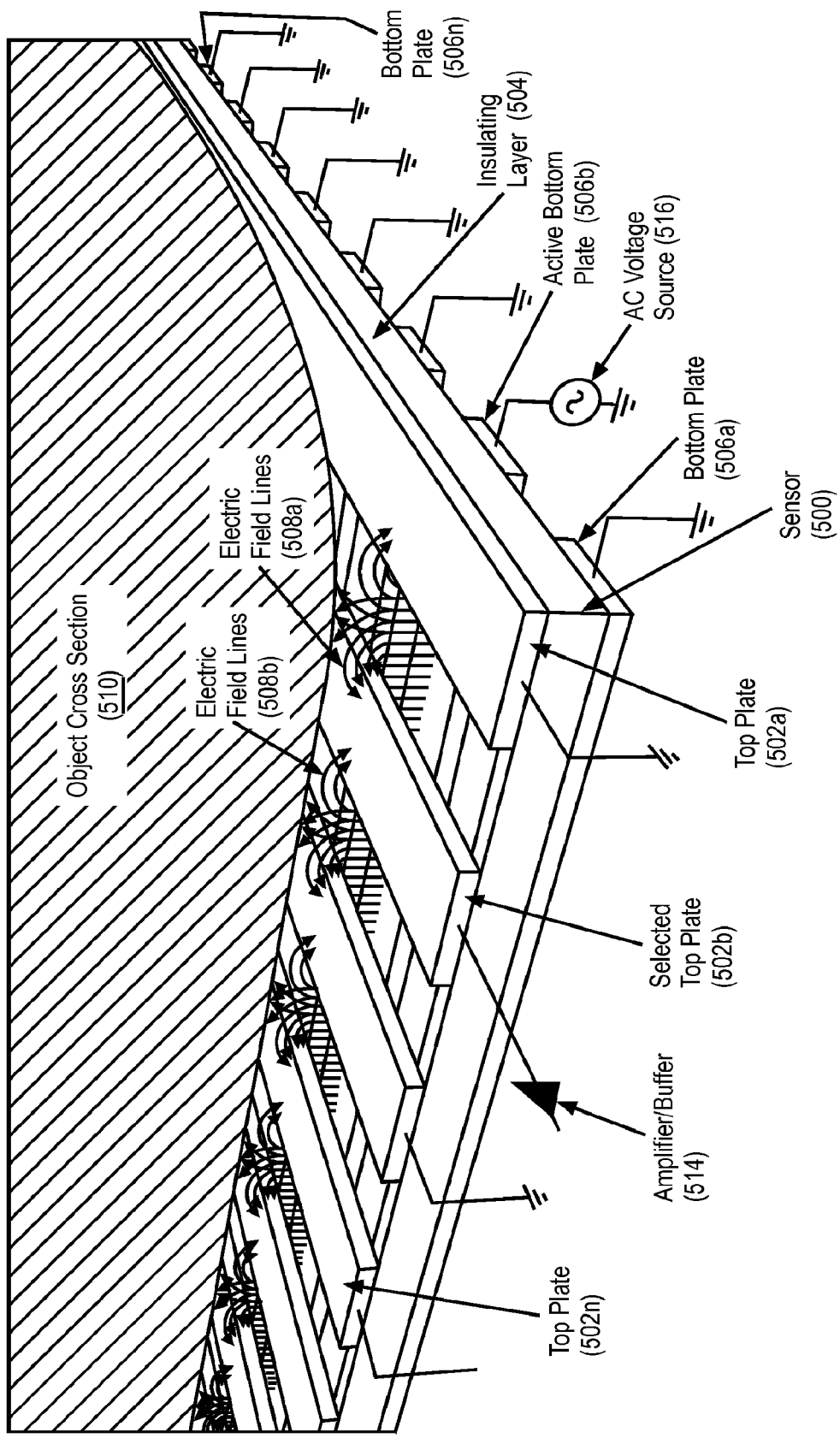
FIG. 5 shows a basic diagrammatic view of one embodiment showing the basic electrical field operation with an object in close proximity of the drive and pickup plate structures with the selected pickup plate amplified and all inactive drive and pickup plates grounded.

Referring to FIG. 5, another example of a sensor configured according to the embodiment is illustrated for the drive and pickup configuration when detecting the presence of an object. The sensor 500 is illustrated, where the top plates or pickup lines 502a, 502b, . . . , 502n are located on one side of insulating layer or substrate 504, and bottom plates or drive lines 506a, 506b, . . . , 506n are located on an opposite side of the substrate 504. Again, the pickup lines are shown on the layer closest to the object being sensed for maximum sensitivity, and the drive lines shown on the opposite side of the substrate. Electric fields 508a, 508b extend from bottom plates or drive lines 506a, 506b through the insulating layer or substrate 504 and onto active top plate 502b. Other configurations are possible, perhaps having drive plates on the top, and pickup plates on the bottom. The embodiment, however, is not limited to any particular configuration that is insubstantially different than the examples and embodiments disclosed and claimed herein.

FIG. 5, further shows a snapshot of one selected individual electrode pair located at the crossover of pickup line 502b and drive line 506b, where the remaining pickup and drive lines are not active, shown grounded in FIG. 5. Drive line 506b is connected to AC voltage source 516, and pickup line 502b is connected to amplifier/buffer 514. Once activated as shown here, electric field lines 508a, 508b are generated, and they radiate from drive line 506b and are sensed by pickup line 502b, sending the resultant signal into amplifier/buffer 514, and are later processed by analog and digital circuit functions. Grounding the inactive adjacent drive and pickup lines focuses the electric fields 508a and 508b at the crossover location between the active the drive and pickup plates, limiting crosstalk from adjacent areas on the object being sensed. As the sensing operation proceeds in this embodiment, different drive line/pickup line crossover pairings may be activated to capture different pixels of information from the object. In the case of an object sensor, it can capture information on the shape of the object, and, if the electrical characteristics are non-uniform across its surface, it's composition. Again, the embodiment is not limited to this particular configuration, where one single electrode pair, several electrode pairs, or even all electrode pairs may be active at one time for different operations. In practice, it may be preferable for less than all of the impedance sensing electrode pairs to be active at a given time, so that any interference that may occur between close-by pixels would be minimized. In one embodiment, a drive line may be activated, and the pickup lines may be scanned one or more at a time so that a line of pixels can be captured along the drive line and pickup lines as they are paired along a line at the crossover locations. Thus, and still referring to FIG. 5, the AC voltage source 516 may remain connected to drive line 506b, and the connection of the amplifier/buffer 516 may cycle or scan over to sequential pickup lines, so that another pixel of information can be captured from another pickup line crossover paired with drive line 506b. Once substantially all the pickup lines 506a-n have been scanned drive line 506b can be deactivated, than another drive line in sequence can be activated with the AC voltage source, and a new scanning can commence through the pickup lines. Once substantially all drive line/pickup line pairings have been scanned to capture the full two-dimensional array of pixels, then a two dimensional image or rendering of the object features and characteristics can be made, such as a rendering of the shape of the object, and potentially a composition map.

As another example of a sensor that can benefit from the embodiment, a reduced cost fingerprint swipe sensor could be configured using the same innovation provided by the embodiment. In this embodiment, a reduced number of pickup lines could be configured with a full number of orthogonal drive lines. Such a configuration would create a multi-line swipe sensor that would take the form of pseudo two-dimensional sensor, and when a finger was swiped over it would create a mosaic of partial images or slices. The benefit of this would be to reduce the complexity of image reconstruction task, which is problematic for current non-contact silicon sensors that rely on one full image line and a second partial one to do speed detection.

The tradeoff would be that this pseudo two dimensional array would have to be scanned at a much faster rate in order to keep up with the varying swipe speeds of fingers that have to be swiped across it.

Figure 6A:
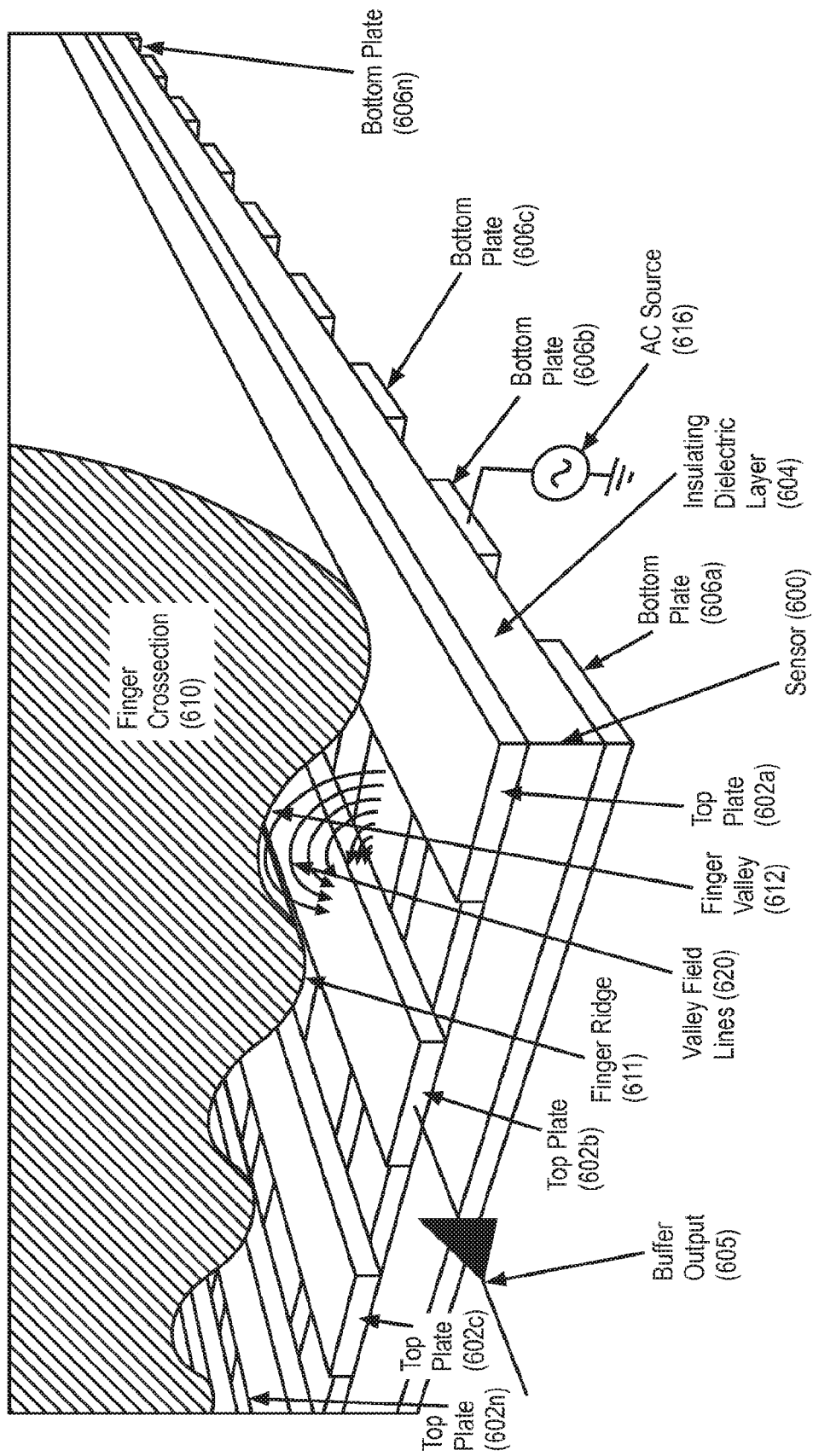
FIG. 6A shows a basic diagrammatic view of one embodiment showing the basic electrical field operation with a finger or object containing a ridge surface feature in close proximity to the active electrode pair.
Figure 6B:
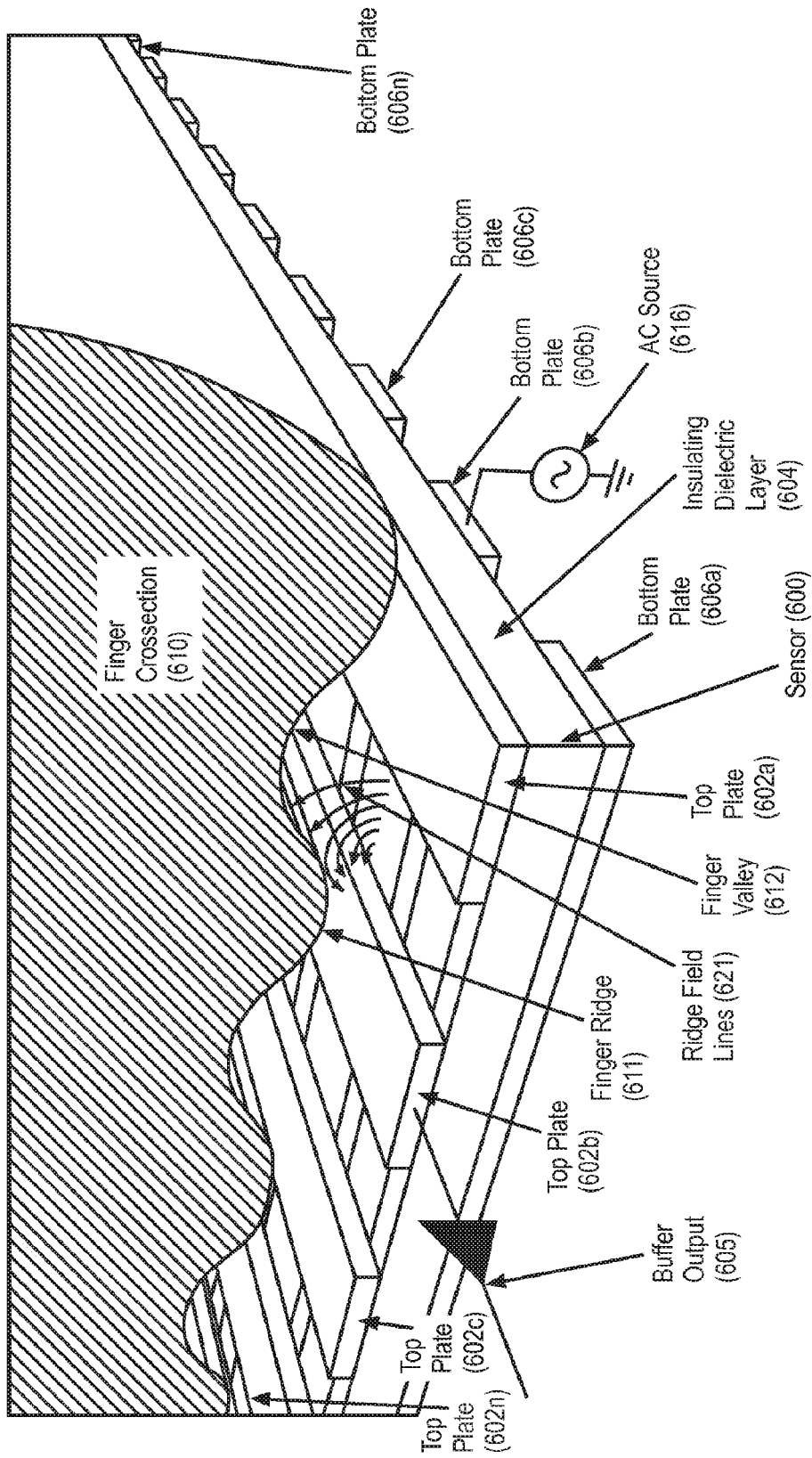
FIG. 6B shows a basic diagrammatic view of one embodiment showing the basic electrical field operation with a finger or object containing a valley surface feature in close proximity to the active electrode pair.

FIGS. 6A and 6B illustrate the operation of the sensor when detecting surface features of an object such as fingerprint ridges and valleys. The sensor is configured identically to the previous example in FIG. 5, but in this case is interacting with a textured surface such as a fingerprint.

Referring to FIGS. 6A and B, another example of a sensor configured according to the embodiment is illustrated. The sensor 600 is illustrated, where the top plates or pickup lines 602a-n are located on one side of insulating layer or substrate 604, and bottom plates or drive lines 606a-n are located on an opposite side of the substrate 604. For maximum sensitivity pickup lines are shown on the layer closest to the object being sensed, and the drive lines shown on the opposite side of the substrate. FIG. 6A shows electric field lines 620 as they interact with a proximally located object's valley and FIG. 6B shows electric field lines 621 as the interact with a proximally located object's peaks, extending from bottom plate drive line 606b through the insulating layer or substrate 604 and onto active top pickup line 602b. In the case of sensing a fingerprint, the corresponding ridges and valleys over the fingerprint surface can be captured by the grid of drive line/pickup line crossover points, and the resulting data can be used to render an image of the fingerprint. A stored fingerprint can then be compared to the captured fingerprint, and they can be compared for authentication. This is accomplished using any one of many fingerprint matching algorithms which are available from vendors as stand-alone products. Such vendors include Digital Persona, BioKey, and Cogent Systems, to name just a few.

Also illustrated in FIGS. 6A and B, is the individual sensor line pairing of pickup line 602b and drive line 606b. Their crossover forms the active electrode pair, and the remaining pickup and drive lines are not active, and will nominally be grounded by electronic switches. Drive line 606b is connected to AC voltage source 616, and pickup line 602b is connected to amplifier/buffer 605. Once activated as shown here, electric field lines 620 and 621 are created as shown in FIGS. 6A and 6B respectively, and they emanate between the drive line 606b and pickup line 602b, sending a resultant signal that is radiated onto pickup line 602b and connected to amplifier/buffer 605, and later processed by analog and digital processing circuitry. As the sensing operation proceeds in this embodiment, different drive line/pickup line crossover pairs may be activated to capture different pixels of information from the object. In the case of a fingerprint, it can capture information on different features and characteristics of the fingerprint and even the body of the finger itself. Again, the embodiment is not limited to this particular configuration, where one electrode pair, several electrode pairs, or even all electrode pairs may be active at one time for different operations. In practice, it may be preferable for less than all of the electrode pairs to be active at a given time, so that any interference that may occur between close-by pixels would be minimized. In one embodiment, a drive line may be activated, and the pickup lines may be scanned one or more at a time so that a line of pixels can be captured along the drive line and pickup lines as they are paired along a line at the crossover points. Thus, and still referring to FIG. 6A, the voltage source 616 may remain connected to drive line 606b, and the connection to buffer/amplifier 605 may cycle or scan over to another pickup line, so that another pixel of information can be captured from another electrode pair using driveline 606b.

In the snapshot shown in FIGS. 6A and 6B drive plate 606b remains excited by AC signal source 616 until an entire column of pixels is scanned, while unused drive plates (606a,c-n etc.), are switched to ground for isolation purposes. Likewise, in one embodiment only one pickup plate is active at a time and some or substantially all other pickup plates are switched to ground to minimize crosstalk.

The scanning process continues beyond the snapshot shown in FIGS. 6A and 6B, with the next column in sequence being activated, 606c, (although the sequence could be arbitrary), Once the entire sequence of Pickup Plates 602a-n is scanned, the next driver line 606d would activated, until all, or substantially all of the drive lines 606a-n have been sequenced. Once all the drive columns have been activated and the pickup plates scanned for each column, one will have collected a complete two dimensional array of pixels equal to the number of driver rows times the number of pickup columns. For a 500 DPI sensor that would create a 10.times.10 mm array or 100 mm.sup.2, consisting of 40,000 individual pixels. Depending on the application, all of the drive lines may be sequenced, or possibly some or most of them may be sequenced.

Referring again to FIGS. 6A and 6B, the two conductive layers Drive layer 606 and Pickup layer 602, are separated by an electrically insulating layer 604. This insulating layer 604 has high DC resistance and has a dielectric constant greater than one to allow the transmission of high frequency electric fields through it. In one embodiment this layer 602 is created by folding a single sided flexible printed circuit board back onto itself. In another embodiment it is created by placing a dielectric layer between two electrically active layers to form a double sided circuit board.

Figure 7:
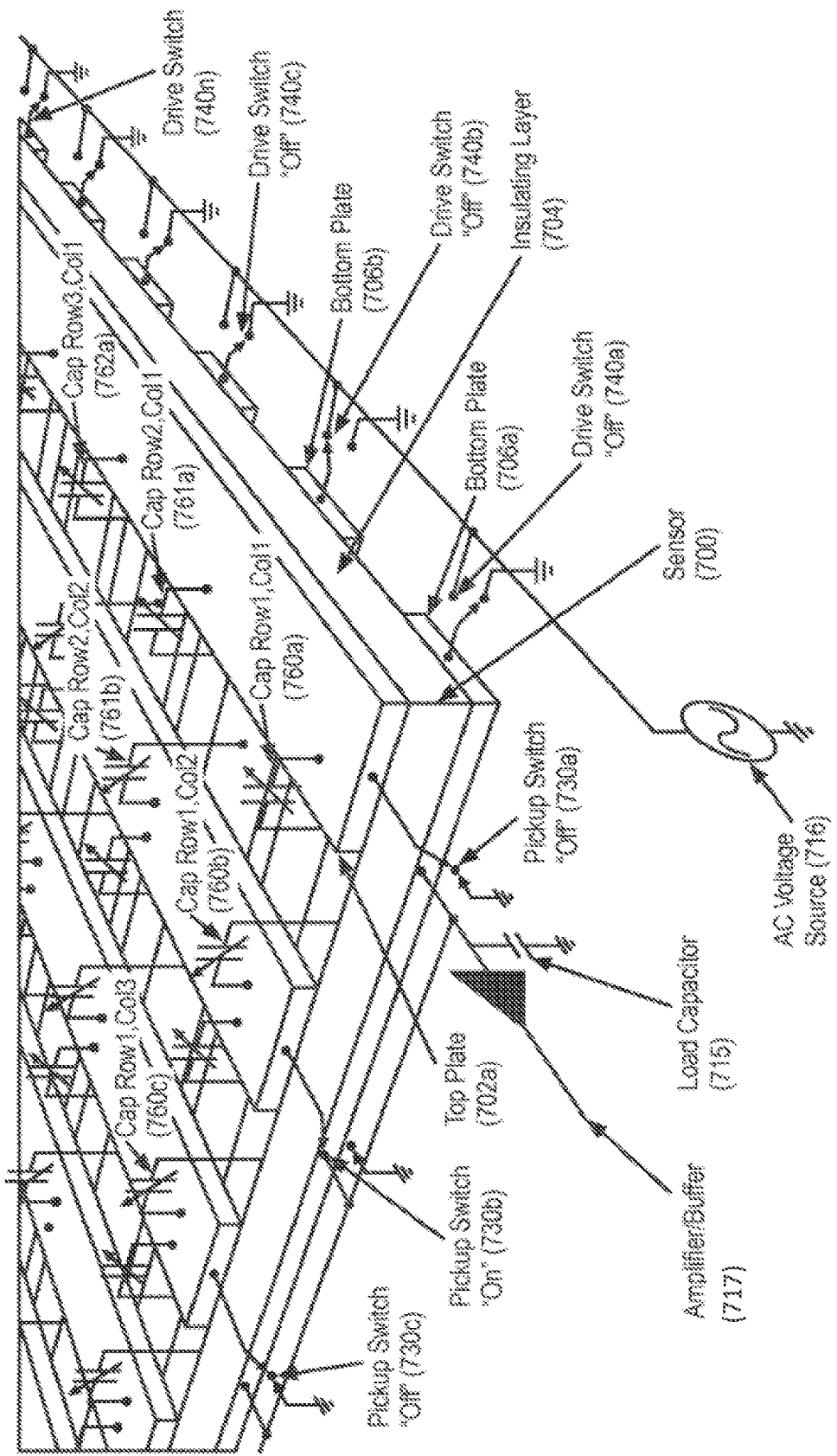
FIG. 7 shows a diagrammatic view of an x-y grid of plate rows and columns depicted by lumped circuit components that represent the electric field couplings of the sensor at each drive/pickup crossover.

FIG. 7 shows an example of an x-y grid of plate rows and columns depicted by lumped circuit components that represent the electric field couplings of the sensor at each drive/pickup crossover.

The bottom plates 706a,b,c etc. are driven one at a time by AC signal source 716 via switch matrix 740a-n. FIG. 7 shows a scan snapshot where one drive switch 740b in the on condition connecting the corresponding plate to the signal source. This activates one entire row 706b with AC signal over the entire length of the plate that is equal to the sensor width in one dimension. Correspondingly each top plate 702a,b,c etc. will pick up AC signal through insulating layer 704 and coupling capacitors 761a,b,c . . . n. Only one pickup plate at a time is active being switched into the buffer amplifier 717. Top Plate 702b is shown as the active plate in FIG. 7, while all or substantially all other pickups are shorted to ground via switch matrix 730a-n, thus the information from one x-y pixel is captured.

A single row remains active only as long as it takes the entire number of pickup plates/columns to be scanned. Scan time per pixel will depend on the frequency of operation and the settling time of the detection electronics, but there is no need to scan unduly fast as is typical with prior art swipe sensors. On the other hand prior art swipe sensors must scan at a very high pixel rate in order not to lose information due to undersampling relative to the finger speed that can be greater than 20 cm/sec. This reduction in capture speed relative to a swipe sensor relaxes the requirements of the analog electronics and greatly reduces the data rate that a host processor must capture in real time. This not only reduces system cost but allows operation by a host device with much less CPU power and memory. This is critical especially for mobile devices.

Once an entire row 706b has been scanned by all or substantially all of its corresponding pickup plates 702a-n, then the next row in the sequence is activated through switch matrix 740. This process continues until all or substantially all of the rows and columns are scanned.

The amount of signal that is coupled into the buffer amplifier 717 is a function of how much capacitance is formed by the insulating layer and the finger ridge or valley in close proximity. The detailed operation of how these electric fields radiate is shown in FIGS. 6a and b. The total coupling capacitance is a series combination of the insulating layer capacitance 704 that is fixed for a given thickness, and the variable topological capacitance of the object being sensed. The variable portion of this is shown in FIG. 7 as a series of variable capacitors numbered 760a-n, 761a-n, 762a-n etc., forming a two dimensional array.

Figure 8:
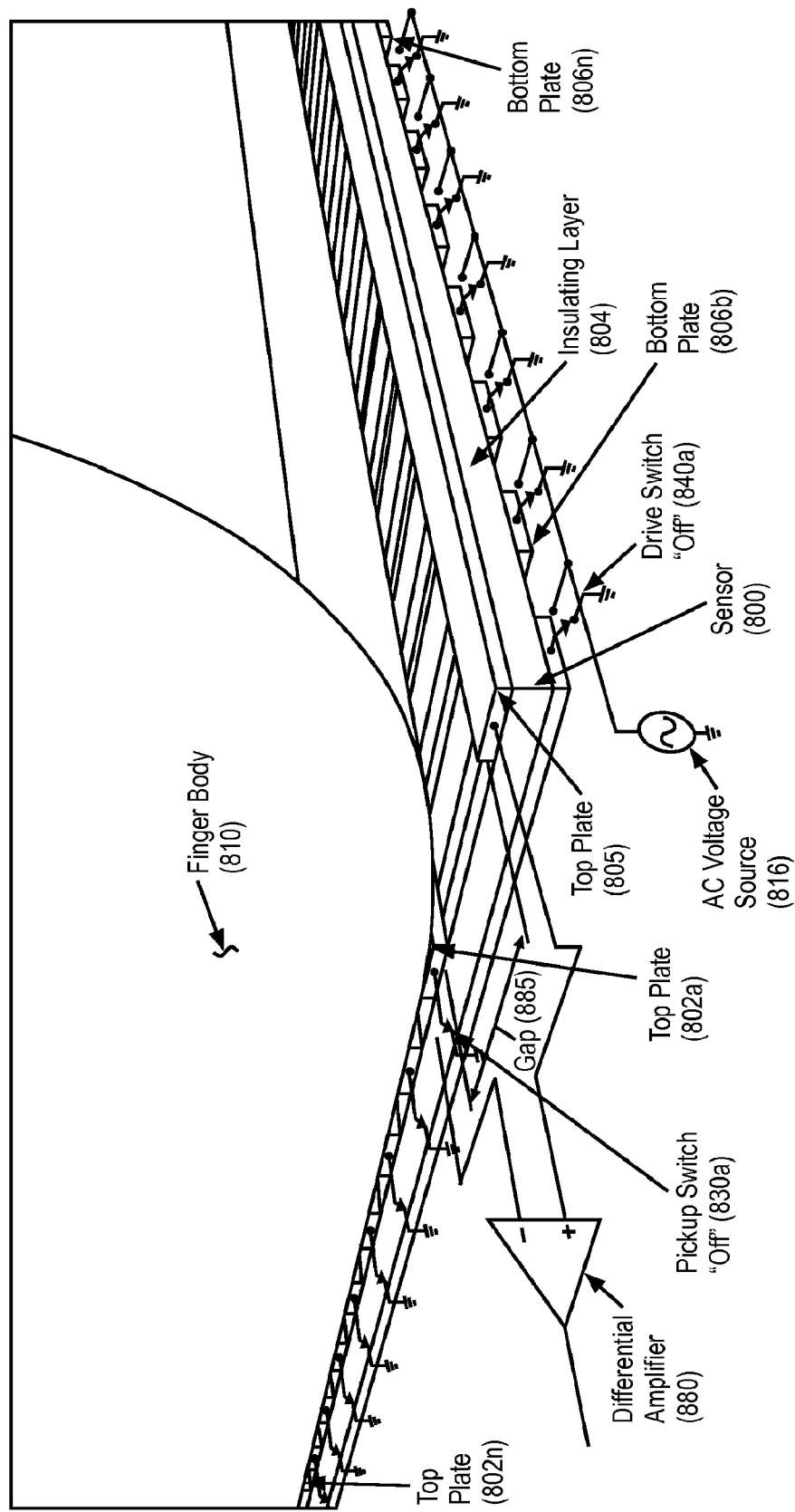
FIG. 8 shows an example of an embodiment of the placement embodiment using a differential amplifier to take the signal from the selected pickup plate and subtract it from a reference signal plate for noise reduction purposes.

FIG. 8 shows an example of an embodiment of the placement sensor using a differential amplifier 880 to take the signal from the selected pickup plate (802a-n), and subtract it from the reference signal of plate 805. The electrical subtraction of these signals performs several functions: first wide band common mode is subtracted out; second, subtracting against reference plate 805 provides a relative reference signal equivalent to an ideal ridge valley; third, common mode carrier signal that couples into both plates other than through a finger is also subtracted out. First order carrier cancellation of etch variation in the pickup plates also occurs when we subtract out carrier that is coupled in by other means than through fingers placed on the sensor. This is critical for high volume manufacturing at a low cost.

Reference plate 805 is intentionally located outside of the finger contact area of the sensor, separated from pickup plates 802a-n by Gap 885, Gap 885 is much larger that the nominal gap between the pickup plates that is typically 50 μm. In a real world embodiment plate 805 would be positioned under the plastic of a bezel to prevent finger contact, placing it at least 500 μm apart from the other pickup plates.

Each one of the pickup plates 802a-n is scanned sequentially being switched through pickup switches 830a connecting them to Differential Amplifier 880. During the scanning process of an entire pickup row, the positive leg of the differential amplifier remains connected to reference plate 805 to provide the same signal reference for all of the pickup plates.

Figure 9A:
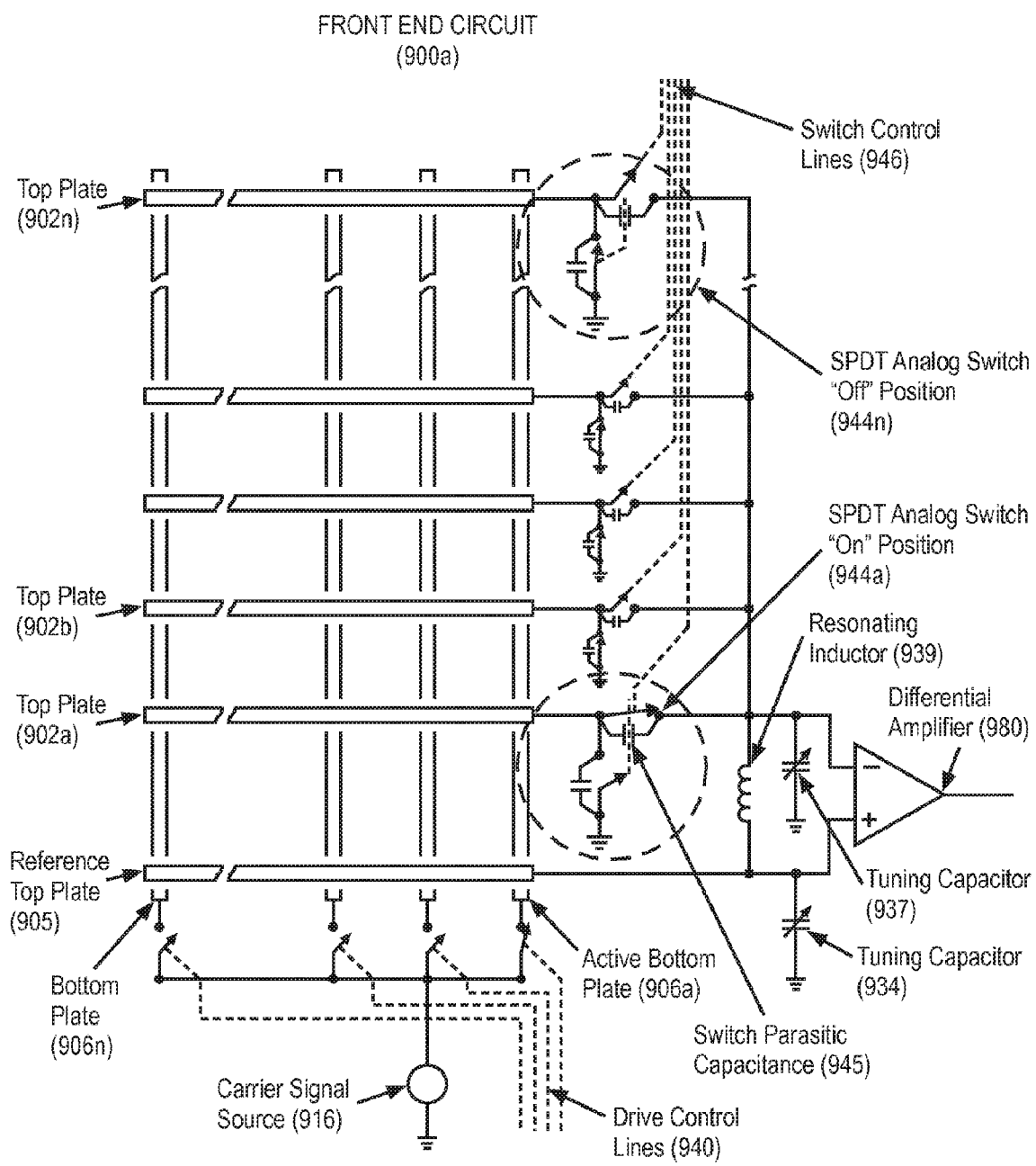
FIG. 9A shows the drive and sense multiplexing circuitry of an embodiment that incorporates a tank circuit to compensate for input loading effects.

FIG. 9A shows a circuit diagram of an example of a front end circuit 900a for the placement sensor in a topology that uses a bank of Single Pole Double Throw Switches or SPDTs to scan the pickup plate rows and a bank of Single Pole Single Throw switches to multiplex the drive plate columns.

In FIG. 9A we see a snapshot of the analog switches as the scanning process begins. Only the first SPDT switch 944a is shown in the "on" position, which allows pickup plate 902a to conduct its plate signal into Differential Amplifier 980. The remaining pickup plates are shorted to ground via switches 944, preventing any pickup signal received by them from entering into differential amplifier 980.

Each SPDT has a Parasitic Capacitance 945, due to the fact that real world switches do not give perfect isolation. In fact the amount of isolation decreases with frequency, typically modeled by a parallel capacitor across the switch poles. By using a SPDT switch we can shunt this capacitance to ground when an individual plate is not active. Since there is a large array of switches equal to the number of pickup plates, typically 200 for a 500 dpi sensor, the effective shunt capacitance to ground is multiplied by that number. So if a given switch has 0.5 picofarads of parasitic capacitance and there were 200 pickups, that would add up to 100 picofarads of total shunt capacitance.

In order to prevent this large capacitance from diverting most of the received signal from the active pickup to ground, it is desirable in this example to use a compensating circuit. This is accomplished by using resonating inductor 939, forming a classic bandpass filter circuit in conjunction with parasitic capacitors 945 (one per switch) and tuning capacitors 934 and 937. A two-step null & peak tuning calibration procedure is used where tuning capacitor 934 and 937 are individually tuned with inductor 939 using the same drive signal on both the plus and minus inputs to differential amplifier 980. The two bandpass filters formed with inductor 939 and resonating capacitors 934, and 937 respectively, will be tuned to the same center frequency when there is zero signal out of differential amplifier 980. Next capacitors 934 and 937 and inductor 939 are tuned together using a differential input signal with opposite 180 degrees phases on the plus and minus inputs to the differential amplifier 980. They are incremented in lock step until the exact drive carrier frequency is reached, this occurs when the output of differential amplifier 980 is at its peak, making the center frequency equal to the exact frequency of the carrier drive signal 916.

In a systems implementation, a calibration routine would be performed before each fingerprint scan to minimize drift of this filter with time and temperature. The resonating inductor 939 needs to have a Q or Quality Factor of at least 10 to give the filter the proper bandwidth characteristics necessary to optimize the signal to noise ratio. Alternately, carrier source 916 may be a variable frequency source, and capacitors (937 and 934) may be fixed values. In this embodiment, tuning is accomplished by varying the frequency of source 916) until peak output is obtained from differential amplifier 980

Figure 9B:
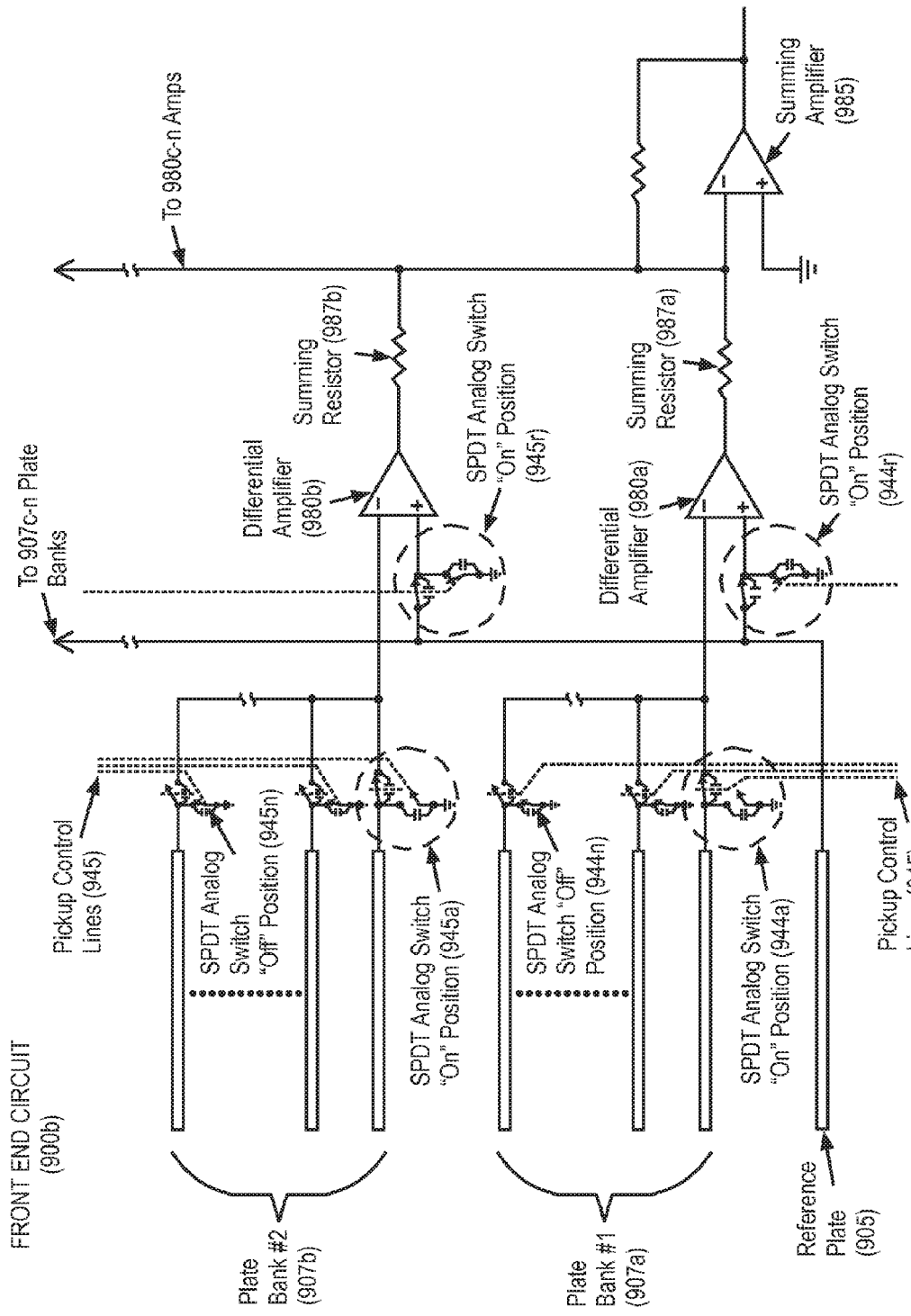
FIG. 9B shows the drive and sense multiplexing circuitry of an embodiment that incorporates cascaded buffers to minimize input loading effects.

FIG. 9B shows an alternate example of a front end circuit 900b employing multiple banks of plates grouped together, each with their own differential amplifiers.

Dividing up the large number of parallel pickup plates into groups each containing a smaller number of plates is an alternate architecture that would not require the use of a tuned bandpass filter in the front end because the parasitic switch capacitances would be greatly reduced. This would have two possible advantages, first lower cost, and second the ability to have a frequency agile front end. In this Figure we have a snapshot of the front end where the first switch 944a of bank 907a is active. All other switch banks 907b-907n are shown inactive, shorting their respective plates to ground. Therefore, only voltage or current differential amplifier 980a has any plate signal conducted into it, voltage or current differential amplifiers 980b-980n have both their positive and negative inputs shorted to ground through their respective switches 945a-n and 945r, preventing any signal from those banks making a contribution to the overall output.

Each of the differential amplifiers 980a-980n is summed through resistors 987a-987n into summing amplifier 985. Only the differential amplifier 980a in this snapshot has plate signal routed into it, so it independently produces signal to the input of summing amplifier 985. This process is repeated sequentially until all or substantially all of the switch banks 907a-n, and switch plates 944a-n, 945a-n, etc., of the entire array are fully scanned. In different embodiments, all or substantially all of the array may be scanned, or less than the entire array may be scanned in different applications. In some applications, a lower resolution may be desired, so all of the array may not need to be scanned. In other applications, a full image may not be necessary, such as a navigation application, where limited images may be used to detect movement of speed, distance and/or direction to use as input for a pointing device, such as directing a cursor on a display similar to a computer touch-pad or a mouse.

By splitting the pickup array up, the capacitive input load on each plate is reduced from that of the full array of switches to the number of switches within a given plate group. If we were to divide, for example, 196 potential pickup plates into 14 banks of 14 plates, the result would be a capacitance load equal to the parasitic capacitance of 14 switches (944), plus the capacitive load of the differential amplifier. If analog switches 944 are constructed with very low parasitic capacitance then the overall input load would be small enough not to need a bandpass circuit in the front end in order to resonate out the load capacitance. As integrated circuit fabrication techniques improve we would be able design smaller switches with less parasitic capacitance, making this approach become more attractive.

Figure 9C:
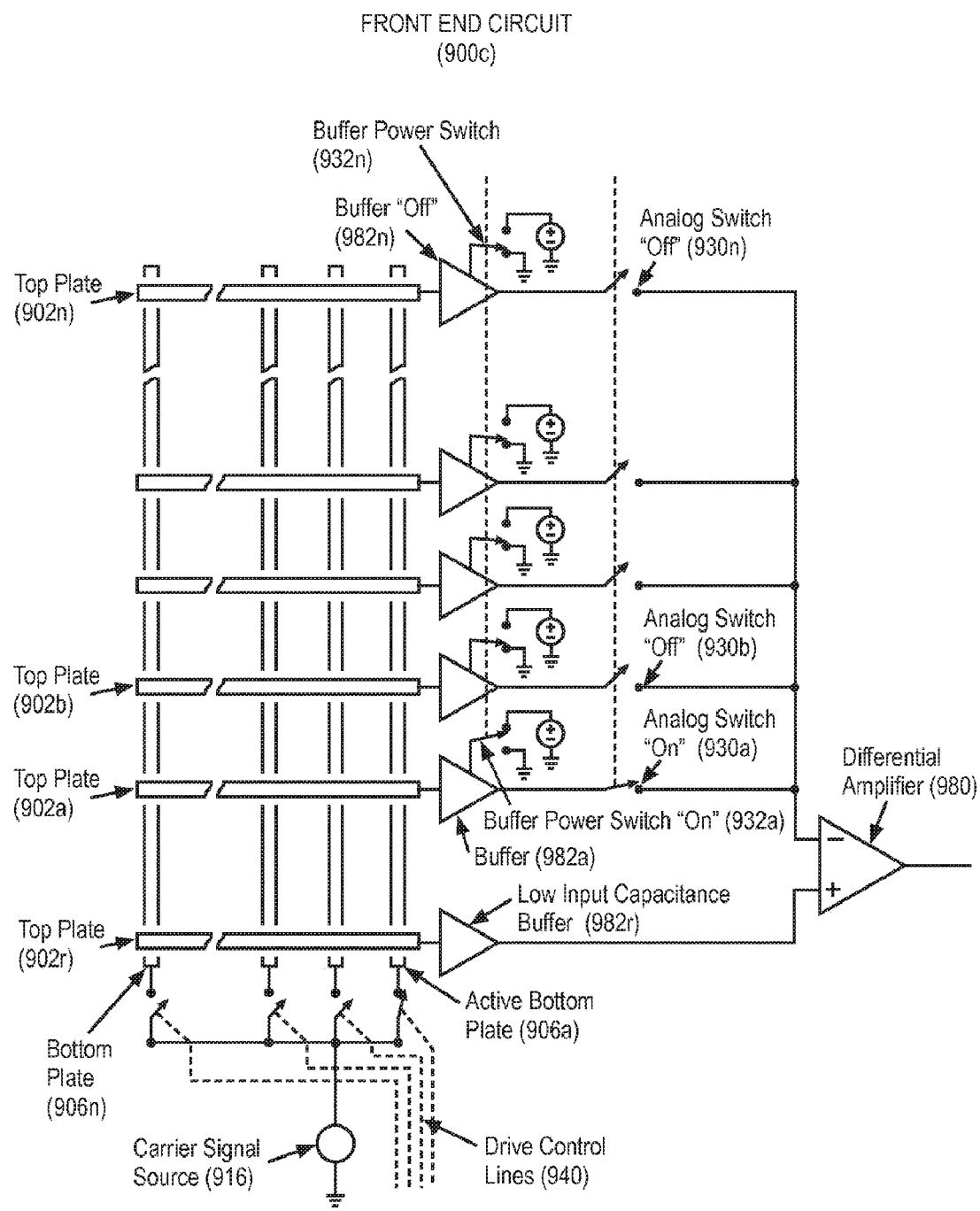
FIG. 9C shows the drive and sense multiplexing circuitry of an embodiment that incorporates dedicated buffers for each sense to minimize loading effects.

FIG. 9C illustrates another example of a front end circuit 900c using individual plate buffers that are multiplexed into a second stage differential amplifier.

Buffers 982a through 982n as illustrated are special buffers that are designed to have very low input capacitance. In one embodiment, these buffers could be configured as single stage cascaded amplifiers in order to minimize drain-to-gate Miller capacitance and die area. To better maximize plate to plate isolation, two sets of switches could be used for each input. Analog switches 930a-930n are included in this example to multiplex each selected buffer into differential amplifier 980. Switches 932a-n are included to shut down the power simultaneously to all the other input buffers that are not selected. This effectively puts them at ground potential. An alternate embodiment would be to put input analog switches in front of each amplifier to allow a short of the unused plates directly to ground. One effect of this approach may be an increase in input load capacitance for each plate.

FIG. 9C shows a snapshot of the scanning process where top plate 902a is being sensed though buffer 982a that has power supplied to it through switch 932a. Analog switch 930a is closed, routing it to differential amplifier 980. All other buffer outputs are disconnected from the differential amplifier 980 via analog switches 930b-n and power switches 932n

The positive input to differential amplifier 980 is always connected to the reference plate 902r (through low input capacitance buffer 982r), providing an "air" signal reference to the amp. The differential amplifier 980 serves to subtract out noise and common mode carrier signal in addition to providing a "air" reference carrier value.

Figure 10:
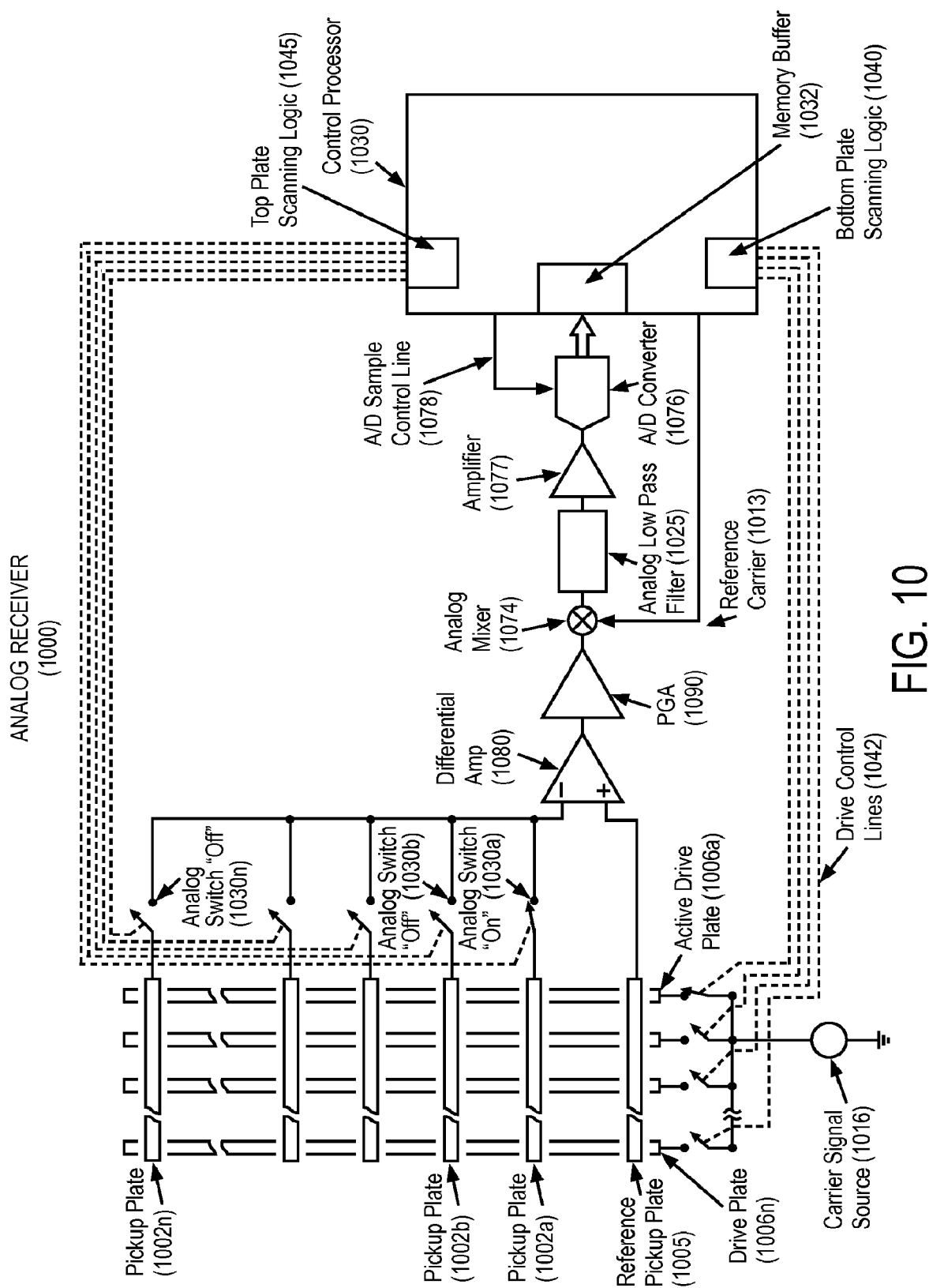
FIG. 10 shows an embodiment that incorporates an analog receiver to process the sensed signal, and processing circuitry to perform the drive and sense line scanning function.

FIG. 10 shows a particular embodiment of a placement sensor implemented with traditional analog receiver 1000 technology. The analog front end begins with Differential Amplifier 1080 where selected Pickup Plate 1002a-n is subtracted from reference pickup plate 1005, which is located outside the finger contact area providing a reference signal equivalent to an ideal finger valley. A programmable gain stage or PGA 1090 follows the Differential Amplifier 1080, but could be integrated into the same block providing both gain and subtraction in a single stage. PGA 1090 is designed to have a gain range wide enough to compensate for production variations in plate etching and solder mask thickness between the layers.

Control processor 1030 orchestrates the scanning of the two dimensional sensor plate array. Drive plates/columns 1006a-1006n are scanned sequentially by the bottom plate scanning logic 1040 in the Control Processor 1030 (via drive control lines 1042 connected to switches coupled to drive plates 1006a-n). When a selected drive plate is activated it is connected to carrier signal source 1016, all inactive drive plates are connected to ground. Before activating the next drive plate in the sequence the active drive plate remains on long enough for the entire row of pickup plates 1002a-n to be scanned by top plate logic 1045 controlling switches 1030a-n.

Analog mixer 1074 multiplies the gained up plate signal against the reference carrier 1013. The result is a classic spectrum of base band plus harmonic products at multiples of the carrier frequency. An analog low pass filter 1025 is employed to filter out the unwanted harmonics and must have a sharp enough roll off to attenuate the information associated with the second harmonic without losing base band information.

Following the low pass filter are an amplifier 1077 and an A/D Converter 1076, which must sample at at least twice the pixel rate to satisfy the Nyquist criteria. Memory buffer 1032 stores the A/D samples locally with sufficient size to keep up with the worst case latency of the host controller. The A/D Sample Control Line 1078 provides a sample clock for the converter to acquire the sequential pixel information that is created by the sequencing of the plate rows and columns.

Figure 11:
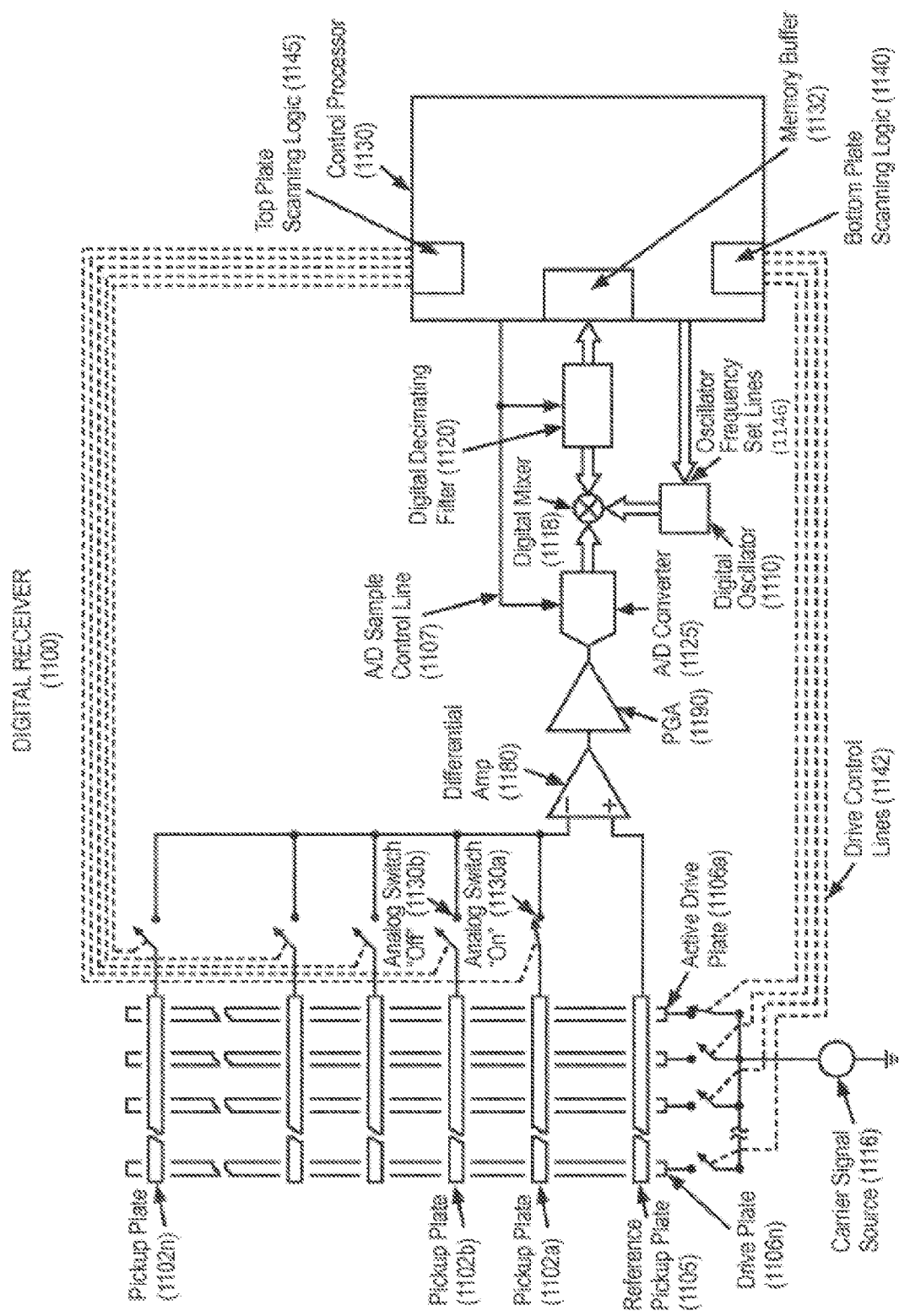
FIG. 11 shows an embodiment that incorporates a direct digital conversion receiver to process the sensed signal, and processing circuitry to perform the drive and sense line scanning function.

FIG. 11 shows an example of one embodiment of a placement sensor implemented with direct digital conversion receiver 1100 technology. In this example, the analog front end begins with Differential Amplifier 1180 where selected Pickup Plate 1102a-n is subtracted from reference pickup plate 1105, which is located outside the finger contact area providing a reference signal equivalent to an ideal finger valley. The electrical subtraction of these signals performs several functions: first wide band common mode is subtracted out; second, subtracting against reference plate 1105 provides a relative reference signal equivalent to an ideal ridge valley; third, common mode carrier signal that couples into both plates other than through a finger is also subtracted out. Elimination of common mode is particularly important in high RF noise environments. First order carrier cancellation of etch variation in the pickup plates also occurs when we subtract out carrier that is coupled in by other means than through fingers placed on the sensor. This is critical for high volume manufacturing at a low cost.

A programmable gain stage or PGA 1190 follows the Differential Amplifier, which could easily be combined into a single differential amplifier including programmable gain as is commonly done in modern integrated circuit design. PGA 1190 is designed to have a gain range wide enough to compensate for production variations in plate etching and solder mask thickness between the layers.

Control processor 1130 orchestrates the scanning of the two dimensional sensor plate array. Drive plates/columns 1106a-1106n are scanned sequentially by the bottom plate scanning logic 1140 in the Control Processor 1130 (via drive control lines 1142 connected to switches coupled to drive plates 1006a-n). When a selected drive plate is activated it is connected to carrier signal source 1116, all inactive drive plates are connected to ground. Before activating the next drive plate in the sequence the active drive plate remains on long enough for the entire row of Pickup Plates 1102a-n to be scanned by top plate scanning logic 1145 controlling switches 1130a, 1130b, etc., and captured by the A/D converter 1125.

The A/D Converter 1125 is sampled at a rate of at least twice the carrier frequency to satisfy the Nyquist criteria. The A/D Sample Control Line 1107 provides a sample clock for the converter to acquire the sequential pixel information that is created by the sequencing of the plate rows and columns.

Following the A/D converter 1125 is a Digital Mixer 1118 that digitally multiplies the A/D output that is at the carrier frequency against the reference carrier generated by the Digitally Controlled Oscillator 1110. The result is that the signal is down converted to the base band with the carrier removed. There are other unwanted spectral components created by this process, namely a double time carrier side band, but these can easily be filtered out.

A combination decimator and digital filter 1120 follows the Digital Mixer 1118. This block performs sampling down conversion, reducing the sample rate from at least twice the carrier frequency to at least twice the pixel rate that is much lower. The digital filter would typically include a Cascaded Integrator Comb, or CIC filter, which removes the unwanted spectral byproducts of mixing as well as improving the receiver signal to noise. A CIC filter provides a highly efficient way to create a narrow passband filter after mixing the signal down to baseband with the digital mixer. The CIC filter may be followed by a FIR filter running at the slower decimated rate to correct passband droop.

With a reduction of sample rate in the order of 100:1 a relatively small Control Processor Buffer (1132) could be used to capture and entire fingerprint. For example a 200× 200 array producing 40 k pixels could be stored in a 40 kb buffer. This is in contrast to a swipe sensor that must scan the partial image frames at a rate fast enough to keep up with the fastest allowable swipe speed, usually around 200 ms. At the same time, a slow swipe of two seconds must also be accommodated, requiring ten times the amount of memory as the fastest one. Various techniques have been developed to throw away redundant sample lines before storage, but even with that the real time storage requirements are much greater for swipe sensors. This is a critical factor in Match on Chip applications where memory capacity is limited. In addition, a placement sensor has no real-time data acquisition or processing requirements on the host processor beyond the patience of the user for holding their finger in place.

Figure 12A:
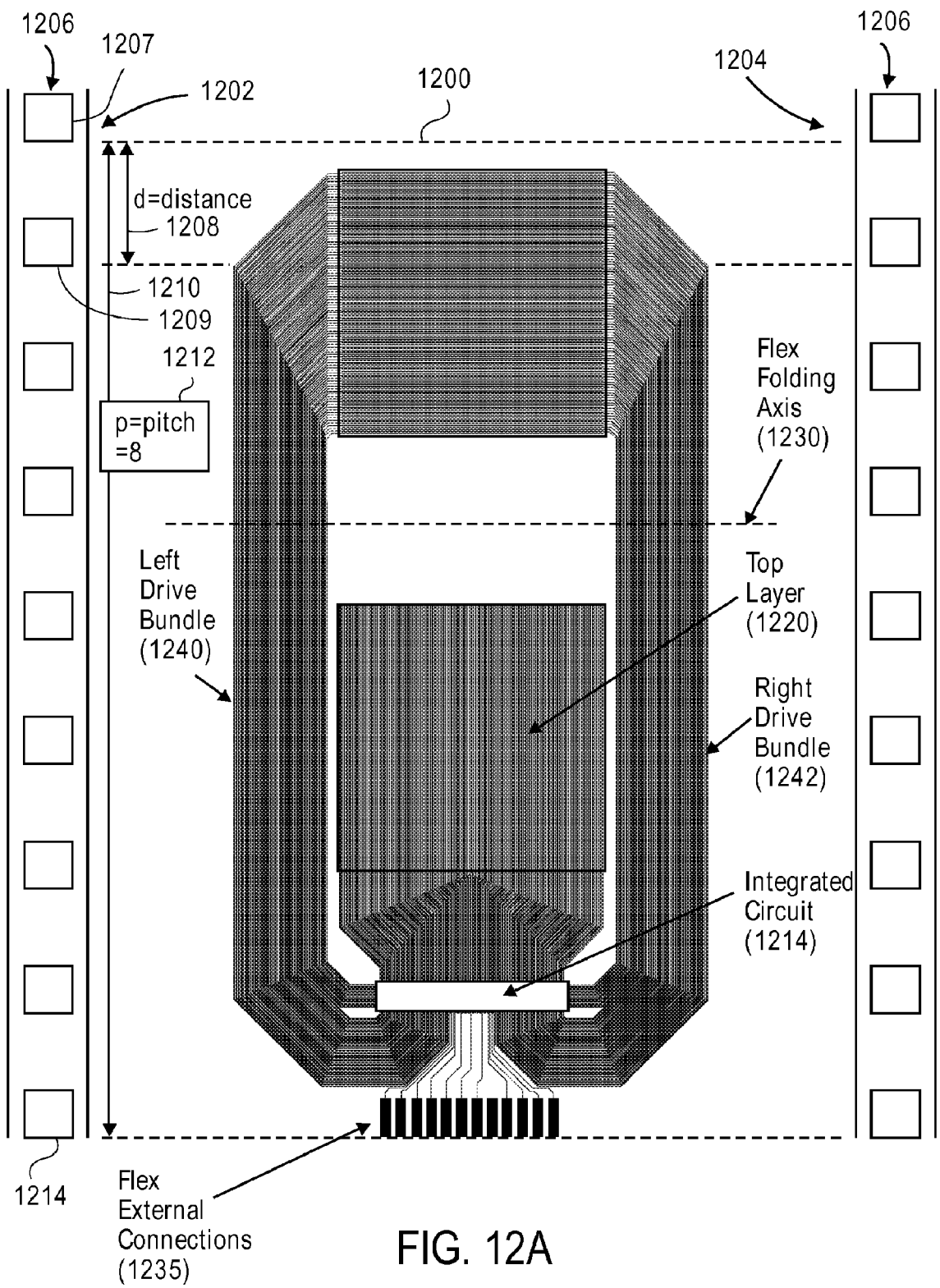
FIG. 12A shows one example of a layout of the drive and sense traces for an embodiment that incorporates the folded aspect of the embodiment laid out flat prior to folding.

Referring to FIG. 12A, and example of a sensor layout 1200 configured according to one embodiment is illustrated in a configuration that is known in the semiconductor industry as a Chip on Flex (CoF). Chip on Flex is a configuration where a processor chip is attached to a flexible substrate, such as Kapton® tape, and that is electrically connected to conductive lines and possibly other components located on the flexible substrate. In this example, the sensor layout 1200 is shown within the borders of Kapton® tape having pitch rails 1202, 1204 with slots 1206 located along both rails. These slots are used in the manufacturing process to feed the tape through the process while lines and possibly components are formed on the tape. The pitch of a device refers to the length of Kapton® tape required to form a device on the CoF. The distance "d" 1208, measured here between slots 1207 and 1209, is substantially constant throughout each rail, and the pitch is a shorthand method of determining the length of flex that a device covers. For the device shown in this example, the pitch 1212 shows a span between slot 1207 and 1214 of eight slots, and thus would be characterized as an 8-pitch device. The example sensor device shown, which may be a fingerprint sensor or other type of placement, 2D or area sensor, illustrates an integrated circuit 1210, which may be a logic circuit formed on a silicon substrate, a microprocessor, or other circuit for processing pixel information captured from a sensor circuit. The example may also be formed or otherwise manufactured on a substrate other than flexible substrate or Kapton® tape, in fact it may be formed on a silicon substrate, rigid board, or other substrate configured for various applications.

If configured as a fingerprint sensor or other placement sensor, integrated circuit 1210 may be a mixed signal chip that enables all or some of the functions described in FIG. 16 below. In one embodiment, it has enough inputs and outputs to drive a 200 by 200 line array of drive and pickup lines, and may have more or less of either lines. The top layer 1220 is formed by an array of pickup lines connected directly to integrated circuit 1210. This may be a flip chip mounted directly to the flex substrate without bond wires. In this example, the bottom layer is formed by folding the single layer back onto itself along the folding axis 1230 to a create double layer active sensor area. The drive lines fold to create the bottom layer 1225. The drive lines in this example are split into left and right groups 1240 and 1242 respectively for the sake of layout balance, but could be all on the left or right side of the sensing area. The left drive plate bundles 1240, and right drive plate bundles 1242 are inter-digitated with alternating left and right feeds to form a continuous line array on bottom layer 1225.

Flexible substrate based connector 1235 routes power, ground and interface signals out to an external host or onto another substrate that contains system level components, such as those illustrated in FIG. 16 and described below. These components may include but are not limited to a processor with memory, logic enabling imbedded matching algorithm(s) and encrypting/decrypting functions. In an alternative example, connector 1235 may be attached to the host substrate using conductive adhesive otherwise known as anisotropic conductive film (ACF attach), which may be labeled as "high density" in some products.

Referring to FIG. 12B, another example of a sensor 1250 is shown having a different orientation and configuration on a substrate. Similar to the above example, the sensor 1250 is a placement sensor, and is configured to be folded onto itself along the folding axis 1251 to create two layers, the bottom layer 1252 with drive lines 1256, and top layer 1254, with pickup lines 1257, integrated circuit 1258, flex external connections 1262, and processor connections 1260 that may be used to connect the integrated circuit to external devices, such as for manufacturing testing for example. This configuration, however, has a much smaller pitch, again where the distance "d" is the distance between each pair of slots 1206, and the pitch in this example is between slots 1270 and 1272, making this device a 5-pitch device. This example device takes up 5 pitches of Kapton® tape compared to the other example device 1200 (FIG. 12A) taking up 8 pitches of Kapton® tape. This device performs substantially the same function as that of example 1200, FIG. 12A, yet takes up less Kapton® tape, saving in material costs. The device may take up even less pitches of tape if the size of the resulting sensor surface were reduced, allowing the space needed to accommodate the pickup lines, drive lines, and other components to be reduced. In this example, the effective sensor surface may be ten square millimeters, and could be reduced to nine or even eight millimeters, and the structures could be reduced accordingly to reduce the overall area of the device, likewise reducing the area of substrate required to accommodate the overall device.

As will be appreciated by those skilled in the art, given these examples, different designs may be accomplished to optimize different aspects of the invention, including size of the substrate used for a device, and both the size and pixel density of the sensing area. The invention, however, is not limited to a particular optimization done by others, and indeed the invention should inspire others to improve upon the design using well known and alternative processes, materials, and know-how available to them. The scope of the invention is only limited by claims that are either appended or submitted for examination in the future, and not by information that is extemporaneous to this specification.

Figure 13A:
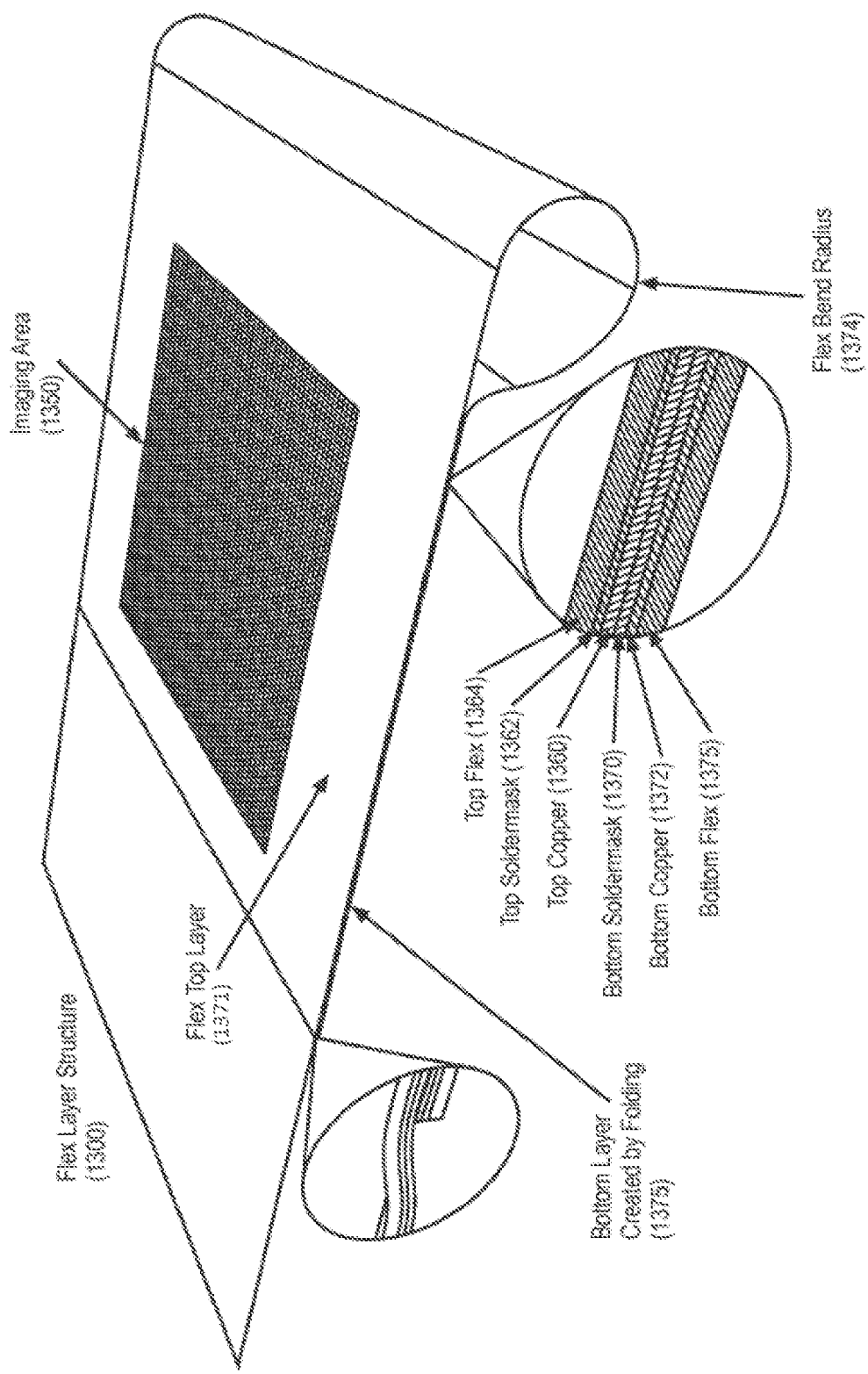
FIG. 13A shows the layer stack-up of an embodiment that incorporates the folding aspect subsequent to folding.

Referring to FIG. 13A, an illustration of a flex layout structure 1300 is illustrated. As shown, the flex layer structure 1300 includes an imaging area 1350, in which drive lines form crossover locations with pickup lines, where the crossover locations are formed by folding the top layer 1371 over bottom layer 1375, folding the flexible substrate upon itself about flex bend radius 1374. From a side view, the top flex 1364 is layered over top soldermask 1362, which is layered upon top copper or pickup lines 1360. Bottom layer solder mask 1370 is folded under top copper 1360, and bottom copper 1372 is formed under solder mask 1370 and over bottom flex 1375.

Figure 13B:
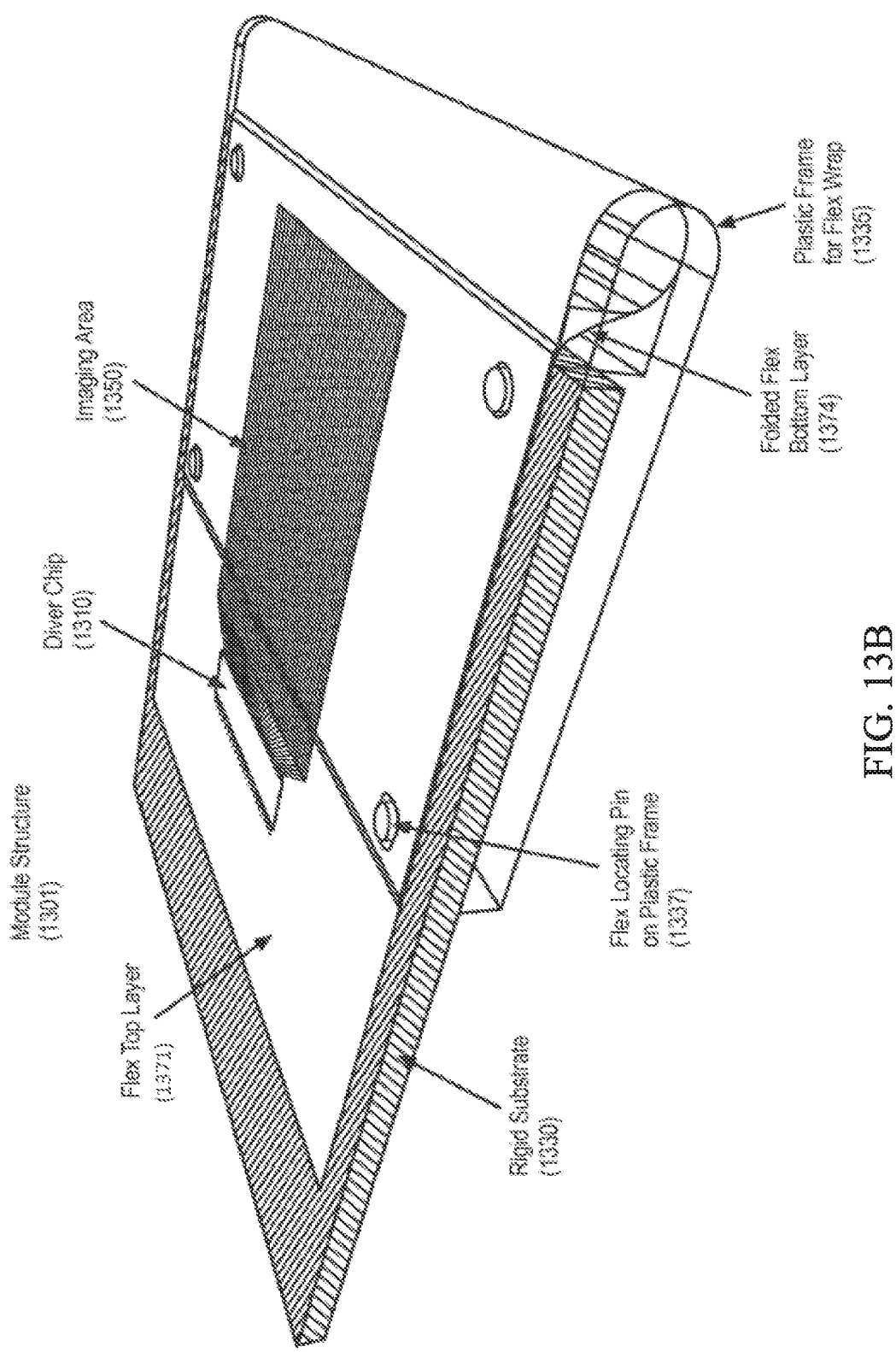
FIG. 13B shows an embodiment that incorporates the folding aspect subsequent to folding and assembly into a rigid module.

Referring to FIG. 13B, an example of a module structure 1301 is shown for mounting the flex layer structure 1300 of FIG. 13A. Those skilled in the art will understand that the structure of a particular module may vary according to the embodiment, and that this example, though it shows a substantially complete example of a module that can be used to base a practical implementation, is but one example and is not intended and should not be considered as limiting the embodiment in any way. The example structure 1301 includes rigid substrate 1330 that receives the flex top layer 1371 on its top layer with flex locating pins or plastic frame 1337 configured to ensure alignment of the drive plates with the pickup plates. Because the sensing electrode pairs are formed by crossovers of the drive and pickup lines on the two layers, the x-y alignment tolerance requirements may be on the order of several pixels, rather than the sub-pixel alignment tolerances that would be required if there were features to be matched between the two layers. The four mounting holes (1337) on each layer are sufficient to ensure angular and x-y alignment. Also illustrated is driver chip 1310 and imaging area 1350.

Figure 14:
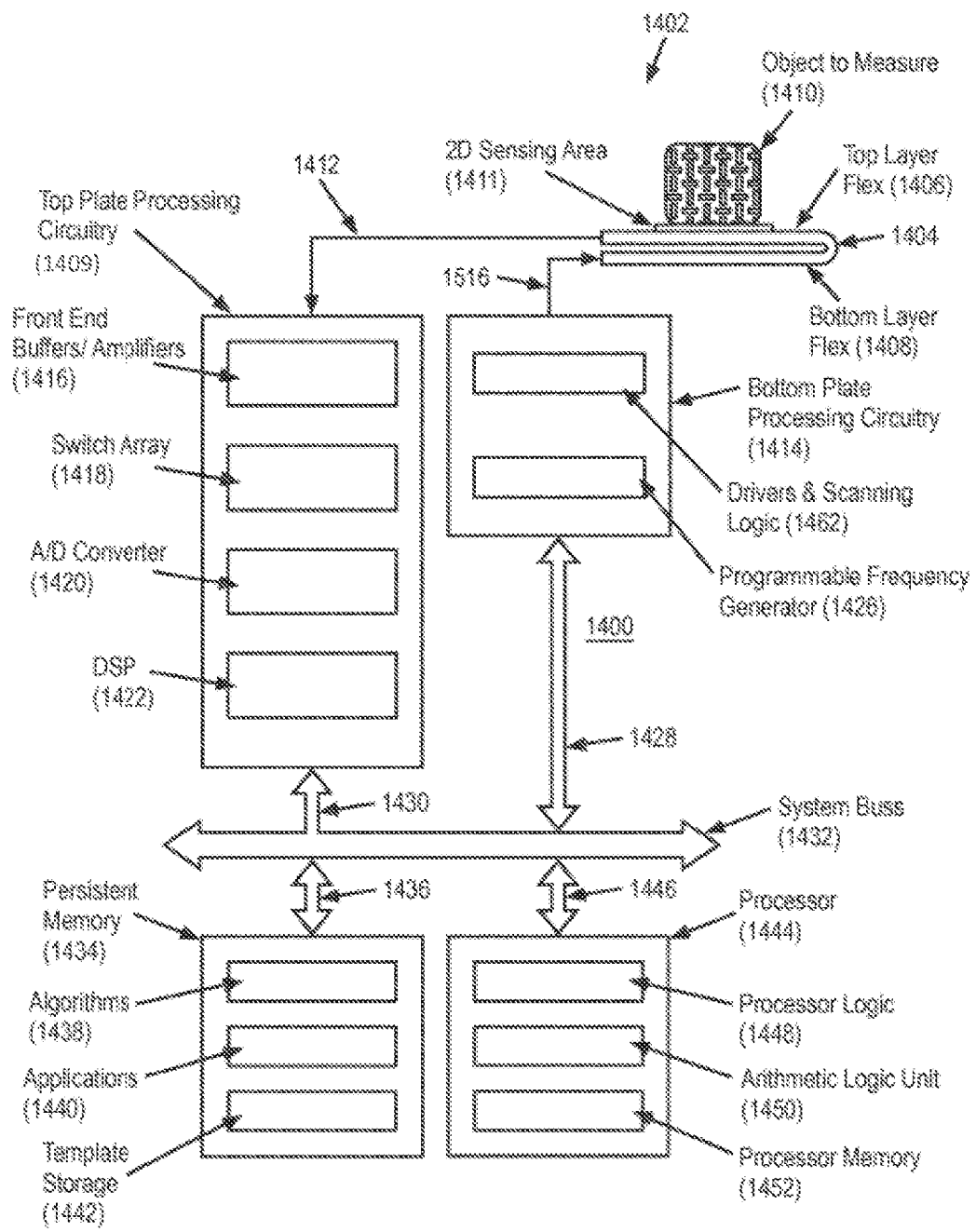
FIG. 14 shows a sensor system configured according to the embodiment for the purpose of sensing features of an object.

Referring to FIG. 14, an illustration is provided of an example system 1400 incorporating a sensor system 1402 generally configured according to the embodiment. A sensor device may be incorporated into a system, or may be configured as a stand-alone product. As a stand-alone product, the sensor components may be encased in a housing (not shown), and electrical connections exposed for connection to a device or system that would utilize such a device. Those skilled in the art will immediately see how a sensor configured according to the embodiment as described herein can be incorporated into a housing such as those widely used in different industry sectors. Thus, for example, in a system, the mechanical connections, designs and structures may necessarily vary according to a particular application. For example, if incorporated into a laptop for use as a fingerprint sensor, a surface mounting module would need to be employed to expose the sensor grid lines to a user. If incorporated into a mobile phone, personal data assistant (PDA) or the like, another type of mounting module would be needed to conform to the particular device design while providing the operational capability of the sensor. Again, FIG. 14 illustrates a diagrammatic representation of a system 1400 that incorporates a sensor 1402 configured according to the embodiment with the folded flexible or rigid substrate 1404 having a top layer 1406 and a bottom layer 1408, and each having either pickup lines or plates and drive lines or plates respectively depending on the application, though not shown here. The two-dimensional sensing area 1411 is shown with an object 1410 on top, which may be a finger in the case of a fingerprint sensor, or another object in another application. The top layer's pickup plates or lines (not shown) communicate with top plate processing circuitry 1409 via communication link 1412 to send resultant signals received. Drive lines or plates are located but not shown here on bottom layer 1408, and receive drive signals from bottom plate processing circuitry 1414 via communication line 1416. The top plate processing circuitry 1409 includes front end buffers and amplifiers 1416 configured to receive, amplify and/or buffer or store a resultant signal received from the pickup plates or lines. A switch array 1418 such as illustrated in FIGS. 9A-9C is configured to receive the signal from the front end 1416 and send the switched signal to analog to digital (A/D) converter 1420 for conversion to a digital signal. Digital signal processor (DSP) 1422 is configured to receive the digital signal from A/D converter 1420 and process the signal for transmission.

Bottom plate processing circuitry 1414 is configured to produce a drive signal for use by drive plates or lines located on the bottom layer 1408 of the sensor substrate 1404, and includes drivers and scanning logic 1462 for producing the signal, and programmable frequency generator 1426 for programmably setting the frequency in which the drive signal is set. The bottom plate processing circuitry 1414 includes communication link 1428, likewise, top plate circuitry has communication link 1430 for communicating with system buss 1432 for sending and receiving communications among the system, such as to processors, memory modules, and other components. System buss 1432 communicates with persistent memory 1434 via communication link 1436 for storing algorithms 1438, application software 1440, templates 1442, and other code for persistent and frequent use by processor 1444. Processor 1444 includes processor logic 1448 having logic and other circuitry for processing signals received from the system buss and originating from the sensor 1402, and also includes arithmetic logic unit 1450 configured with logical circuits for performing basic and complex arithmetic operations in conjunction with the processor. Processor memory 1452 is configured for local storage for the processor 1444, for example for storing results of calculations and retrieval for further calculations.

In operation, drive signals are controlled by processor 1444, and parameters for the drive signals originating from bottom plate processing circuitry 1414 are set in the bottom plate processing circuitry 1414 by the processor 1444. Drive signals are generated by logic 1462 within the parameters set in generator 1426 and sent to bottom plate 1408 via communication link 1516. These signals generate electromagnetic fields that extend to pickup lines on top layer 1406 about the sensing area 1411. These signals are cycled through different pixel electrode pairs on the sensor grid (not shown here, but described above.), and some of these electromagnetic fields are absorbed by the object 1410 (such as a fingerprint for example). The resultant signal is picked up by the pickup plates or lines located on top layer 1406 about the sensing area (not shown here, but described above). The resultant signal is then transmitted to top plate processing circuitry 1409 via communication line 1412, and the signal is processed and transmitted to storage or processor 1444 for further processing. Once the drivers and scanning logic have cycled through the pixels on the grid sensor, data related to features and characteristics of the object can be defined and utilized by the system. For example, in a fingerprint sensor system, the image may be a fingerprint image that can be compared to a stored fingerprint image, and, if there is a match, it can be used to validate a user.

Figure 15:
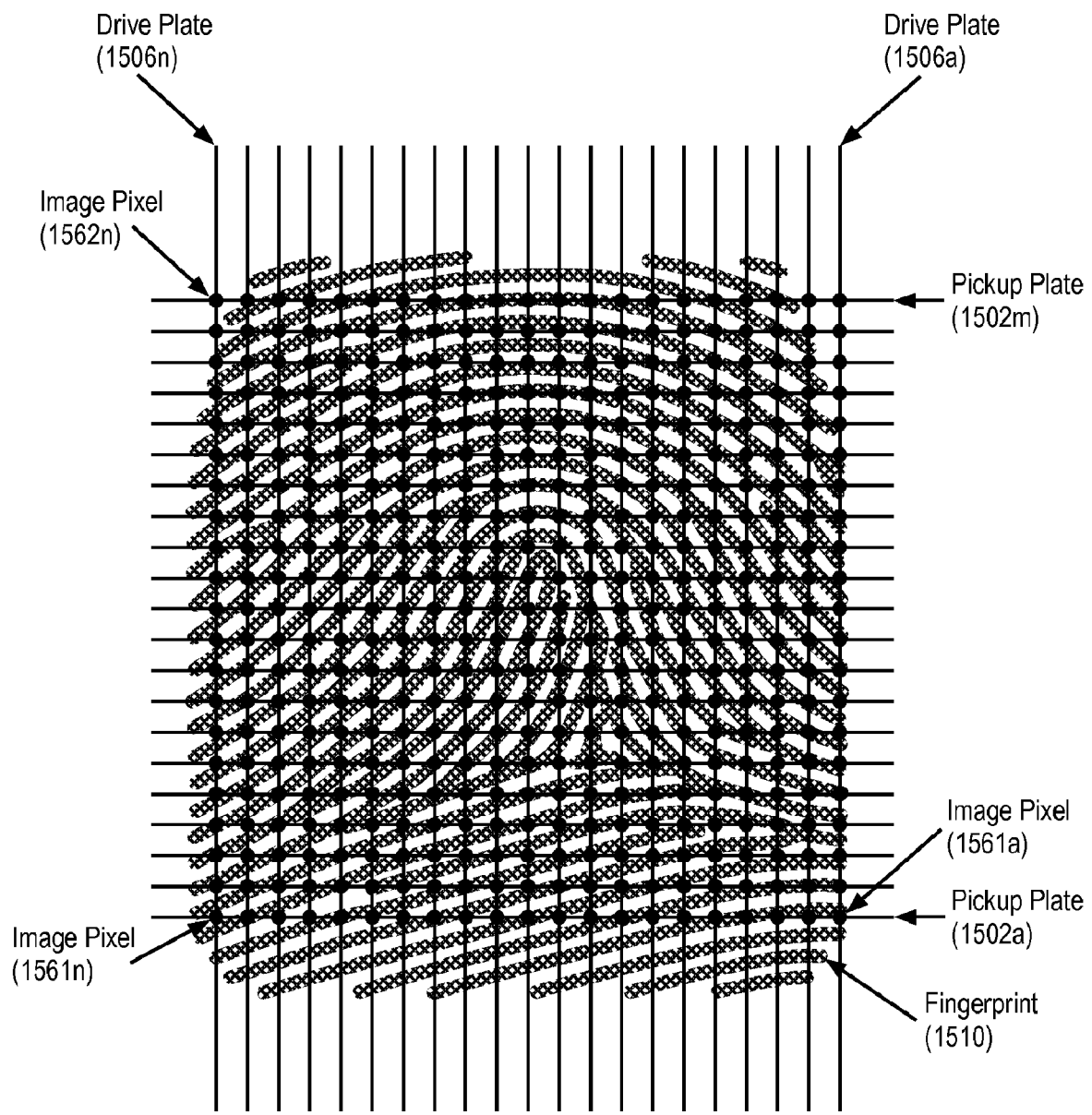
FIG. 15 shows an example of the sensing of a fingerprint features.

FIG. 15 Illustrates how a device configured according to the embodiment may be applied to a fingerprint sensing application. A user places a finger with fingerprint (1510) over the sensor grid, which is formed by the crossover locations of the drive plates (1506a-1506n) and the pickup plates (1502a-1502m). Image pixel 1561a senses the fingerprint area above the electrode pair of drive plate 1506a and pickup plate 1502a, pixel 1561a senses the crossover of drive 1506n and pickup 1502a, and pixel 1562n senses the area above the crossover of drive 1506n and pickup 1502m.

Figure 16:
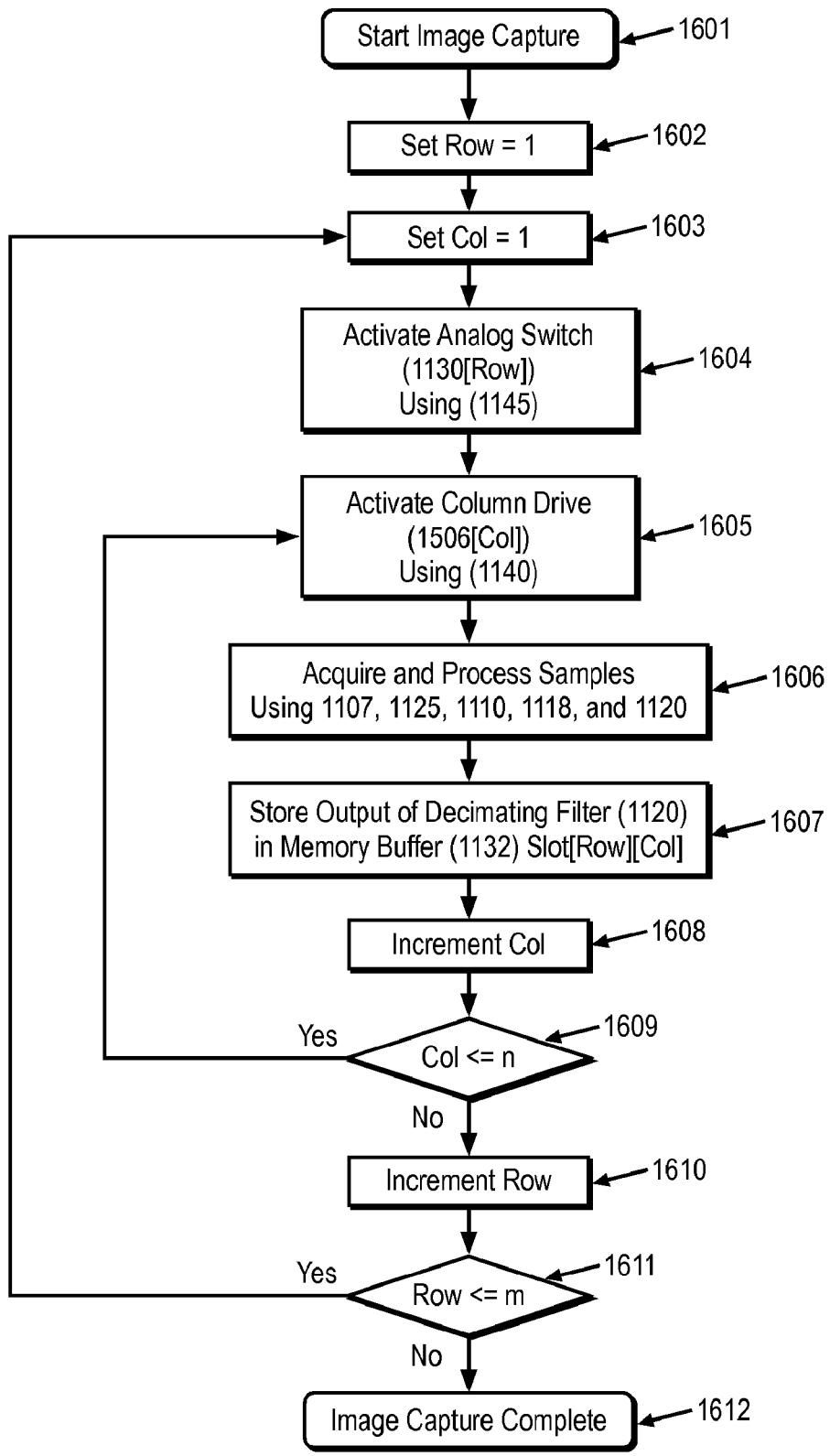
FIG. 16 shows the process flow steps required to collect a 2-dimensional image with a sensor system configured according to one embodiment.

FIG. 16 illustrates the steps required to collect the fingerprint image as shown in FIG. 15, using the embodiment shown in FIGS. 11 and 14. Image capture begins at step 1601. As part of the initialization a row counter is initialized to 1 at step 1602. Step 1603 is the beginning of a row scan sequence. At the beginning of each row, a column counter is set to 1 at step 1603. In step 1604, the top plate scanning logic 1145 activates the appropriate analog switch (one of 1103a through 1103n) for the selected row. In Step 1605 the sense of an individual pixel begins when the bottom plate scanning logic 1140 activates the appropriate drive plate (one of 1106a through 1106n) with the carrier signal 1116. At step 1606 the signal from differential amplifier 1180 is sampled repeatedly by A/D converter 1125 after processing through programmable gain amplifier 1190. Digital mixer 1118 mixes the samples down to the baseband frequency set by digital oscillator 1110. The baseband signal is then filtered by digital decimating filter 1120 to produce a signal level value for the current pixel. The functions performed for this step in the embodiment of FIG. 11 could alternatively be performed by the corresponding analog receiver shown in FIG. 10, or other functionally similar arrangements. In step 1607 the signal level value derived in step 1606 is stored in the appropriate position in memory buffer 1132 that corresponds to the currently selected row and column. In step 1608 the column number is incremented, and in step 1609 the column number is tested to determine whether the current row collection has been completed. If the row has not been completed, we return to step 1605 to collect the next pixel in the row. If the row is complete, we proceed to step 1610 and increment the row number. In step 1611, we test the row number to determine if all the rows have been scanned. If not, flow returns to 1603 to start the next row back at the first column. Once all the rows have been scanned, image capture is complete, and we proceed to step 1612, at which point the image is ready for further processing or transfer to long term storage.

Those skilled in the art will recognize that row and column scanning order may not correspond directly to physical position in the array, as some implementations may more optimally be sampled in interleaved fashions.

Figure 17A:
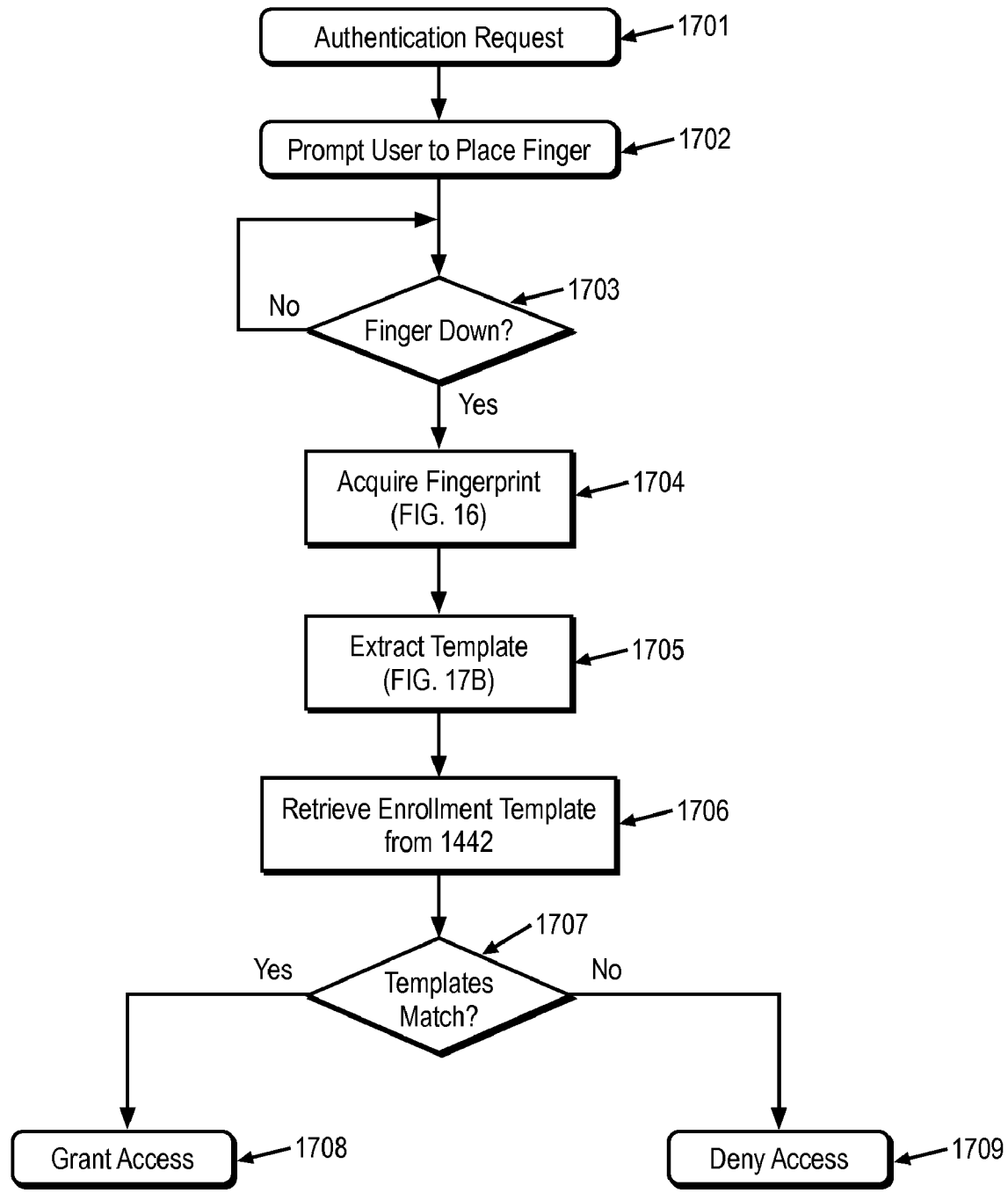
FIG. 17A shows the process flow steps required to authenticate a user with a fingerprint sensor system configured according one embodiment.
Figure 17B:
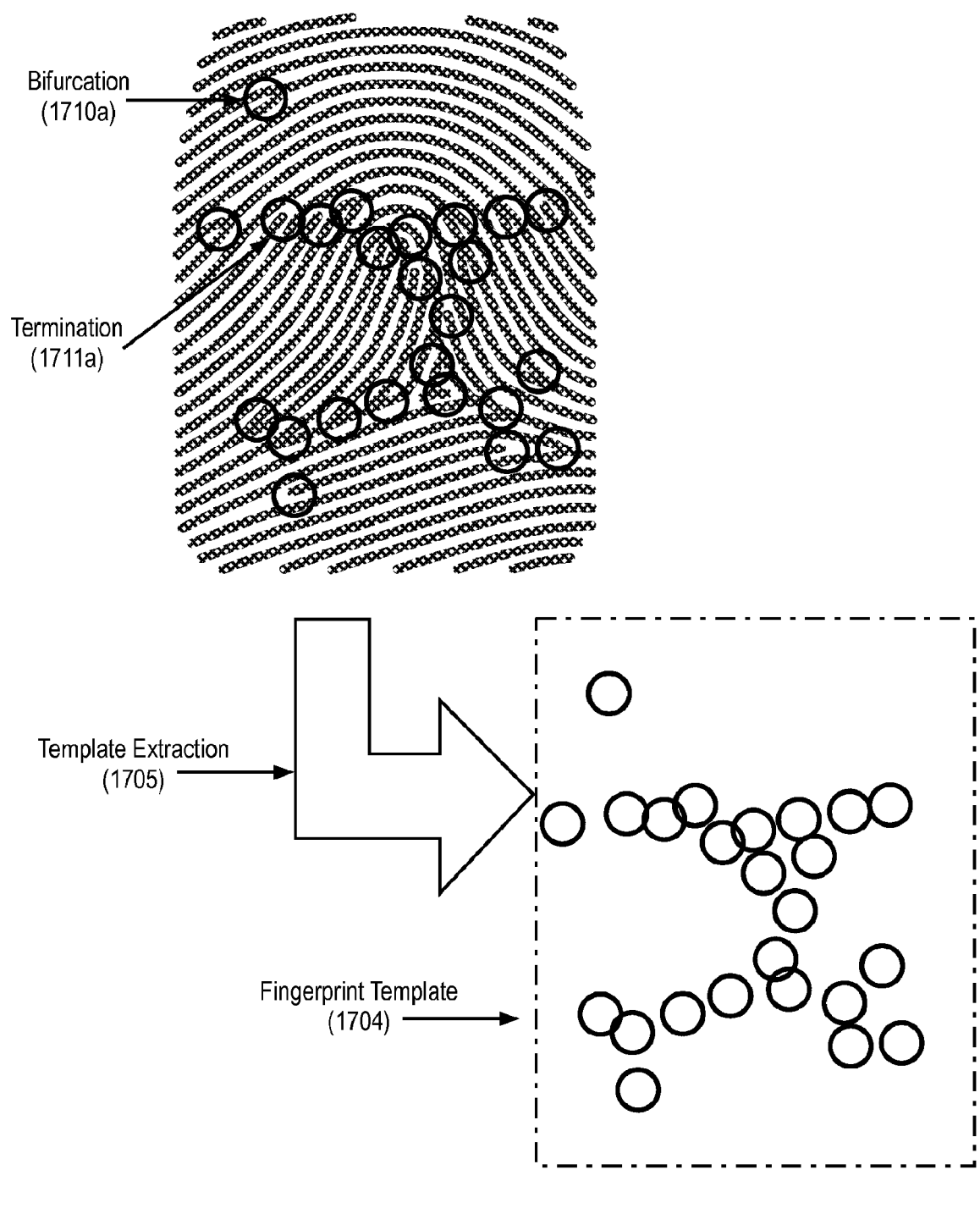
FIG. 17B shows the process of template extraction from a fingerprint image typically utilized in user authentication applications.

In FIG. 17, an example of the example as shown in FIG. 14 in a user authentication application. In step 1701a system level application 1440 on processor 1444 requires user authentication. At step 1702 the user is prompted to provide a finger for verification. The system waits for finger presence to be detected in step 1703. This can be performed by collecting a reduced size image as described in FIG. 16 and testing for finger image, or via other dedicated hardware. Once finger presence is detected, a complete image is collected in step 1704, using the method described in FIG. 16 or other substantially similar method. This image is then stored and in step 1705 converted into a template 1712 as shown in FIG. 17B, typically consisting of a map of minutia point locations and types (such as bifurcations 1710, and terminations 1711), or possibly of ridge frequency and orientation, or some combination of both. In step 1707 the template is then compared against one or more enrollment templates that were retrieved from persistent template storage 1142 in step 1706. If a match is found, the user is authenticated in step 1708 and granted access to the application. If no match is found, the user is rejected in step 1709, and access is denied.

In an authentication system such as described by FIGS. 16 and 17A-B, there can be a tradeoff between security and operational speed. A device such as a smartphone may have differing security and convenience (speed) requirements for differing operating modes, as well. These tradeoffs may be governed by the value of security for different types of information. As an example, users may place a low value on security for simply powering up their smartphone or other device. But, they may place a much higher value on performing a financial transaction or other sensitive transfer. They may want to lock out the ability to access personal contact information or customer lists, or may also want to lock out the ability for others to make local calls, long distance calls, access personal photos, access social networking websites, sent and receive text messages or emails, and they may want to have different security protocols for the access to different information. Users having conventional systems without the benefit of biometrics will typically lock their telephone handset with a four-digit PIN, which is a fairly low level of security. Securing a financial transaction over the same device, a new development that is desired in the industry, would cause a user to desire a much higher level of security. Conversely, the amount of time a user would find acceptable to unlock the phone for a simple call would be much shorter than the time they would wait to secure a high value transaction, where a user may be more tolerant of a higher time demand for authenticating the user for a financial transaction.

Embodiments described herein facilitate supporting both of these requirements by providing variable captured image resolution and matching algorithm security level. In one example, when operating in high security mode (such as when enrolling a user or validating a high-value transaction) the image capture procedure described in FIG. 16 and the match procedure described in FIG. 17A-B may operate in full resolution mode. When operating in convenience' mode (such as unlocking the phone, looking at photos, surfing the internet or switching users), the fingerprint image may be acquired in a half-resolution mode by skipping every other column and every other row—for example where steps 1608 and 1610 would increment the Column and Row counters, respectively, by two instead of one. This may result in an image with half the resolution in each axis compared to the high security mode, and one-fourth the size. This could cut by a factor of four both the time required to acquire the image (FIG. 16) and the time required to extract the template from the image (step 1705). Due to the reduced resolution of the image, and the relaxed security requirements for this convenience mode, the matching threshold applied in step 1707 may be accordingly reduced.

Figure 18A:
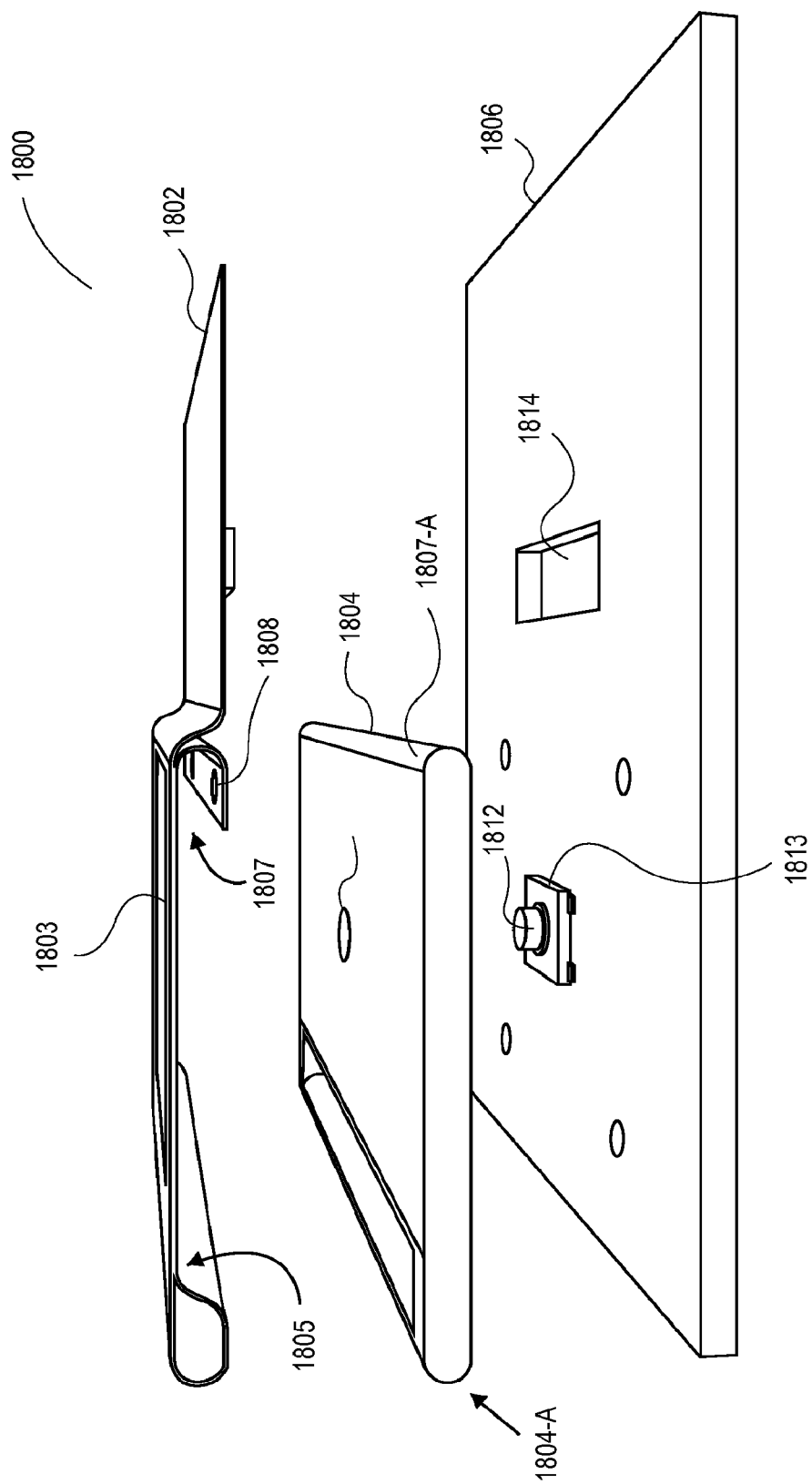
FIGS. 18A-18D show an example of a fingerprint sensor system having an integrated switch to allow a user to contact a fingerprint sensor and to actuate a switch simultaneously.

Referring to FIGS. 18A-D, another embodiment of a sensor module or assembly is illustrated as a sensor 1800, first shown in an expanded view in FIG. 18A, made up of a folded flex sensor 1802, a module folding base 1804 and mounting board 1806. In this embodiment, a switch having a plunger 1812 and base 1813 is incorporated into a sensor assembly that allows the integration of the sensor operations, such as fingerprint sensor operations, together with other operations of a device. Still further, this assembly allows for the configuration of a personalization switch for use on a device, such as a mobile telephone or smart phone for example, that has extended functions including biometric operations. If used together with a power or selector switch, such as for example a modular replacement for the main selection switch on an iPhone™ manufactured by Apple Computer Corporation or a navigation selection switch used on a BlackBerry™ smartphone manufactured by Research in Motion (RIM™) next to the display screen of these devices, a fingerprint sensor can be used for authentication while using these personal devices. The authentication can be used to access the device entirely, access different levels of information such as different information that a user wishes to protect, or could be used for authentication of the user for financial transactions that require a higher level of security. These settings maybe preset by the manufacturer, may be reset by the user, may be set by a financial institution associated with the user or the device, or may be configurable by anyone with an interest in protecting the information.

Still referring to FIG. 18A, the folded flex sensor 1802 may be folded at 1805 and 1807 respectively to fit about the module folding base 1804 at mounting locations loop brace 1805-A and folding edge 1807-A respectively, along with placement holes 1808 to aid in placing the flex about the module and holding it in place. If the embodiments of the flex sensor circuit formed or otherwise configure on a substrate according to the examples of FIG. 12A or 12B, different mounting operations may be required to accommodate these or other designs that requires a different folding or forming of the substrate. The sensor 1802 may include processor 1810 as described in similar embodiments above. Mounting board 1806 includes a switch 1813 mounted about switch opening 1811 to accommodate plunger 1812, and may also have a processor opening 1814 configured to accommodate processor 1810.

Figure 18B:
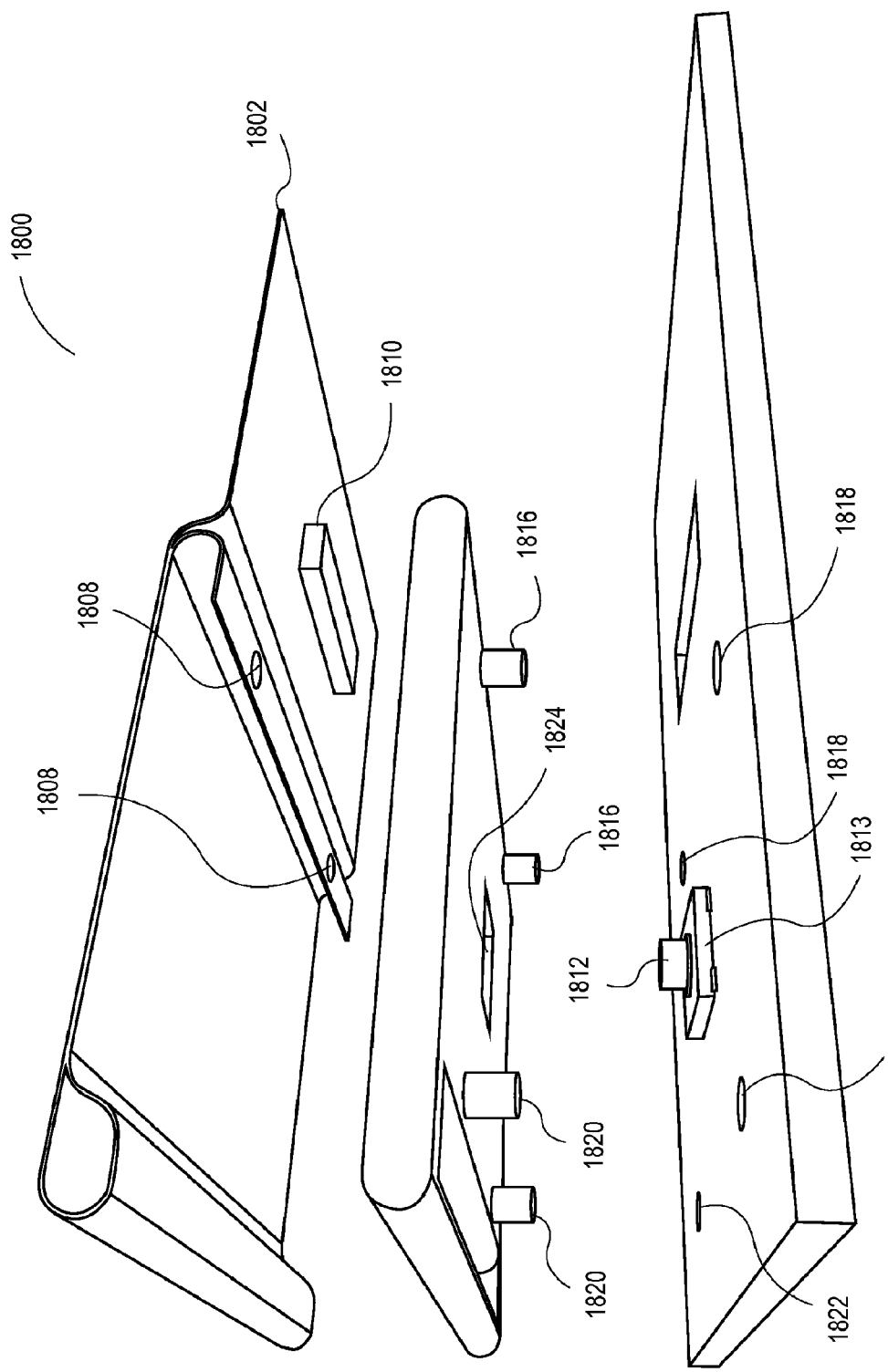

Referring to FIG. 18B, another expanded view of the sensor of FIG. 18A is shown from another angle, where one side of the flex sensor 1802 shows more clearly the openings 1808 and processor 1810, where the openings 1808 are configured to receive placement or mounting pegs 1816 for holding the sensor 1802 substrate in place and then received by mounting openings 1818. The placement or mounting pegs 1820 are received by mounting openings 1822. Switch base opening 1824 is configured to receive switch base 1813. In another embodiment, the opening for the plunger 1812 and the base 1813 may be a single sized opening that will accept the entire switch, or the switch may have base with the same diameter as the plunger so that a single cylindrical or rectangular or other shaped opening may be sufficient to accommodate the switch.

Figure 18C:
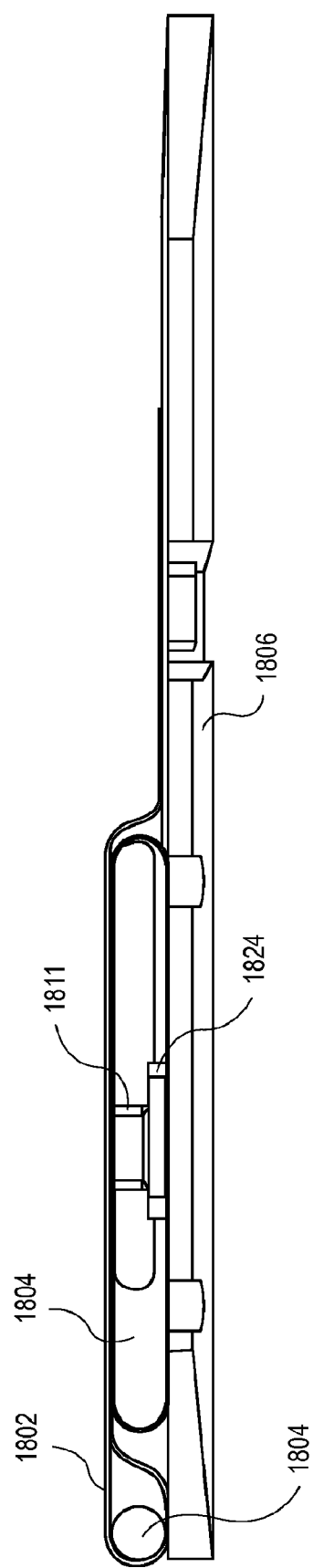
Figure 18D:
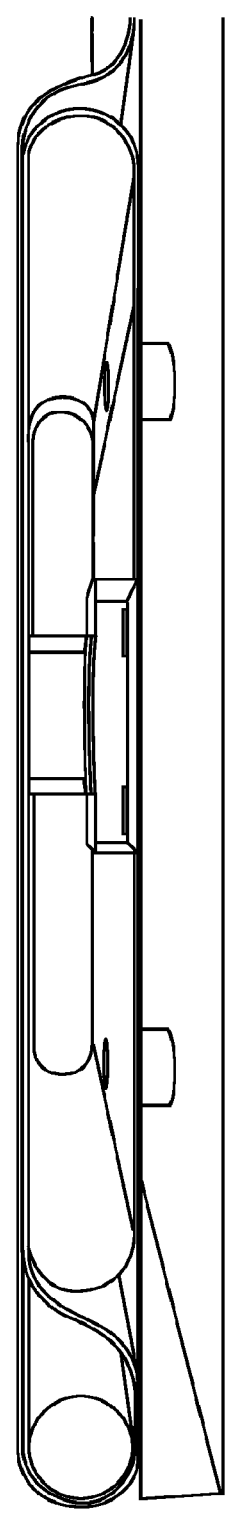

FIG. 18C shows a side cut away view of the assembled sensor assembly with the sensor substrate 1802 mounted on module folding base 1804 and mounted on base 1806, and with the openings 1811 and 1824 accommodating the switch plunger 1812 and switch base 1813 respectively. FIG. 18D shows a close-up view of the side view of FIG. 18C.

Figure 19A:
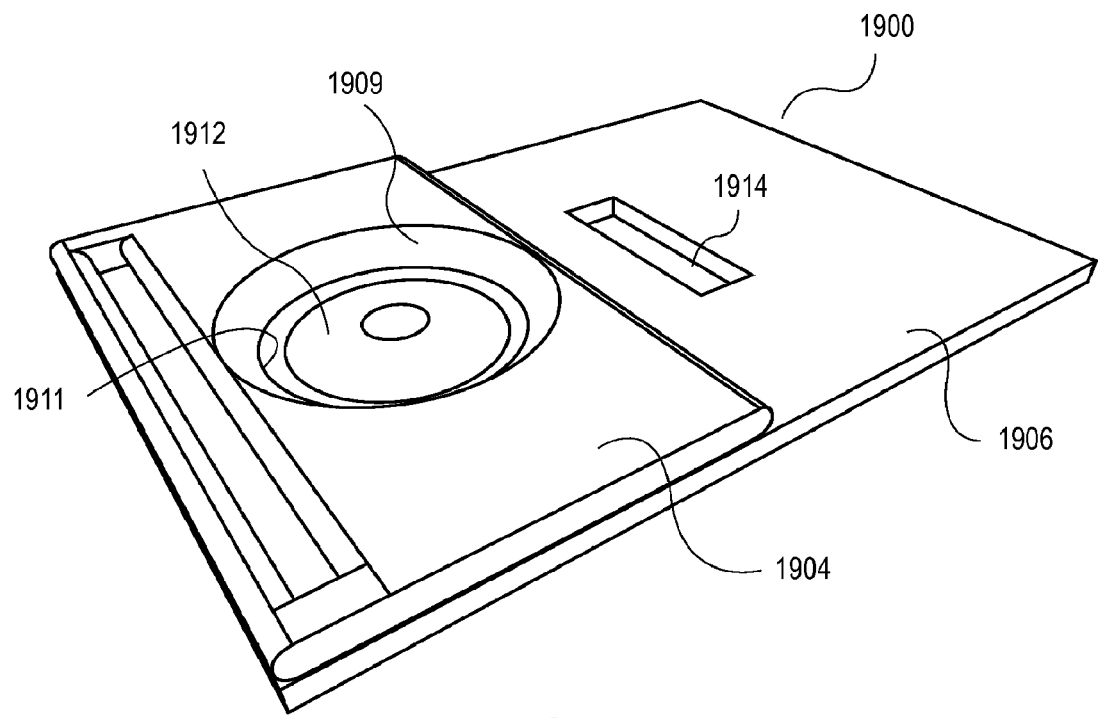
Figure 19B:
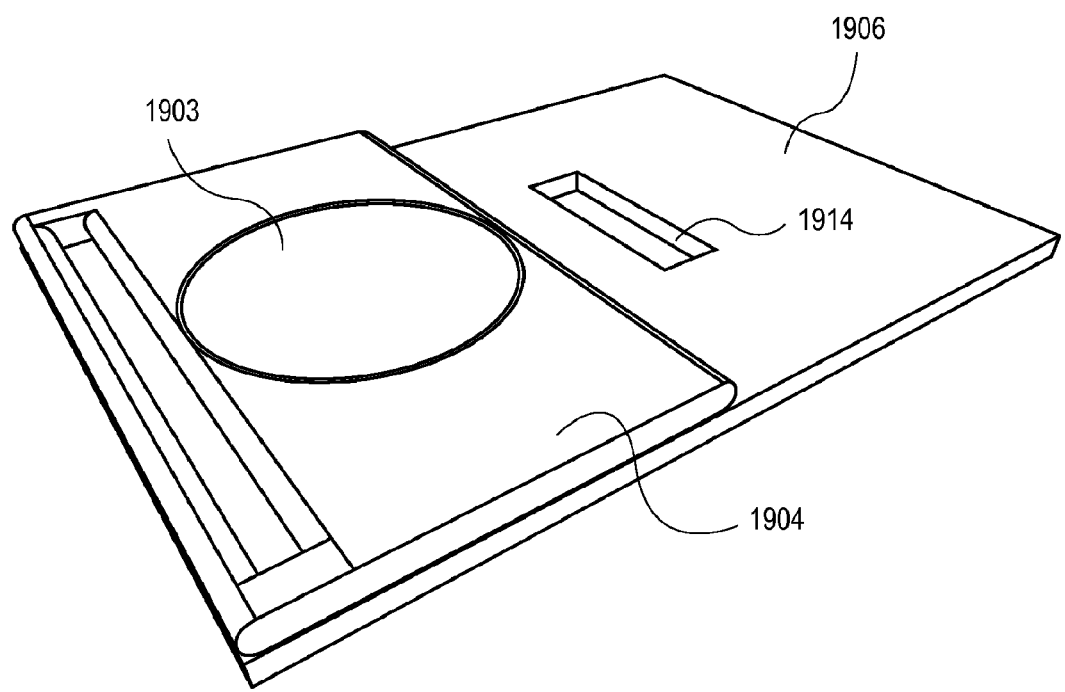
Figure 19C:
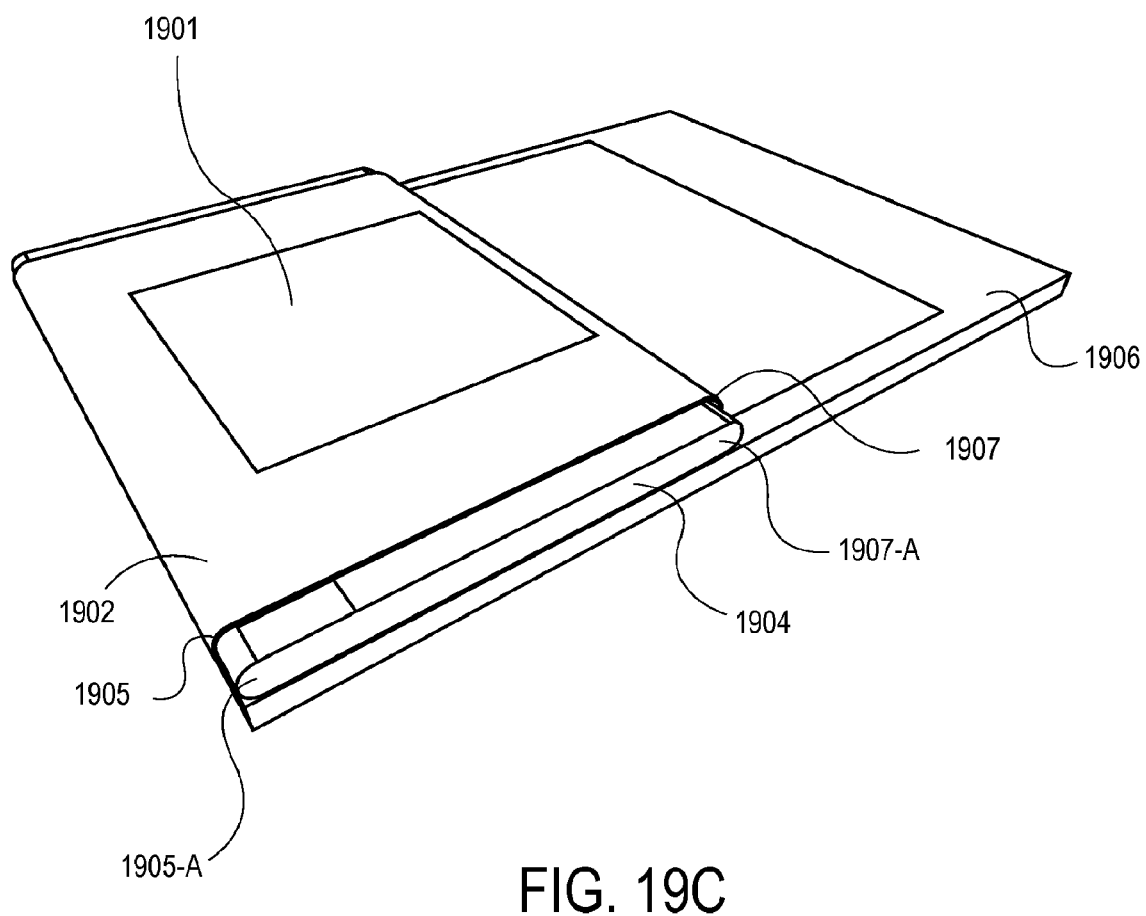

FIGS. 19A-J show an alternative sensor/switch assembly where a dome switch is used for the underlying switch that is integrated in the assembly. Referring to FIG. 19A, the assembly 1900 includes a dome switch 1912 integrated with module folding base 1904 mounted on mounting board 1906. In this embodiment, a switch having a domed shaped plunger 1912 and base 1913 (FIG. 19C) is incorporated into a sensor assembly that allows the integration of the sensor operations, such as fingerprint sensor operations, together with other operations of a device.

Figure 19D:
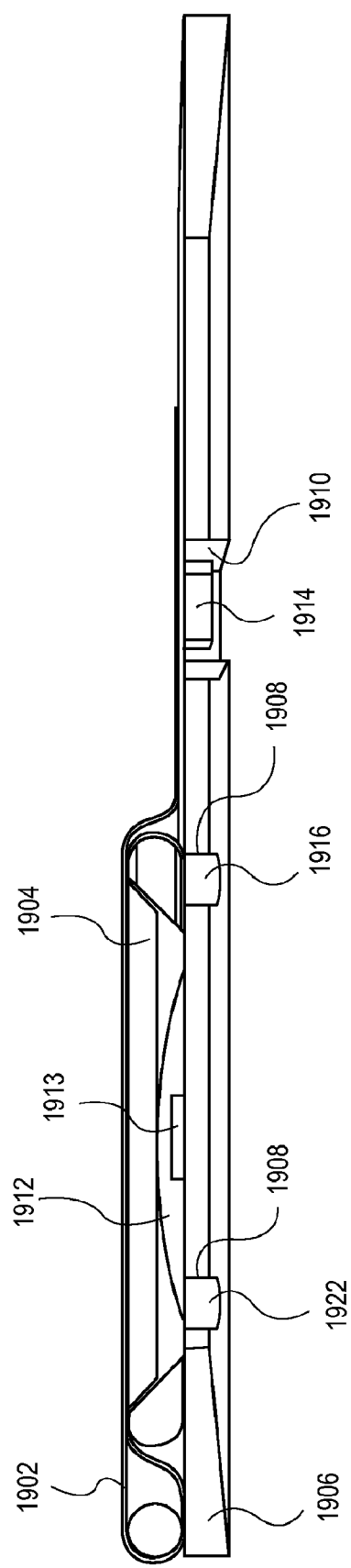

Referring to FIGS. 19A, B and C, the folded flex sensor 1902 may be folded at 1905 and 1907 respectively to fit about the module folding base 1904 at mounting locations loop brace 1905-A and folding edge 1907-A respectively, along with placement holes 1908 (FIG. 19D) to aid in placing the flex about the module and holding it in place. If the embodiments of the flex sensor circuit formed or otherwise configure on a substrate according to the examples of FIG. 12A or 12B, different mounting operations may be required to accommodate these or other designs that requires a different folding or forming of the substrate. The sensor 1902 may include processor 1910 as described in similar embodiments above. Mounting board 1906 includes a switch 1913 mounted below plunger 1912, and may also have a processor opening 1914 configured to accommodate processor 1910 (FIG. 19D).

Figure 19E:
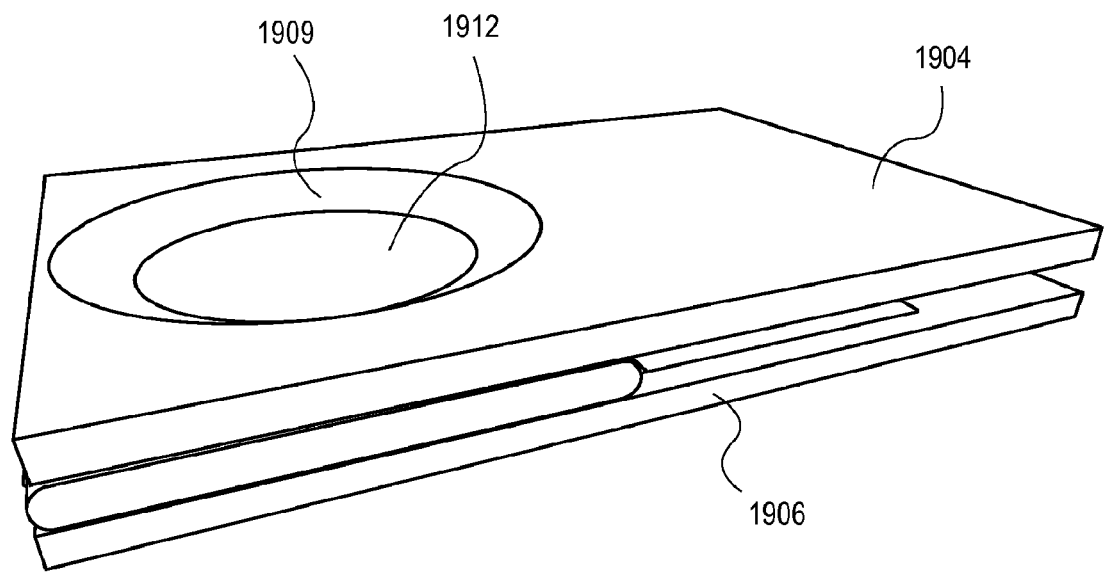
Figure 19F:
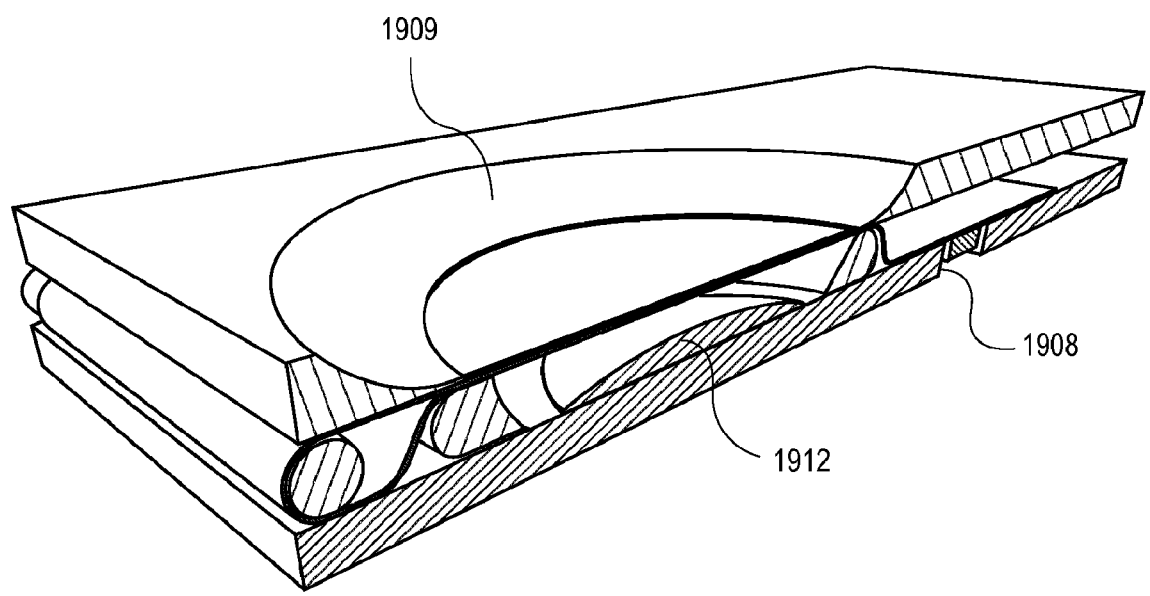
Figure 19G:
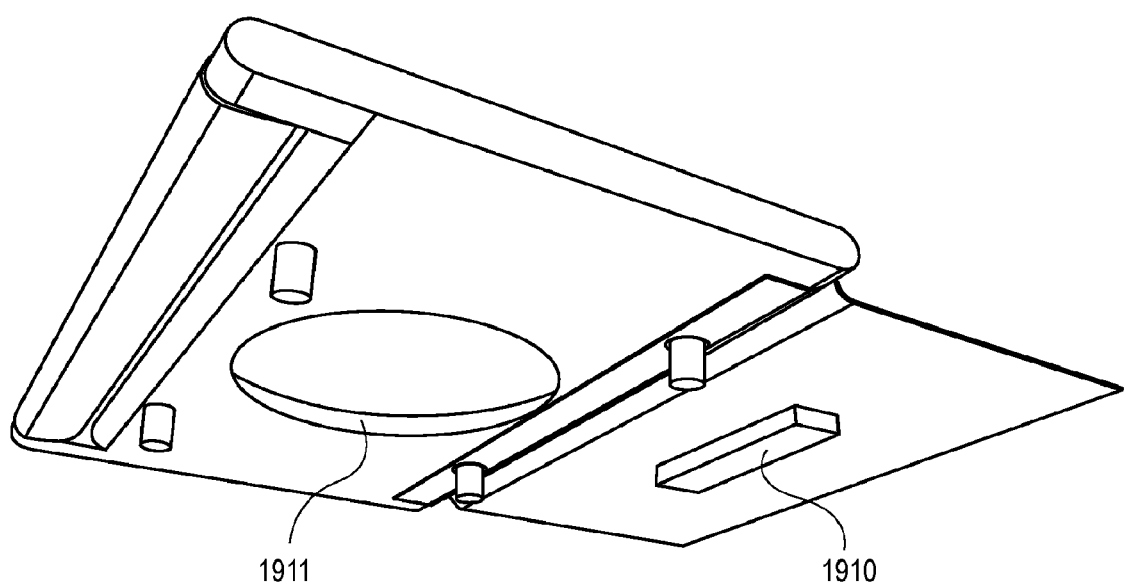
Figure 19J:
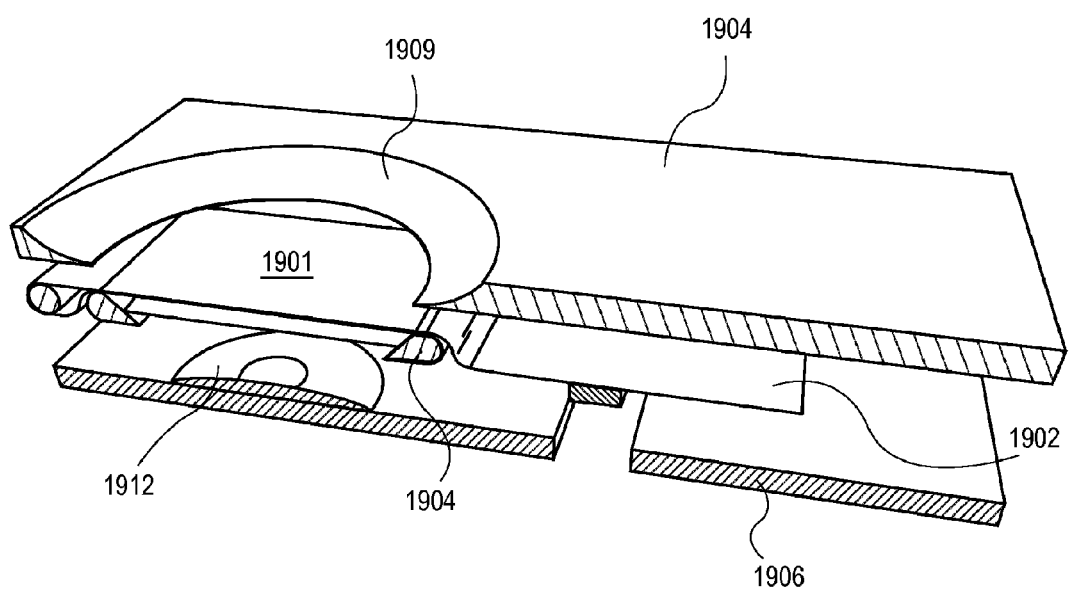

Referring to FIG. 19G, H and I, side views of the sensor is shown, showing the flex sensor 1902 and the openings 1908 and processor 1910, where the openings 1908 are configured to receive placement or mounting pegs 1916 for holding the sensor 1902 substrate in place and then received by mounting openings 1918. The placement or mounting pegs 1920 are received by mounting openings 1922. Switch base opening 1924 is configured to receive switch base 1913. In another embodiment, the opening for the plunger 1912 and the base 1913 may be a single sized opening that will accept the entire switch, or the switch may have base with the same diameter as the plunger so that a single cylindrical or rectangular or other shaped opening may be sufficient to accommodate the switch.

FIG. 19E,F, and J show a normal, cutaway, and expanded cut away views of the sensor assembly mounted in a device such as a smartphone, with the sensor substrate 1902 mounted on module folding base 1904 and mounted on base 1906, and with the openings 1911 and 1924 accommodating the switch dome plunger 1912 and switch base 1913 respectively. The sensor area 1901 is accessed by a bezel opening 1909 which is incorporated into the finished case 1925 of the device. When the user places a finger on sensor surface 1901 they will simultaneously depress switch plunger 1912.

Figure 20:
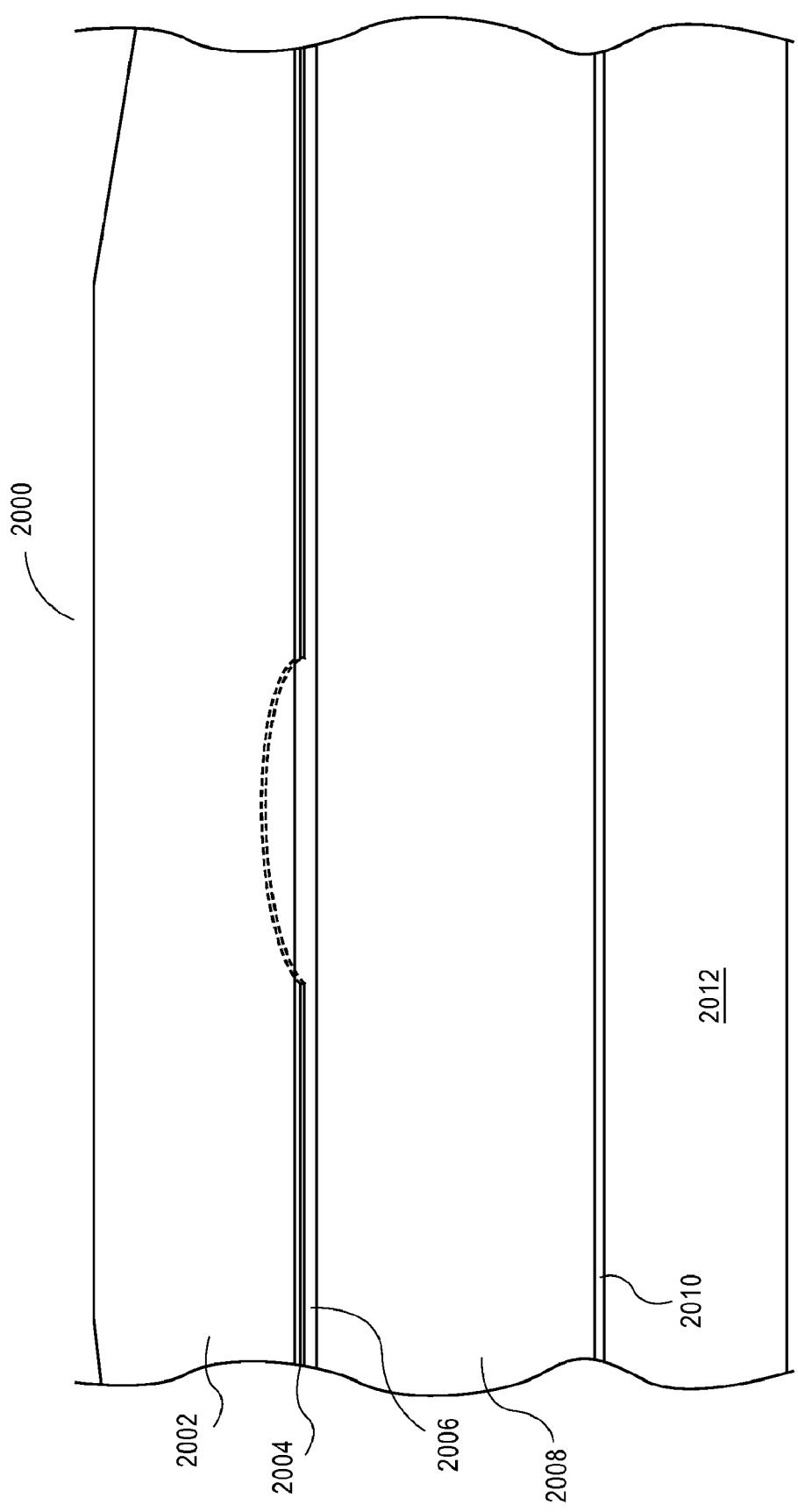
FIG. 20 shows a top view of an embodiment of a switch formed on the same substrate as the fingerprint sensor.

FIG. 20 illustrates a perspective view of one embodiment of an embedded switch 2000 that can provide a means to electronically connect a top conductive layer 2002 through insulating layer 2004 to conductive layer 2006 upon the touch of a user on the surface of the sensor, not shown here, but it may be a layer above conductor 2002. The three layers may be embedded within a fingerprint sensor as described above, allowing for a switch located within the double-layered fingerprint sensor, so that a user can activate a function upon touch, such as power, select, initiate, enter, or other switch functions in a device. The three layers may be placed on a surface 2006 of module 2008, where the module is located on the surface 2010 of a substrate 2012.

Figure 21A:
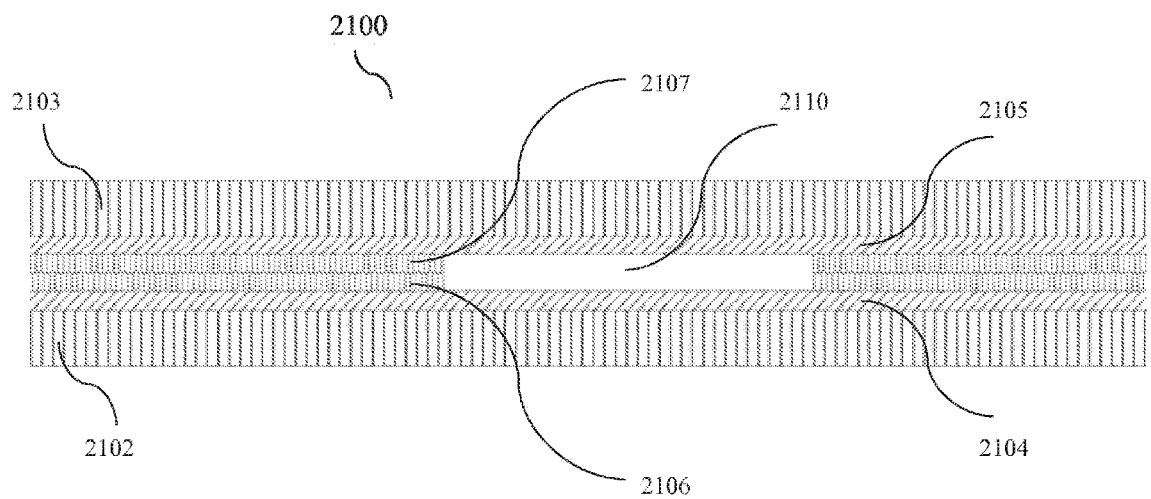
FIGS. 21A and B are detailed views which show the operation of the embedded switch depicted in FIG. 20.
Figure 21B:
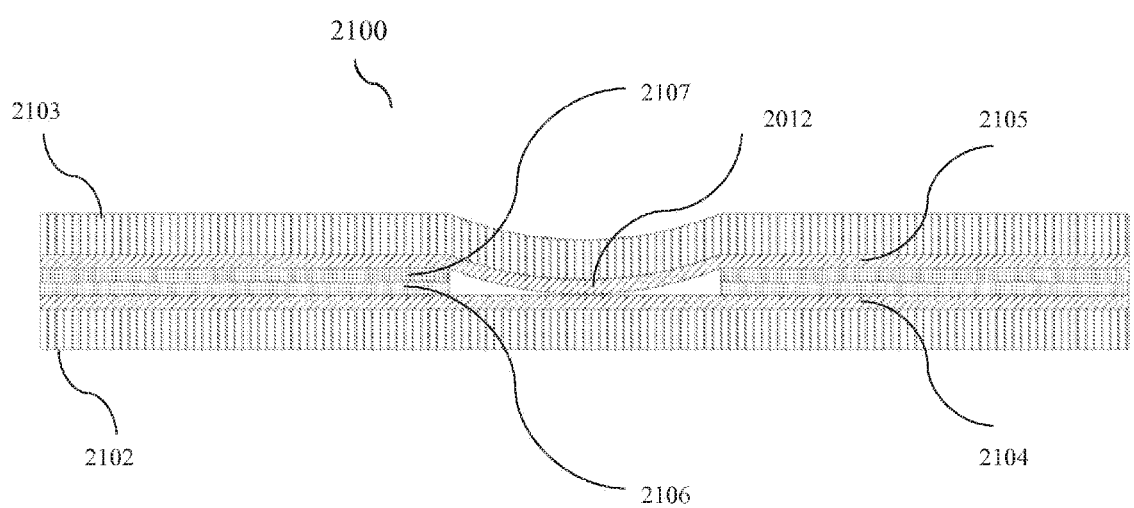

FIGS. 21A and 21B FIG. 21A shows an embodiment where a switch is formed on the same substrate as the sensor. The figures show the folded flex stack-up consisting of flex substrates 2102 and 2103, typically but not limited to Kapton®, metalized layers 2104 and 2105 are typically etched or formed copper traces and insulating layers 2106 and 2107 are typically solder mask. Insulating layers 2106 and 2107 have a cutout section 2110 out exposing the conductive layers 2104 and 2105. When no vertical pressure is applied over the gap 2110 conductive layers 2104 and 2105 are not electrically in contact with each other and are in the off position.

FIG. 21B shows the flex top layer 2103 and conductive layer 2112 mechanically depressed by a contacting object such as a finger. Top conductive layer 2107 can be pushed physically into electrical contact with conductive layer 2106 at pressure focal point 2112. This forms an embedded flex switch, which is shown in the on position.

FIGS. 22-26 illustrate alternative embodiments and further examples. These examples may be configured using different materials and structures, and they may further be oriented or integrated in different structures such as power buttons in mobile devices, stationary devices, computers, laptops, access devices (doorknobs, entryways, or the like). Note that in these figures and the number of plates is greatly reduced to simplify the drawings, and the size of individual drive and pickup plates are increased for simplicity as well. In practice, both drive and pickup plates may be formed at fixed or variable pitch, and unlike the drawings, the spacing between plates may be greater or less than the individual plate size.

FIGS. 22A-B depict an embodiment where the drive and detection electronics are implemented on separate silicon components. This configuration minimizes interconnect between layers by directly mounting the drive die on the substrate layer for the drive lines, and directly mounting the pickup die on the substrate for the pickup plates. The rigid substrate for the drive plates also serves as a common base layer which provides interconnect for synchronizing signals between the two subsystems, as well as power and communications to the host device.

In this particular example, the common substrate (2201) is a two layer rigid circuit board, which also provides a mechanical base for the sensor. The drive circuitry is implemented in integrated circuit die (2204) which is mounted on rigid drive substrate (2201). The die is connected to the circuit on the rigid substrate by a number of bonding pads (2206) using standard flip-chip mounting processes. A large number of drive lines (typically more than 100) are connected to the drive plates (2209), which are formed on the top side of the rigid substrate.

A dielectric layer (2208) separates drive plates (2209) from pickup plates (2210). In this instance dielectric layer (2208) is provided by a solder mask layer applied to the drive plates (2209) and rigid substrate (2201).

Pickup substrate assembly (2202) with pre-attached pickup circuit die (2205) is mounted on top of drive substrate (2201). The die is connected to the circuit on the flexible substrate by a number of bonding pads (2216) using standard flip-chip mounting processes. Because substrate (2202) is flexible, attach pads (2211) can mate with their corresponding pads (2212) on base substrate (2201). A cutout (2203) is provided in base substrate (2201) to accommodate pickup chip (2205) so the assembly lies flat. Attach pads (2211) provide interconnect to the mating pads (2212) on the substrate layer (2201).

Interconnect traces (2214) formed on the top layer of base substrate (2201) provide synchronizing signals between the integrated circuits (2204) and (2205).

Interconnect traces (2215) in the base substrate (2201) route signals to interconnect pads (2213) for power, ground, and communications interconnect to the host system.

FIGS. 23A-G illustrate an example of an assembly stackup of the two-chip. FIG. 23A shows the rigid base (2201) with the drive plates (2209), host interconnect traces (2215) and contact pads (2213), pickup communications traces (2214) and contact pads (2212). Cutout (2203) is mad in base (2201) to accommodate the pickup IC which will be attached in a subsequent step.

Rigid base (2201) could be fabricated from standard circuit board materials, such as FR4, in which case plates (2209), interconnect (2213 and 2214) and pads (2213 and 2212) would typically be formed from copper by use of circuit board etching techniques. Rigid base (2201) could also be formed from glass, in which case plates (2209), interconnect traces (2213 and 2214), and pads (2212 and 2213) would typically be formed from a transparent conductive material such as Indium-Tin Oxide (ITO).

FIG. 23B shows drive electronics die (2204) attached to the traces on the assembly from FIG. 23A. The die is shown attached to the traces via standard flip-chip mounting processes.

FIG. 23C shows the exemplary assembly after the addition of dielectric layer 2208. This dielectric layer may be formed by a standard soldermask process, such as LPI, or by applying a piece of dielectric such as Kapton® film.

FIG. 23D shows a cutaway view of the exemplary flexible substrate (2202) with pickup plates (2210) and pickup communications pads (2211) formed on it. Flexible substrate (2202) may be formed from a Kapton® film, in which case the plates (2210), traces, and pads (2211) would likely be formed of copper by standard etching techniques. Flexible substrate (2202) could also be made of a transparent material, such as polyester, with plates, traces, and pads formed from by depositing a film of a transparent conductive material such as ITO.

FIG. 23F shows the cutaway view of the exemplary flexible substrate with the addition of pickup electronics die (2205). Electrical connections between the die and elements on the flex are made by bonding interconnect bumps (2216) on the die to contacts (2217) on the flex assembly, as shown in FIG. 23E. Interconnect bumps (2216) are typically made of gold, while contacts (2217) are features formed of the same material as the plates and traces.

FIG. 23G shows a cutaway view of the exemplary completed assembly, as the flex assembly is mounted onto the rigid assembly. Electrical connection between the two sub-assemblies is made by mating flex assembly pads (2211) to rigid assembly pads (2212).

Figure 24:
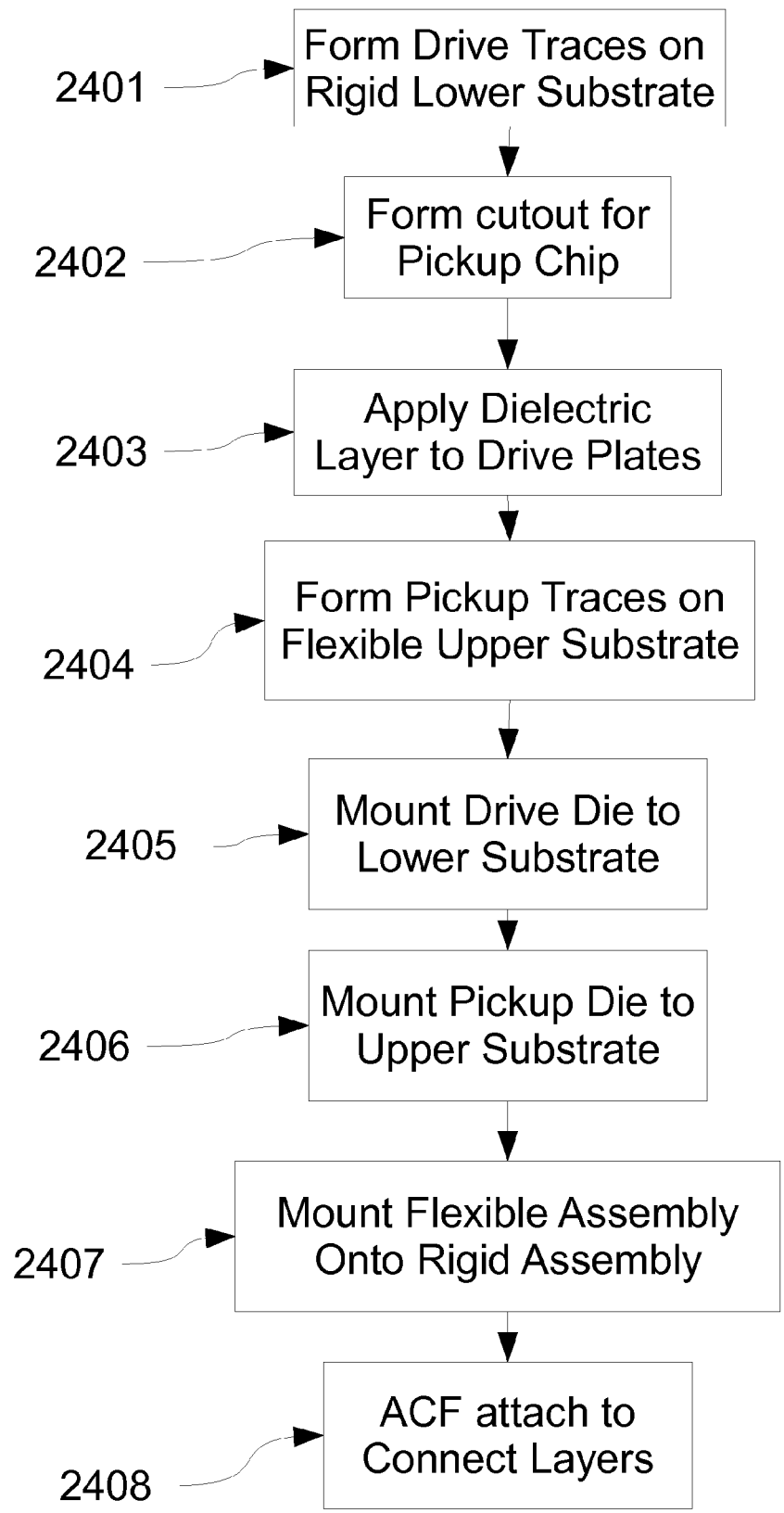

FIG. 24 shows an example of steps required to assemble the exemplary embodiment shown in FIGS. 22A-B and 23A-G. In Step 2401 traces 2214 and 2215, host contact pads 2213, layer interconnect pads 2212, and drive plates 2209 are all formed by an etching process on substrate 2201. A number of instances of the substrate assemblies may be formed at the same time by repeating the pattern across a large panel of base material. In Step 2402 cutout 2203 is formed in substrate 2203 by a standard circuit board routing process. This may take place at the same time that the multiple instances of substrate 2201 are separated by cutting out the substrate outline from the common panel. In Step 2403 dielectric layer 2208 is created by applying a layer of material such as LPI solder mask to substrate 2201 and drive plates 2209. In Step 2404 pickup plates 2210, interconnect pads 2211, and bonding pads 2217 are formed on substrate 2202 by an etching process. In Step 2405, drive electronics die 2204 is mounted onto the substrate assembly 2201 using a standard chip-on-board flip-chip bonding process. In Step 2406, pickup electronics die 2205 is mounted onto substrate assembly 2202 using standard flip-clip chip-on-flex bonding process. In Step 2407, flex substrate assembly 2202 is mounted onto base substrate assembly 2201. In Step 2408 pads 2211 and 2212 are electrically connected using an anisotropic conducting film (ACF) attach process.

FIGS. 25A-F show an embodiment where the drive and detection electronics are implemented on separate structures, such as separate silicon components for example. This configuration minimizes interconnect between layers by directly mounting the drive die on the substrate layer for the drive lines, and directly mounting the pickup die on the substrate for the pickup plates. The drive and pickup layers may be both connected to a common base layer which provides interconnect for synchronizing signals between the two subsystems, as well as power and communications to the host device. In this particular example, the common substrate (2500) may be a two layer rigid circuit board, which may also provide a mechanical base for the sensor. The drive circuitry may be implemented in integrated circuit die (2504) that is mounted on flexible drive substrate (2501). The die may be connected to the circuit on the flexible substrate by a number of bonding pads (2506) using standard flip-chip mounting processes or other mounting processes known in the art. A large number of drive lines (possibly 100 or more) may be connected to the drive plates (2509), which may or may not be formed on the same flexible substrate. Attach pads (2511) can provide interconnect to the mating pads (2512) on the substrate layer (2500). Substrate (2500) may incorporate a cutout (2513). In one example, the cutout may be configured so that when the drive substrate (2501) is attached drive electronics chip (2504) will not contact substrate (2501), and the assembly lies flat or planar. In another embodiment, a surface may not be entirely planar or even molded over an object such as a power button, the different layers may have a cutout to accommodate different structures such as the drive electronics. Pickup substrate assembly (2502) with pre-attached pickup circuit die (2505) may be mounted on top of both drive substrate (2501) and base substrate (2500). In this embodiment, drive substrate (2501) provides the dielectric layer between the drive and pickup plates, without the need for a separate dielectric layer as in previously discussed embodiments. If substrate (2502) is flexible, attach pads (2507a) may be able to mate with their corresponding pads (2507b) on base substrate (2500). A cutout (2503) may be provided in base substrate (2500) to accommodate pickup chip (2505) so the assembly lies flat. Interconnect traces (2514) formed on the top layer of base substrate (2500) may be included to provide synchronizing signals between the integrated circuits (2504) and (2505). Vias (2507c) or other openings in the base substrate (2500) may be used to route signals to the bottom layer, where lower layer traces (2509) may connect the signals to interconnect pads (2508) for possibly power, ground, communications interconnect to the host system, and other connections.

FIGS. 26A-C show an exemplary embodiment where the drive and detection electronics are both provided by a single integrated circuit. In one example, substrate (2601) may be composed of a dielectric material which separates the drive (2602) and pickup (2603) plates. Substrate (2601) may be a flexible material, such as Kapton®, or a thin rigid material, such as an aramid laminate layer in a FlipChip package, or it may be another material. Integrated circuit die (2604) incorporates contact pads (2611) which are mounted onto bonding pads (2605) the bottom layer of the substrate. The bonding pads provide connections from die (2604) to interconnect traces (2606), drive plates (2602), and pickup interconnect traces (2607). A number of vias (2609) electrically connect pickup interconnect (2607) on the bottom layer to pickup plates (2603), which may be located on the top layer. As shown in FIG. 26A, conductive traces (2612) on the top layer fan out from the ends of the pickup plates (2603) to the vias (2609). Each conductive trace (2612) connects an associated pickup plate (2603) to an associated via (2609). In the illustrated embodiment, the pickup plates (2603) are straight and parallel to each other along their entire length. The conductive traces (2612) are not straight or parallel to each other along their entire length. The spacing between adjacent vias (2609) is greater than the spacing between adjacent pickup plates (2603). Interconnect traces (2606) may connect die (2604) to host connector pads (2608). A dielectric layer (2610) may be formed atop pickup plated (2603) to prevent direct contact of the finger with the pickup plates. The dielectric layer (2610) may be formed from a number of materials, including but not limited to an LPI soldermask material, an ink, or a top Kapton® coversheet. In another embodiment, a surface may not be entirely planar or even molded over an object such as a power button, While certain exemplary embodiments have been described and shown in the accompanying drawings, it is to be understood that such embodiments are merely illustrative of and not restrictive on the broad embodiment, and that this embodiment is not limited to the specific constructions and arrangements shown and described, since various other modifications may occur to those ordinarily skilled in the art. Hence, alternative arrangements and/or quantities of, connections of various sorts, arrangements and quantities of transistors to form circuits, and other features and functions can occur without departing from the spirit and scope of the embodiment. Similarly, components not explicitly mentioned in this specification can be included in various embodiments of this embodiment without departing from the spirit and scope of the embodiment. Also, different process steps and integrated circuit manufacture operations described as being performed to make certain components in various embodiments of this embodiment can, as would be apparent to one skilled in the art, be readily performed in whole or in part to make different components or in different configurations of components not explicitly mentioned in this specification without departing from the spirit and scope of the embodiment. Accordingly, the specification and drawings are to be regarded in an illustrative rather than a restrictive sense.

While certain exemplary embodiments have been described and shown in the accompanying drawings, it is to be understood that such embodiments are merely illustrative of and not restrictive on the broad embodiment, and that this embodiment is not limited to the specific constructions and arrangements shown and described, since various other modifications may occur to those ordinarily skilled in the art. Accordingly, the specification and drawings are to be regarded in an illustrative rather than a restrictive sense.

Again, the embodiment has application in many areas, particularly in biometric sensors. Fingerprint sensors, for example, and other biometric sensors are gaining increasing acceptance for use in a wide variety of applications for security and convenience reasons. Devices, systems and methods configured according to the embodiment will have improved security of the biometric verification process without increasing the cost of the system. Furthermore, the embodiment may extend to devices, systems and methods that would benefit from validation of components. As discussed above, the embodiment includes the ability for the host and sensor to include any combination or subset of the above components, which may be arranged and configured in the manner most appropriate for the system's intended application. Those skilled in the art will understand that different combinations and permutations of the components described herein are possible within the spirit and scope of the embodiment, which is defined by the appended Claims, their equivalents, and also Claims presented in related applications in the future and their equivalents.

The embodiment may also involve a number of functions to be performed by a computer processor, such as a microprocessor. The microprocessor may be a specialized or dedicated microprocessor that is configured to perform particular tasks according to the embodiment, by executing machine-readable software code that defines the particular tasks embodied by the embodiment. The microprocessor may also be configured to operate and communicate with other devices such as direct memory access modules, memory storage devices, Internet related hardware, and other devices that relate to the transmission of data in accordance with the embodiment. The software code may be configured using software formats such as Java, C++, XML (Extensible Mark-up Language) and other languages that may be used to define functions that relate to operations of devices required to carry out the functional operations related to the embodiment. The code may be written in different forms and styles, many of which are known to those skilled in the art. Different code formats, code configurations, styles and forms of software programs and other means of configuring code to define the operations of a microprocessor in accordance with the embodiment will not depart from the spirit and scope of the embodiment.

Within the different types of devices, such as laptop or desktop computers, hand held devices with processors or processing logic, and also possibly computer servers or other devices that utilize the embodiment, there exist different types of memory devices for storing and retrieving information while performing functions according to the embodiment. Cache memory devices are often included in such computers for use by the central processing unit as a convenient storage location for information that is frequently stored and retrieved. Similarly, a persistent memory is also frequently used with such computers for maintaining information that is frequently retrieved by the central processing unit, but that is not often altered within the persistent memory, unlike the cache memory. Main memory is also usually included for storing and retrieving larger amounts of information such as data and software applications configured to perform functions according to the embodiment when executed by the central processing unit. These memory devices may be configured as random access memory (RAM), static random access memory (SRAM), dynamic random access memory (DRAM), flash memory, and other memory storage devices that may be accessed by a central processing unit to store and retrieve information. During data storage and retrieval operations, these memory devices are transformed to have different states, such as different electrical charges, different magnetic polarity, and the like. Thus, systems and methods configured according to the embodiment as described herein enable the physical transformation of these memory devices. Accordingly, the embodiment as described herein is directed to novel and useful systems and methods that, in one or more embodiments, are able to transform the memory device into a different state. The embodiment is not limited to any particular type of memory device, or any commonly used protocol for storing and retrieving information to and from these memory devices, respectively.

The term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present embodiment. The machine-readable medium includes any mechanism that provides (i.e., stores and/or transmits) information in a form readable by a machine (e.g., a computer, PDA, cellular telephone, etc.). For example, a machine-readable medium includes memory (such as described above); magnetic disk storage media; optical storage media; flash memory devices; biological electrical, mechanical systems; electrical, optical, acoustical or other form of propagated signals (e.g., carrier waves, infrared signals, digital signals, etc.). The device or machine-readable medium may include a micro-electromechanical system (MEMS), nanotechnology devices, organic, holographic, solid-state memory device and/or a rotating magnetic or optical disk. The device or machine-readable medium may be distributed when partitions of instructions have been separated into different machines, such as across an interconnection of computers or as different virtual machines.

While certain exemplary embodiments have been described and shown in the accompanying drawings, it is to be understood that such embodiments are merely illustrative of and not restrictive on the broad embodiment, and that this embodiment not be limited to the specific constructions and arrangements shown and described, since various other modifications may occur to those ordinarily skilled in the art. Accordingly, the specification and drawings are to be regarded in an illustrative rather than a restrictive sense.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances "an embodiment," "one embodiment," or "some embodiments" are not necessarily all referring to the same embodiments. If the specification states a component, feature, structure, or characteristic "may", "might", or "could" be included, that particular component, feature, structure, or characteristic is not required to be included. If the specification or Claim refers to "a" or "an" element, that does not mean there is only one of the element. If the specification or Claims refer to "an additional" element, that does not preclude there being more than one of the additional element.

The methods, systems and devices include improved security operations and configurations with a novel approach to biometric systems. Such systems would greatly benefit from increased security features, particularly in financial transactions. Although this embodiment is described and illustrated in the context of devices, systems and related methods of validating biometric devices such as fingerprint sensors, the scope of the embodiment extends to other applications where such functions are useful. Furthermore, while the foregoing description has been with reference to particular embodiments of the embodiment, it will be appreciated that these are only illustrative of the embodiment and that changes may be made to those embodiments without departing from the principles of the embodiment, the scope of which is defined by the appended Claims and their equivalents.

The invention claimed is:

1. A biometric sensor, comprising:
a plurality of drive lines;
a plurality of pickup lines oriented transversely to the drive lines and separated from the drive lines by a substrate;
an integrated circuit comprising drive electronics and detection electronics, wherein the substrate is disposed between the pickup lines and the integrated circuit, wherein the drive electronics comprise switches configured to multiplex the drive lines to a signal source, and wherein the detection electronics comprise one or more differential amplifiers and switches configured to multiplex the pickup lines to the one or more differential amplifiers; and
vias extending through the substrate for providing an electrical connection between the pickup lines and the integrated circuit.

2. The biometric sensor of claim 1, further comprising a reference pickup line located outside a contact area defined by the drive lines and the pickup lines, and wherein the detection electronics are configured to subtract a signal on a pickup plate in contact with an object contacting the contact area from a signal on the reference pickup line.

3. The biometric sensor of claim 1, wherein the switches of the detection electronics comprise a pickup switch associated with each pickup line for selectively connecting each pickup plate with the differential amplifier and for connecting each pickup line not connected to the differential amplifier to ground.

4. The biometric sensor of claim 2, wherein the reference pickup line is separated from the other pickup plates by a first gap that is larger than a second gap separating the other pickup lines.

5. The biometric sensor of claim 1, wherein the switches of the detection electronics comprise single pole double throw switches.

6. The biometric sensor of claim 1, wherein the switches of the drive electronics comprise single pole single throw switches.

7. The biometric sensor of claim 1, wherein the substrate has a top layer and a bottom layer, and wherein the pickup lines are located on the top layer and the integrated circuit is located on the bottom layer.

8. The biometric sensor of claim 7, further comprising a plurality of pickup interconnects disposed on the bottom layer of the substrate and being connected to the integrated circuit, and wherein each via is connected to an associated one of the pickup interconnects.

9. The biometric sensor of claim 1, wherein the substrate is composed of a dielectric material.

10. The biometric sensor of claim 1, wherein the substrate is composed of a flexible material.

11. The biometric sensor of claim 1, further comprising a dielectric layer disposed on top of the pickup lines.

12. The biometric sensor of claim 1, wherein the substrate is composed of a rigid material.

13. The biometric sensor of claim 1, wherein each via is electrically coupled to one associated pickup line and extends through the substrate and to an associated pickup interconnect that extends to the integrated circuit.

14. The biometric sensor of claim 1, wherein the drive lines are parallel to one another and the pickup lines are parallel to one another.

15. The biometric sensor of claim 1, wherein the pickup lines are disposed on a first side of the substrate and the drive lines are disposed on a second side of the substrate opposite the first side.

16. The biometric sensor of claim 15, wherein the integrated circuit is disposed on the second side of the substrate.

17. The biometric sensing assembly of claim 16, wherein the integrated circuit comprises drive electronics and detection electronics, wherein the drive electronics comprise switches configured to multiplex the drive lines to a signal source, and wherein the detection electronics comprise one or more differential amplifiers and switches configured to multiplex the pickup lines to the one or more differential amplifiers.

18. The biometric sensor of claim 1, further comprising a plurality of conductive traces, each conductive trace including a first end connected to an end of an associated one of the pick-up lines and a second end, wherein each of the vias is connected to the second end of an associated one of the conductive traces to provide the electrical connection between the associated pickup line and the integrated circuit.

19. The biometric sensor of claim 18, wherein the pickup lines are parallel to one another along their entire length, and the conductive traces are not parallel to one another along their entire length.

20. The biometric sensing assembly of claim 19, wherein the switches of the detection electronics comprise a pickup switch associated with each pickup line for selectively connecting each pickup plate with the differential amplifier and for connecting each pickup line not connected to the differential amplifier to ground.

21. The biometric sensing assembly of claim 19, wherein the switches of the detection electronics comprise single pole double throw switches.

22. The biometric sensing assembly of claim 19, wherein the switches of the drive electronics comprise single pole single throw switches.

23. The biometric sensor of claim 1, wherein each via is associated with a pickup plate and the spacing between adjacent vias is greater than the spacing between associated pickup plates.

24. A biometric sensor assembly, comprising:
a sensing grid comprising
a plurality of parallel drive lines; and
a plurality of parallel pickup lines oriented transversely to the drive lines and separated from the drive lines by a substrate, so as to form a capacitive sensing element at each location at which a pickup line overlaps a drive line;
an integrated circuit for controlling the sensing grid, wherein the substrate is disposed between the pickup lines and the integrated circuit;
a plurality of conductive traces, each conductive trace including a first end connected to an end of an associated one of the pick-up lines and a second end; and
a plurality of vias, each of the vias being connected to the second end of an associated one of the conductive traces and extending through the substrate for providing an electrical connection between the associated pickup line and the integrated circuit.

25. The biometric sensing assembly of claim 24, further comprising a reference pickup line located outside the sensing grid, and wherein the detection electronics are configured to subtract a signal on a pickup plate in contact with an object contacting at least a portion of the sensing grid from a signal on the reference pickup line.

26. The biometric sensing assembly of claim 24, wherein the reference pickup line is separated from the other pickup plates by a first gap that is larger than a second gap separating the other pickup lines.

27. The biometric sensing assembly of claim 26, further comprising a plurality of pickup interconnects disposed on the bottom layer of the substrate and being connected to the integrated circuit, and wherein each via is connected to an associated one of the pickup interconnects.

28. The biometric sensing assembly of claim 24, wherein the substrate has a top layer and a bottom layer, and wherein the pickup lines are located on the top layer and the integrated circuit is located on the bottom layer.

29. The biometric sensor assembly of claim 24, wherein the substrate is composed of a dielectric material.

30. The biometric sensor assembly of claim 24, wherein the substrate is composed of a rigid material.

31. The biometric sensor assembly of claim 24, wherein the substrate is composed of a flexible material.

32. The biometric sensor assembly of claim 24, further comprising a dielectric layer disposed on top of the pickup lines.

33. The biometric sensor assembly of claim 24, wherein each via is associated with a pickup plate and the spacing between adjacent vias is greater than the spacing between associated pickup plates.

* * * * *